US007744873B2

(12) United States Patent
Clark et al.

(10) Patent No.: US 7,744,873 B2
(45) Date of Patent: Jun. 29, 2010

(54) METHOD FOR TREATING GLAUCOMA COMPRISING ADMINISTERING TO A PATIENT IN NEED THEREOF A COMPOSITION COMPRISING AN ANTIBODY AGAINST GREMLIN

(75) Inventors: Abbot F. Clark, Arlington, TX (US); Robert J. Wordinger, Euless, TX (US)

(73) Assignees: Alcon, Inc., Hunenberg (CH); University of North Texas Health Science Center, Fort Worth, TX (US)

( * ) Notice: Subject to any disclaimer, the term of this patent is extended or adjusted under 35 U.S.C. 154(b) by 0 days.

(21) Appl. No.: 12/106,653

(22) Filed: Apr. 21, 2008

(65) Prior Publication Data
US 2008/0194515 A1 Aug. 14, 2008

Related U.S. Application Data

(63) Continuation of application No. 10/286,152, filed on Oct. 31, 2002, now Pat. No. 7,405,192.

(60) Provisional application No. 60/334,852, filed on Oct. 31, 2001.

(51) Int. Cl.
*A61K 39/00* (2006.01)
*C07K 18/00* (2006.01)
(52) U.S. Cl. ............ 424/130.1; 424/145.1; 530/387.1
(58) Field of Classification Search ........................ None
See application file for complete search history.

(56) References Cited

U.S. PATENT DOCUMENTS

| 5,145,871 | A | 9/1992 | Cavazza |
| 5,364,884 | A | 11/1994 | Varma et al. |
| 6,207,450 | B1 | 3/2001 | Sheffield et al. |
| 6,248,571 | B1 | 6/2001 | Schmidt et al. |
| 6,248,867 | B1 | 6/2001 | Nguyen et al. |
| 6,613,563 | B1 | 9/2003 | Sosnowski et al. |

FOREIGN PATENT DOCUMENTS

| WO | 9614411 | 5/1996 |
| WO | 9820889 | 5/1998 |
| WO | 0061774 | 10/2000 |
| WO | 0068247 | 11/2000 |
| WO | 0077021 | 12/2000 |
| WO | 02077006 | 10/2002 |
| WO | 02085909 | 10/2002 |

OTHER PUBLICATIONS

Stabile et al., Blood, 109: 1834-1840, 2007.*
Lappin et al., Nephrol. Dial. Transpl., 17 (Suppl): 65-67, 2002.*
Agarwal et al., "Expression of Transforming Growth Factor Beta Isoforms (TGF-β 1-3) and Receptors (TGFβ RI-RIII) in Cultured Human Trabecular Meshwork Cells", IOVS 38(4):S563 (1997).
Agarwal R, et al., "FAS-activated apoptosis and other apoptosis mediators in human trabecular meshwork cells," Exp. Eye Res. 68:583-590 (1999.
Agarwal et al., "The Expression of Bone Morphogenetic Protein (BMP) and BMP Receptor mRNA by Human Trabecular Meshwork and Optic Nerve Head Cells and Tissues", IOVS 41(4):S506 (2000).
Astrom, A.K., et al., "Chromosomal localization of three human genes encoding bone morphogenetic protein receptors", Mammalian Genome 10(3):299-302 (1999).
Attisano L, Tuen Lee-Hoeflich S, "The Smads," Genome Biol. 2(8) Reviews/3010.1 (2001) 1-8.
Bengtsson B, "Incidence of manifest glaucoma," Br J Ophthalmol, 73:483-487 (1989).
Birren, et al., Genome Analysis, A Laboratory Manual vol. 2 Detecting Genes, (Bruce Birren ed., Cold Spring Harbor Laboratory Press 1998) 287-292.
Chang et al., "Haploinsufficient Bmp4 ocular phenotypes include anterior segment dysgenesis with elevated intraocular pressure", BioMed Central, BMC Genetics, 2:18 (2001).
Chundru et al., "Detection of neurotrophins in human aqueous humor," Invest. Ophthalmol. Vis. Sci. 41(4):S326 (2000).
Clark AF, et al., "Glucocorticoid-induced formation of cross-linked actin networks in cultured human trabecular meshwork cells," Invest. Ophthalmol. & Vis. Sci. 35(1):281-294 (1994).
Clark AF, et al., "Cell biology of the human lamina cribrosa," In Drance SM (ed). Optic Nerve in Glaucoma. Kugler Publications, New York: pp. 79-105 (1995).
Clark AF, et al., "Cytoskeletal changes in cultured human glaucoma trabecular meshwork cells," J. Glaucoma 4:183-188 (1995).
Clark AF, et al., "Dexamethasone-induced ocular hypertension in perfusion-cultured human eyes," Invest. Ophthalmol. & Vis. Sci. 36(2):478-489 (1995).
Clark AF, et al., "Inhibition of dexamethasone-induced cytoskeletal changes in cultured human trabecular meshwork cells by tetrahydrocortisol," Invest. Ophthalmol. & Vis. Sci. 37(5):805-813 (1996).
Clark AF, et al., "Expression of the glaucoma gene myocilin (MYOC) in the human optic nerve head," FASEB J. 15:1251-1253 (2001).
Clark AF, et al., "Glucocorticoid induction of the glaucoma gene MYOC in human and monkey trabecular meshwork cells and tissues," Invest. Ophthalmol. & Vis. Sci. 42(8):1769-1780 (2001).
Cummings, Michael R., Human Heredity, Fourth Edition, (West/Wadsworth 1997) 266-283.
Dickerson JE, et al., "The effect of dexamethasone on integrin and laminin expression in cultured human trabecular meshwork cells," Exp. Eye Res. 66:731-738 (1998).

(Continued)

*Primary Examiner*—Robert Landsman
*Assistant Examiner*—Gyan Chandra
(74) *Attorney, Agent, or Firm*—Jason J. Derry

(57) ABSTRACT

The present invention provides methods and kits for diagnosing and treating glaucoma.

1 Claim, 26 Drawing Sheets

OTHER PUBLICATIONS

Dudley et al., "A requirement for bone morphogenic protein-7 during development of the mammalian kidney and eye," Genes & Development 9:2795-2807 (1995).

Elbashir SM, et al., "Duplexes of 21-nucleotide RNAs mediate RNA interference in cultured mammalian cells", Nature 411:494-498, 2001.

Encio et al., "The Genomic Structure of the Human Glucocorticoid Receptor", J. Biol. Chem. 266(11):7182-7188 (1991).

Furuta and Hogan, "BMP4 is essential for lens induction in the mouse embryo," Genes & Dev. 12:3764-3775 (1998).

Giguère et al., "Functional Domains of the Human Glucocorticoid Receptor", Cell 46:645-652 (1986).

Greve, M. et al., "Comparison of the oculokinetic perimetry glaucoma screener with two types of visual filed analyser", Can. J. Ophthamol. 28(5):201-206 (1993).

Grierson I et al., "Characteristics of Meshwork Cells and Age Changes in the Outflow System of the Eye: Their Relevance to Primary Open Angle Glaucoma." In Mills KB (ed). Glaucoma. Proceedings of the Fourth International Symposium of the Northern Eye Institute, Manchester, UK, New York, Pergamon: pp. 12-31 (1988).

Gutteridge, "Normal tension glaucoma: diagnostic features and comparison with primary open angle glaucoma"; Clinical and Exp. Optometry; 83: 161-172 (2000).

Hernandez M and Gong H, "Extracellular matrix of the trabecular meshwork and optic nerve head." in Ritch R., Shields, M.B., Krupin, T. (eds). The Glaucomas, 2nd ed. St Louis: Mosby-Year; pp. 213-249 (1996).

Hernandez, et al., "Changes in the Extracellular Matrix of the Human Optic Nerve Head in Primary Open-Angle Glaucoma," Am. J. Ophthalmol. 109:180-188 (1990).

Hernandez MR and Pena JD, "The optic nerve head in glaucomatous optic neuropathy," Arch Ophthalmol. 115:389-395 (1997).

Hitchings RA, "Glaucoma screening", Br. J. Ophthamol. 77:326 (1993).

Jain, R.; "Vascular and interstitial barriers to delivery of therapeutic agents in tumors"; Cancer and Metastasis Reviews; 9; 253-266 (1990).

Liu X., et al.; Human trabecular meshwork cells express the ciliary neurotrophic factor (CNTF) tripartate receptor complex; Exp. Eye Res.; 72:711-717 (2001).

Hogan BL, "Bone morphogenic proteins: multifunctional regulators of vertebrate development," Genes Dev. 10:1580-1594 (1996).

Hollenberg et al., "Primary Structure and Expression of a Functional Human Glucocorticoid Receptor cDNA", Nature 318(19):635-641 (1985).

Hu and Ritch, "Hepatocyte Growth Factor is Increased in the Aqueous Humor of Glaucomatous Eyes," J. Glaucoma 10:152-157 (2001).

Inatani et al., "Transforming growth factor β2 levels in aqueous humor of glaucomatous eyes," Graefes Arch. Clin. Exp. Ophthalmol. 239:109-113 (2001).

Itoh et al., "Signaling of transforming growth factor-β family members through Smad proteins", Eur. J. Biochem. 267:6954-6967 (2000).

Jacobson N, et al., "Non-secretion of mutant proteins of the glaucoma gene myocilin in cultured trabecular meshwork cells and in aqueous humor," Human Molecular Genetics 10(2):117-125 (2001).

Jena et al., "BMP7 null mutation in mice: developmental defects in skeleton, kidney, and eye," Exp. Cell Res. 230:28-37 (1997).

Jorde, et al., Medical Genetics, Second Edition, (Mosby 1999) 29-57.

Kawabata et al., "Signal Transduction by Bone Morphogenetic Proteins", Cytokine & Growth Factor Reviews, vol. 9, No. 1, 49-61 (1998).

Kerrigan et al., "TUNEL-positive ganglion cells in human primary open-angle glaucoma," Arch. Ophthalmol. 115:1031-1035 (1997).

Lambert et al., "Expression of TGF-Beta Isoforms and Their Receptor mRNA'S in Cultured Human Lamina Cribrosa Cells", IOVS 38(4):S162 (1997).

Lambert, et al. "Map Kinase Activation and Cell Proliferation of Cultured Lamina Cribrosa Cells Following Exogenous NGF Treatment", IOVS 41(4):S827 (2000).

Lambert W, et al., "Neurotrophin and neurotrophin receptor expression by cells from the human lamina cribrosa," Invest. Ophthalmol. Vis. Sci., 42(10):2315-2323 (2001).

Leske MC, et al., "The Epidemiology of Open-Angle Glaucoma: A Review", American Journal of Epidemilogy, 118(2):166-191 (1983).

Liu et al., "Expression of Ciliary Neurotrophic Factor (CNTF), Glial Derived Neurotrophic Factor (GDNF) and Their Receptors by Cells of the Human Optic Nerve Head", IOVS 40(4):S673 (1999).

Luo et al. , "BMP-7 is an inducer of nephrogenesis, and is also required for eye development and skeletal patterning," Genes & Development 9:2808-2820 (1995).

Lütjen-Drecoll E. and Rohen J.W., "Morphology of aqueous outflow pathways in normal and glaucomatous eyes," in Ritch R., Shields, M.B., Krupin, T. (eds). The Glaucomas, 2nd ed. St Louis: Mosby-Year; pp. 89-123 (1996).

McMahon R., et al., "IHG-2, a Mesangial Cell Gene Induced by High Glucose, Is Human gremlin", J. Biol. Chem. 275 (14):9901-9904 (2000).

Miyazono, "Positive and negative regulation of TGF-b signaling", J. Cell Science, 113:1101-1109 (2000).

Mohan, et al., "Bone morphogenic proteins 2 and 4 and their receptors in the adults human cornea," Invest. Ophthalmol. & Vis. Sci. 39(13):2626-2636 (1998).

Morrison JC, et al., "Optic nerve head extracellular matrix in primary optic atrophy and experimental glaucoma," Arch. Ophthalmol. 108:1020-1024 (1990).

Murphy, M., et al., "Suppression Subtractive Hybridization Identified High Glucose Levels as a Stimulus for Expression of Connective Tissue Growth Factor and Other Genes in Human Mesangial Cells", J. Biol. Chem. 274(9):5830-5834 (1999).

Nickel et al., "The Crystal Structure of the BMP-2:BMPR-IA Complex and the Generation of BMP-2 Antagonists", J Bone & Joint Surgery 83-A(suppl 1):S1-7-S1-14 (2001).

Nohno, T., et al., "Identification of a Human Type II Receptor for Bone Morphogenetic Protein-4 That Forms Differential Heteromeric Complexes with Bone Morphogenetic Protein Type I Receptors", J. Biol. Chem. 270(38):22522-22526 (1995).

Nonner et al., "Bone morphogenic proteins (BMP6 and BMP7) enhance the protective effect of neurotrophins on cultured septal cholinergic neurons during hypoglycemia," Journal of Neurochemistry 77:691-699 (2001).

Oakley et al., "The Human Glucocorticoid Receptor β Isoform", J. Biol. Chem. 271(16):9550-9559 (1996).

Oakley et al., "Expression and Subcellular Distribution of the β-Isoform of the Human Glucocorticoid Receptor", Endocrinology 138(11):5028-5038 (1997).

Obata et al., "Expression of transforming growth factor-beta superfamily receptors in rat eyes," Acta. Ophthalmol. Scand. 77:151-156 (1999).

Pang I-H, et al., "Human ocular perfusion organ culture: a versatile ex vivo model for glaucoma research," J. Glaucoma 9:468-479 (2000).

Pena et al, "Transforming growth factor beta isoforms in human optic nerve heads," Br. J. Ophthalmol. 83:209-218 (1999).

Picht et al, "Transforming growth factor β2 levels in the aqueous humor in different types of glaucoma and the relation to filtering bleb development," Graefes Arch. Clin. Exp. Ophthalmol. 239:199-207 (2001).

Quigley HA, et al., "Retinal ganglion cell death in experimental glaucoma and after axotomy occurs by apoptosis," Invest. Ophthalmol. Vis. Sci. 36(5):774-786 (1995).

Quigley HA, "Neuronal death in glaucoma," Prog. Retin. Eye Res. 18:39-57 (1999).

Quigley HA, et al., "Retrograde axonal transport of BDNF in retinal ganglion cells is blocked by acute IOP elevation in rats," Invest. Ophthalmol. Vis. Sci. 41(11):3460-3466 (2000).

Reddi, "Bone morphonegetic proteins: an unconventional approach to isolation of first mammalian morphogens," Cytokine & Growth Factor Rev. 8(1):11-20 (1997).

Reddi, "Bone morphogenic proteins and skeletal development: the kidney-bone connection," Pediatr Nephrol. 14:598-601 (2000).

Rohen JW, "Why is Intraocular Pressure Elevated in Chronic Simple Glaucoma? Anatomical considerations." Ophthalmology 90:758-765 (1983).

Steely HT, et al., "The effects of dexamethasone on fibronectin expression in cultured human trabecular meshwork cells," Invest. Ophthalmol. Vis. Sci. 33(7): 2242-2250 (1992).

Steely HT, et al., "The Similarity of protein expression in trabecular meshwork and lamina cribrosa: implications for glaucoma," Exp. Eye Res. 70:17-30 (2000).

Stone EM, et al., "Identification of a gene that causes primary open angle glaucoma," Science 275:668-670 (1997).

Strong, N. P., "How optometrists screen for glaucoma: A survey", Ophthal. Physiol. Opt., 12:3-7 (1992).

ten Dijke, PP, et al., "Activin receptor-like kinases: a novel subclass of cell-surface receptors with predicted serine/threonine kinase activity", Oncogene 8(10):2879-2887 (1993).

Tripathi RC, et al., "Analysis of Human Aqueous Humor for Epidermal Growth Factor," Exp. Eye Res. 53:407-409 (1991).

Tripathi RC, et al., "Detection, quantification, and significance of basic fibroblast growth factor in the aqueous humor of man, cat, dog and pig," Exp. Eye Res. 54:447-454 (1992).

Tripathi RC, et al., "Trabecular cells of the eye express messenger RNA for transforming growth factor-beta 1 and secrete this cytokine," Invest. Ophthalmol. Vis. Sci. 34(8):2562-2569 (1993).

Tripathi RC, et al., "Aqueous Humor in Glaucomatous Eyes Contains an Increased Level of TFG-β2," Exp. Eye Res. 59:723-727 (1994).

Tripathi RC, et al., "Immunolocalization of bFGF in the Trabecular Meshwork and Detection of its mRNA in Trabecular Cells," Exp. Eye Res. 58:503-507 (1994).

Tripathi RC, et al., "Trabecular Cells Express the TFG-β2 Gene and Secrete the Cytokine," Exp. Eye Res. 58:523-528 (1994).

Tripathi RC, et al., "Clinical implications of aqueous humor growth factors in glaucoma," in Ritch R., Shields, M.B., Krupin, T. (eds). The Glaucomas, 2nd ed. St Louis: Mosby-Year; pp. 71-87 (1996).

Trousse F et al., "BMP4 mediates apoptotic cell death in the developing chick eye," J. Neurosci. 21(4):1292-1301 (2001).

Tuck MW, et al., "Relative effectiveness of different modes of glaucoma screening in optometric practice", Ophthal. Physiol. Opt., 13:227-232 (1993).

Varma R and Minckler D, "Anatomy and pathophysiology of the retina and optic nerve." in Ritch R., Shields, M.B., Krupin, T. (eds). The Glaucomas, 2nd ed. St Louis: Mosby-Year; pp. 139-175 (1996).

Vaughan, D. et al., In: General Ophthalmology, Appleton & Lange, Norwalk, Conn., pp. 213-230 (1992).

Vernon, SA, "Intra-Eye Pressure Range and Pulse Profiles in Normals With the Pulsair Non-Contact Tonometer", Eye 7:134-137 (1993).

von Bubnoff A and Cho KW, "Intracellular BMP signaling regulation in vertebrates: pathway or network?" Dev. Biol. 239:1-14 (2001).

Wang W-H, et al., "Optimal procedure for extracting RNA from human ocular tissues and expression profiling of the congenital glaucoma gene FOXC1 using quantitative RT-PCR," Molecular Vision 7:89-94 (2001).

Wilson K, et al., "Dexamethasone induced ultrastructural changes in cultured human trabecular meshwork cells," Current Eye Research 12(9):783-793 (1993).

Wordinger RJ, et al., "Cultured human trabecular meshwork cells express functional growth factor receptors," Invest. Ophthalmol. & Vis. Sci. 39(9): 1575-1589 (1998).

Dermer, G; "Another anniversary for the war on cancer"; Bio/Technology; 12:320 (1994).

Liu Y, et al.; The effect of bone morphogenic protein-7 (BMP-7) on functional recovery, local cerebral glucose utilization and blood flow after transient focal cerebral ischemia in rats; Brain Res.; 905:81-90 (2001).

Nishimura, et al.; The forkhead transcription factor gene FKHL7 is responsible for glaucoma phenotypes which map to 6p25; Nature Gen.; 19:140-147; (1998).

Strachan, et al.; Molecular pathology; Human Molecular Genetics; Chapter 15; pp. 401-426; (1996).

Taniguchi, et al.; Clinical phenotype of a Japanese family with primary open angle glaucoma caused by a Pro370Leu mutation in the MYOC/TIGR Gene; Japan J. Ophthalmol; 43:80-84 (1999).

Tripathi RC, et al. Trabecular cells express receptors that bind TGF-beta and TGF-beta 2: a qualitative and quantitative characterization; Invest. Ophthalmol. Vis. Sci; 34(1):260-263 (1993b).

Wordinger et al.; The expression of ciliary neurotrophic factor (CNTF), glial derived neurotrophic factor (GDNF) and their receptors by human trabecular meshwork (TM); Cells and Tissues, IVOS; 40(4):S504 (1999).

Wordinger, RJ, et al.; Expression of alternatively spliced growth factor receptor isoforms in the human trabecular meshwork; Invest. Ophthalmol. Vis. Sci.; 40(1):242-247 (1999).

Wordinger RJ, et al.; Expression of bone morophogenetic proteins (BMP), BMP receptors, and BMP associated proteins in human trabecular meshwork and optic nerve head cells and tissues; Molecular Vision; 8:241-250 (2002).

Wordinger RJ, et al.; Human trabecular meshwork cells secrete neurotrophins and express neurotrophin receptors (Trk),; Invest. Ophthalmol. & Vis. Sci.; 41:3833-3841; (2000).

Yamashita et al., "Bone morphogenic protein receptors," Bone 19:569-574 (1996).

You et al., "Bone morphogenic proteins and growth and differentiation factors in the human cornea," Invest. Ophthalmol. & Vis. Sci. 40(2):296-311 (1999).

Zhang et al., "Development of bone morphogenetic protein receptors in the nervous system and possible roles in regulating trkC expression," J. Neurosci. 18:3314-3326 (1998).

NCBI Entrez database nucleotide sequences, National Center for Biotechnology Information, National Library of Medicine, NIH (Bethesda, MD, USA) Accession No. M19481, Apr. 27, 1993.

NCBI Entrez database nucleotide sequences, National Center for Biotechnology Information, National Library of Medicine, NIH (Bethesda, MD, USA) Accession No. Z22535, Sep. 29, 1993.

NCBI Entrez database nucleotide sequences, National Center for Biotechnology Information, National Library of Medicine, NIH (Bethesda, MD, USA) Accession No. M22849, Oct. 31, 1994.

NCBI Entrez database nucleotide sequences, National Center for Biotechnology Information, National Library of Medicine, NIH (Bethesda, MD, USA) Accession No. X51801, Mar. 23, 1995.

NCBI Entrez database nucleotide sequences, National Center for Biotechnology Information, National Library of Medicine, NIH (Bethesda, MD, USA) Accession No. U31202, Dec. 13, 1995.

NCBI Entrez database nucleotide sequences, National Center for Biotechnology Information, National Library of Medicine, NIH (Bethesda, MD, USA) Accession No. X98494, Jul. 9, 1997.

NCBI Entrez database nucleotide sequences, National Center for Biotechnology Information, National Library of Medicine, NIH (Bethesda, MD, USA) Accession No. AF090189, Mar. 12, 1999.

NCBI Entrez database nucleotide sequences, National Center for Biotechnology Information, National Library of Medicine, NIH (Bethesda, MD, USA) Accession No. M60314, Dec. 22, 1999.

NCBI Entrez database nucleotide sequences, National Center for Biotechnology Information, National Library of Medicine, NIH (Bethesda, MD, USA) Accession No. U89326, Feb. 28, 2000.

NCBI Entrez database nucleotide sequences, National Center for Biotechnology Information, National Library of Medicine, NIH (Bethesda, MD, USA) Accession No. AF110137, Jul. 27, 2000.

NCBI Entrez database nucleotide sequences, National Center for Biotechnology Information, National Library of Medicine, NIH (Bethesda, MD, USA) Accession No. NM_001204, Oct. 31, 2000.

NCBI Entrez database nucleotide sequences, National Center for Biotechnology Information, National Library of Medicine, NIH (Bethesda, MD, USA) Accession No. NM_001202, Oct. 31, 2000.

NCBI Entrez database nucleotide sequences, National Center for Biotechnology Information, National Library of Medicine, NIH (Bethesda, MD, USA) Accession No. AF209930, Aug. 3, 2001.

* cited by examiner

FIG. 1a / 15

```
1     ggggacttct tgaacttgca gggagaataa cttGCGCACC CCACTTTGCG CCGGTGCCTT

61    TGCCCCAGCG GAGCCTGCTT CGCCATCTCC GAGCCCCACC GCCCCTCCAC TCCTCGGCCT

121   TGCCCGACAC TGAGACGCTG TTCCCAGCGT GAAAAGAGAG ACTGCGCGGC CGGCACCCGG

181   GAGAAGGAGG AGGCAAAGAA AAGGAACGGA CATTCGGTCC TTGCGCCAGG TCCTTTGACC

241   AGAGTTTTTC CATGTGGACG CTCTTTCAAT GGACGTGTCC CCGCGTGCTT CTTAGACGGA
```

|     |     |     |     |     | THR | MET | VAL | ALA | GLY | THR | ARG | 7 |
|-----|-----|-----|-----|-----|-----|-----|-----|-----|-----|-----|-----|---|
| 301 | CTGCGGTCTC | | CTAAAGGTCG | | ACC | ATG | GTG | GCC | GGG | ACC | CGC | |

|     | CYS | LEU | LEU | ALA | LEU | LEU | LEU | PRO | GLN | VAL | LEU | 18 |
|-----|-----|-----|-----|-----|-----|-----|-----|-----|-----|-----|-----|----|
| 342 | TGT | CTT | CTA | GCG | TTG | CTG | CTT | CCC | CAG | GTC | CTC | |

|     | LEU | GLY | GLY | ALA | ALA | GLY | LEU | VAL | PRO | GLU | LEU | 29 |
|-----|-----|-----|-----|-----|-----|-----|-----|-----|-----|-----|-----|----|
| 375 | CTG | GGC | GGC | GCG | GCT | GGC | CTC | GTT | CCG | GAG | CTG | |

|     | GLY | ARG | ARG | LYS | PHE | ALA | ALA | ALA | SER | SER | GLY | 40 |
|-----|-----|-----|-----|-----|-----|-----|-----|-----|-----|-----|-----|----|
| 408 | GGC | CGC | AGG | AAG | TTC | GCG | GCG | GCG | TCG | TCG | GGC | |

|     | ARG | PRO | SER | SER | GLN | PRO | SER | ASP | GLU | VAL | LEU | 51 |
|-----|-----|-----|-----|-----|-----|-----|-----|-----|-----|-----|-----|----|
| 441 | CGC | CCC | TCA | TCC | CAG | CCC | TCT | GAC | GAG | GTC | CTG | |

|     | SER | GLU | PHE | GLU | LEU | ARG | LEU | LEU | SER | MET | PHE | 62 |
|-----|-----|-----|-----|-----|-----|-----|-----|-----|-----|-----|-----|----|
| 474 | AGC | GAG | TTC | GAG | TTG | CGG | CTG | CTC | AGC | ATG | TTC | |

|     | GLY | LEU | LYS | GLN | ARG | PRO | THR | PRO | SER | ARG | ASP | 73 |
|-----|-----|-----|-----|-----|-----|-----|-----|-----|-----|-----|-----|----|
| 507 | GGC | CTG | AAA | CAG | AGA | CCC | ACC | CCC | AGC | AGG | GAC | |

|     | ALA | VAL | VAL | PRO | PRO | TYR | MET | LEU | ASP | LEU | TYR | 84 |
|-----|-----|-----|-----|-----|-----|-----|-----|-----|-----|-----|-----|----|
| 540 | GCC | GTG | GTG | CCC | CCC | TAC | ATG | CTA | GAC | CTG | TAT | |

|     | ARG | ARG | HIS | SER | GLY | GLN | PRO | GLY | SER | PRO | ALA | 95 |
|-----|-----|-----|-----|-----|-----|-----|-----|-----|-----|-----|-----|----|
| 573 | CGC | AGG | CAC | TCA | GGT | CAG | CCG | GGC | TCA | CCC | GCC | |

|     | PRO | ASP | HIS | ARG | LEU | GLU | ARG | ALA | ALA | SER | ARG | 106 |
|-----|-----|-----|-----|-----|-----|-----|-----|-----|-----|-----|-----|-----|
| 606 | CCA | GAC | CAC | CGG | TTG | GAG | AGG | GCA | GCC | AGC | CGA | |

|     | LA  | ASN | THR | VAL | ARG | SER | PHE | HIS | HIS | GLU | GLU | 117 |
|-----|-----|-----|-----|-----|-----|-----|-----|-----|-----|-----|-----|-----|
| 639 | GCC | AAC | ACT | GTG | CGC | AGC | TTC | CAC | CAT | GAA | GAA | |

FIG. 1b / 15

|  |  |  |  |  |  |  |  |  |  |  |  |
|---|---|---|---|---|---|---|---|---|---|---|---|
| 672 | SER TCT | LEU TTG | GLU GAA | GLU GAA | LEU CTA | PRO CCA | GLU GAA | THR ACG | SER AGT | GLY GGG | LYS AAA | 128 |
| 705 | THR ACA | THR ACC | ARG CGG | ARG AGA | PHE TTC | PHE TTC | PHE TTT | ASN AAT | LEU TTA | SER AGT | SER TCT | 139 |
| 738 | ILE ATC | PRO CCC | THR ACG | GLU GAG | GLU GAG | PHE TTT | ILE ATC | THR ACC | SER TCA | ALA GCA | GLU GAG | 150 |
| 771 | LEU CTT | GLN CAG | VAL GTT | PHE TTC | ARG CGA | GLU GAA | GLN CAG | MET ATG | GLN CAA | ASP GAT | ALA GCT | 161 |
| 804 | LEU TTA | GLY GGA | ASN AAC | ASN AAT | SER AGC | SER AGT | PHE TTC | HIS CAT | HIS CAC | ARG CGA | ILE ATT | 172 |
| 837 | ASN AAT | ILE ATT | TYR TAT | GLU GAA | ILE ATC | ILE ATA | LYS AAA | PRO CCT | ALA GCA | THR ACA | ALA GCC | 183 |
| 870 | ASN AAC | SER TCG | LYS AAA | PHE TTC | PRO CCC | VAL GTG | THR ACC | ARG AGA | LEU CTT | LEU TTG | ASP GAC | 194 |
| 903 | THR ACC | ARG AGG | LEU TTG | VAL GTG | ASN AAT | GLN CAG | ASN AAT | ALA GCA | SER AGC | ARG AGG | TRP TGG | 205 |
| 936 | GLU GAA | SER AGT | PHE TTT | ASP GAT | VAL GTC | THR ACC | PRO CCC | ALA GCT | VAL GTG | MET ATG | ARG CGG | 216 |
| 969 | TRP TGG | THR ACT | ALA GCA | GLN CAG | GLY GGA | HIS CAC | ALA GCC | ASN AAC | HIS CAT | GLY GGA | PHE TTC | 227 |
| 1002 | VAL GTG | VAL GTG | GLU GAA | VAL GTG | ALA GCC | HIS CAC | LEU TTG | GLU GAG | GLU GAG | LYS AAA | GLN CAA | 238 |
| 1035 | GLY GGT | VAL GTC | SER TCC | LYS AAG | ARG AGA | HIS CAT | VAL GTT | ARG AGG | ILE ATA | SER AGC | ARG AGG | 249 |
| 1068 | SER TCT | LEU TTG | HIS CAC | GLN CAA | ASP GAT | GLU GAA | HIS CAC | SER AGC | TRP TGG | SER TCA | GLN CAG | 260 |
| 1101 | ILE ATA | ARG AGG | PRO CCA | LEU TTG | LEU CTA | VAL GTA | THR ACT | PHE TTT | GLY GGC | HIS CAT | ASP GAT | 271 |
| 1134 | GLY GGA | LYS AAA | GLY GGG | HIS CAT | PRO CCT | LEU CTC | HIS CAC | LYS AAA | ARG AGA | GLU GAA | LYS AAA | 282 |

FIG. 1c / 15

|      |     |     |     |     |     |     |     |     |     |     |     |     |
|------|-----|-----|-----|-----|-----|-----|-----|-----|-----|-----|-----|-----|
|      | ARG | GLN | ALA | LYS | HIS | LYS | GLN | ARG | LYS | ARG | LEU | 293 |
| 1167 | CGT | CAA | GCC | AAA | CAC | AAA | CAG | CGG | AAA | CGC | CTT |     |
|      | LYS | SER | SER | CYS | LYS | ARG | HIS | PRO | LEU | TYR | VAL | 304 |
| 1200 | AAG | TCC | AGC | TGT | AAG | AGA | CAC | CCT | TTG | TAC | GTG |     |
|      | ASP | PHE | SER | ASP | VAL | GLY | TRP | ASN | ASP | TRP | ILE | 315 |
| 1233 | GAC | TTC | AGT | GAC | GTG | GGG | TGG | AAT | GAC | TGG | ATT |     |
|      | VAL | ALA | PRO | PRO | GLY | TYR | HIS | ALA | PHE | TYR | CYS | 326 |
| 1266 | GTG | GCT | CCC | CCG | GGG | TAT | CAC | GCC | TTT | TAC | TGC |     |
|      | HIS | GLY | GLU | CYS | PRO | PHE | PRO | LEU | ALA | ASP | HIS | 337 |
| 1299 | CAC | GGA | GAA | TGC | CCT | TTT | CCT | CTG | GCT | GAT | CAT |     |
|      | LEU | ASN | SER | THR | ASN | HIS | ALA | ILE | VAL | GLN | THR | 348 |
| 1332 | CTG | AAC | TCC | ACT | AAT | CAT | GCC | ATT | GTT | CAG | ACG |     |
|      | LEU | VAL | ASN | SER | VAL | ASN | SER | LYS | ILE | PRO | LYS | 359 |
| 1365 | TTG | GTC | AAC | TCT | GTT | AAC | TCT | AAG | ATT | CCT | AAG |     |
|      | ALA | CYS | CYS | VAL | PRO | THR | GLU | LEU | SER | ALA | ILE | 370 |
| 1398 | GCA | TGC | TGT | GTC | CCG | ACA | GAA | CTC | AGT | GCT | ATC |     |
|      | SER | MET | LEU | TYR | LEU | ASP | GLU | ASN | GLU | LYS | VAL | 381 |
| 1431 | TCG | ATG | CTG | TAC | CTT | GAC | GAG | AAT | GAA | AAG | GTT |     |
|      | VAL | LEU | LYS | ASN | TYR | GLN | ASP | MET | VAL | VAL | GLU | 392 |
| 1464 | GTA | TTA | AAG | AAC | TAT | CAG | GAC | ATG | GTT | GTG | GAG |     |
|      | GLY | CYS | GLY | CYS | ARG |     |     |     |     |     |     | 397 |
| 1497 | GGT | TGT | GGG | TGT | CGC |     |     |     |     |     |     |     |

1512 TAG TACAGCAAAATTAAATACATAAATATATATATA

FIG. 2a / 15

```
1    GAAAGCGAGG GAGGGAAAGA GGAGGAAGGA AGATGCGAGA AGGCAGAGGA GGAGGGAGGG

61   AGGGAAGGAG CGCGGAGCCC GGCCCGGAAG CTAGGTGAGT GTGGCATCCG AGCTGAGGGA

121  CGCGAGCCTG AGACGCCGCT GCTGCTCCGG CTGAGTATCT AGCTTGTCTC CCCGATGGGA

181  TTCCCGTCCA AGCTATCTCG AGCCTGCAGC GCCACAGTCC CCGGCCCTCG CCCAGGTTCA

241  CTGCAACCGT TCAGAGGTCC CCAGGAGCTG CTGCTGGCGA GCCCGCTACT GCAGGGACCT

301  ATGGAGCCAT TCCGTAGTGC CATCCCGAGC AACGCACTGC TGCAGCTTCC CTGAGCCTTT

361  CCAGCAAGTT TGTTCAAGAT TGGCTGTCAA GAATCATGGA CTGTTATTAT ATGCCTTGTT
```

|       |            | Met | Ile | Pro | Gly | Asn | Arg | Met | Leu | 8   |
|-------|------------|-----|-----|-----|-----|-----|-----|-----|-----|-----|
| 421   | TTCTGTCAAG ACACC | ATG | ATT | CCT | GGT | AAC | CGA | ATG | CTG |     |

|     | Met | Val | Val | Leu | Leu | Cys | Gln | Val | Leu | Leu | Gly | 19 |
|-----|-----|-----|-----|-----|-----|-----|-----|-----|-----|-----|-----|----|
| 460 | ATG | GTC | GTT | TTA | TTA | TGC | CAA | GTC | CTG | CTA | GGA |    |

|     | Gly | Ala | Ser | His | Ala | Ser | Leu | Ile | Pro | Glu | Thr | 30 |
|-----|-----|-----|-----|-----|-----|-----|-----|-----|-----|-----|-----|----|
| 493 | GGC | GCG | AGC | CAT | GCT | AGT | TTG | ATA | CCT | GAG | ACG |    |

|     | Gly | Lys | Lys | Lys | Val | Ala | Glu | Ile | Gln | Gly | His | 41 |
|-----|-----|-----|-----|-----|-----|-----|-----|-----|-----|-----|-----|----|
| 526 | GGG | AAG | AAA | AAA | GTC | GCC | GAG | ATT | CAG | GGC | CAC |    |

|     | Ala | Gly | Gly | Arg | Arg | Ser | Gly | Gln | Ser | His | Glu | 52 |
|-----|-----|-----|-----|-----|-----|-----|-----|-----|-----|-----|-----|----|
| 559 | GCG | GGA | GGA | CGC | CGC | TCA | GGG | CAG | AGC | CAT | GAG |    |

|     | Leu | Leu | Arg | Asp | Phe | Glu | Ala | Thr | Leu | Leu | Gln | 63 |
|-----|-----|-----|-----|-----|-----|-----|-----|-----|-----|-----|-----|----|
| 592 | CTC | CTG | CGG | GAC | TTC | GAG | GCG | ACA | CTT | CTG | CAG |    |

|     | Met | Phe | Gly | Leu | Arg | Arg | Arg | Pro | Gln | Pro | Ser | 74 |
|-----|-----|-----|-----|-----|-----|-----|-----|-----|-----|-----|-----|----|
| 625 | ATG | TTT | GGG | CTG | CGC | CGC | CGC | CCG | CAG | CCT | AGC |    |

|     | Lys | Ser | Ala | Val | Ile | Pro | Asp | Tyr | Met | Arg | Asp | 85 |
|-----|-----|-----|-----|-----|-----|-----|-----|-----|-----|-----|-----|----|
| 658 | AAG | AGT | GCC | GTC | ATT | CCG | GAC | TAC | ATG | CGG | GAT |    |

|     | Leu | Tyr | Arg | Leu | Gln | Ser | Gly | Glu | Glu | Glu | Glu | 96 |
|-----|-----|-----|-----|-----|-----|-----|-----|-----|-----|-----|-----|----|
| 691 | CTT | TAC | CGG | CTT | CAG | TCT | GGG | GAG | GAG | GAG | GAA |    |

|     | Glu | Gln | Ile | His | Ser | Thr | Gly | Leu | Glu | Tyr | Pro | 107 |
|-----|-----|-----|-----|-----|-----|-----|-----|-----|-----|-----|-----|-----|
| 724 | GAG | CAG | ATC | CAC | AGC | ACT | GGT | CTT | GAG | TAT | CCT |     |

FIG. 2b / 15

| | | | | | | | | | | | | |
|---|---|---|---|---|---|---|---|---|---|---|---|---|
| 757 | Glu GAG | Arg CGC | Pro CCG | Ala GCC | Ser AGC | Arg CGG | Ala GCC | Asn AAC | Thr ACC | Val GTG | Arg AGG | 118 |
| 790 | Ser AGC | Phe TTC | His CAC | His CAC | Glu GAA | Glu GAA | His CAT | Leu CTG | Glu GAG | Asn AAC | Ile ATC | 129 |
| 823 | Pro CCA | Gly GGG | Thr ACC | Ser AGT | Glu GAA | Asn AAC | Ser TCT | Ala GCT | Phe TTT | Arg CGT | Phe TTC | 140 |
| 856 | Leu CTC | Phe TTT | Asn AAC | Leu CTC | Ser AGC | Ser AGC | Ile ATC | Pro CCT | Glu GAG | Asn AAC | Glu GAG | 151 |
| 889 | Ala GCG | Ile ATC | Ser TCC | Ser TCT | Ala GCA | Glu GAG | Leu CTT | Arg CGG | Leu CTC | Phe TTC | Arg CGG | 162 |
| 922 | Glu GAG | Gln CAG | Val GTG | Asp GAC | Gln CAG | Gly GGC | Pro CCT | Asp GAT | Trp TGG | Glu GAA | Arg AGG | 173 |
| 955 | Gly GGC | Phe TTC | His CAC | Arg CGT | Ile ATA | Asn AAC | Ile ATT | Tyr TAT | Glu GAG | Val GTT | Met ATG | 184 |
| 988 | Lys AAG | Pro CCC | Pro CCA | Ala GCA | Glu GAA | Val GTG | Val GTG | Pro CCT | Gly GGG | His CAC | Leu CTC | 195 |
| 1021 | Ile ATC | Thr ACA | Arg CGA | Leu CTA | Leu CTG | Asp GAC | Thr ACG | Arg AGA | Leu CTG | Val GTC | His CAC | 206 |
| 1054 | His CAC | Asn AAT | Val GTG | Thr ACA | Arg CGG | Trp TGG | Glu GAA | Thr ACT | Phe TTT | Asp GAT | Val GTG | 217 |
| 1087 | Ser AGC | Pro CCT | Ala GCG | Val GTC | Leu CTT | Arg CGC | Trp TGG | Thr ACC | Arg CGG | Glu GAG | Lys AAG | 228 |
| 1120 | Gln CAG | Pro CCA | Asn AAC | Tyr TAT | Gly GGG | Leu CTA | Ala GCC | Ile ATT | Glu GAG | Val GTG | Thr ACT | 239 |
| 1153 | His CAC | Leu CTC | His CAT | Gln CAG | Thr ACT | Arg CGG | Thr ACC | His CAC | Gln CAG | Gly GGC | Gln CAG | 250 |
| 1186 | His CAT | Val GTC | Arg AGG | Ile ATT | Ser AGC | Arg CGA | Ser TCG | Leu TTA | Pro CCT | Gln CAA | Gly GGG | 261 |
| 1219 | Ser AGT | Gly GGG | Asn AAT | Trp TGG | Ala GCC | Gln CAG | Leu CTC | Arg CGG | Pro CCC | Leu CTC | Leu CTG | 272 |

FIG. 2c / 15

```
        Val  Thr  Phe  Gly  His  Asp  Gly  Arg  Gly  His  Ala   283
1252    GTC  ACC  TTT  GGC  CAT  GAT  GGC  CGG  GGC  CAT  GCC

Leu  Thr  Arg  Arg  Arg  Arg  Ala  Lys  Arg  Ser  Pro   294
1285    TTG  ACC  CGA  CGC  CGG  AGG  GCC  AAG  CGT  AGC  CCT

Lys  His  His  Ser  Gln  Arg  Ala  Arg  Lys  Lys  Asn   305
1318    AAG  CAT  CAC  TCA  CAG  CGG  GCC  AGG  AAG  AAG  AAT

Lys  Asn  Cys  Arg  Arg  His  Ser  Leu  Tyr  Val  Asp   316
1351    AAG  AAC  TGC  CGG  CGC  CAC  TCG  CTC  TAT  GTG  GAC

Phe  Ser  Asp  Val  Gly  Trp  Asn  Asp  Trp  Ile  Val   327
1384    TTC  AGC  GAT  GTG  GGC  TGG  AAT  GAC  TGG  ATT  GTG

Ala  Pro  Pro  Gly  Tyr  Gln  Ala  Phe  Tyr  Cys  His   338
1417    GCC  CCA  CCA  GGC  TAC  CAG  GCC  TTC  TAC  TGC  CAT

Gly  Asp  Cys  Pro  Phe  Pro  Leu  Ala  Asp  His  Leu   349
1450    GGG  GAC  TGC  CCC  TTT  CCA  CTG  GCT  GAC  CAC  CTC

Asn  Ser  Thr  Asn  His  Ala  Ile  Val  Gln  Thr  Leu   360
1483    AAC  TCA  ACC  AAC  CAT  GCC  ATT  GTG  CAG  ACC  CTG

Val  Asn  Ser  Val  Asn  Ser  Ser  Ile  Pro  Lys  Ala   371
1516    GTC  AAT  TCT  GTC  AAT  TCC  AGT  ATC  CCC  AAA  GCC

Cys  Cys  Val  Pro  Thr  Glu  Leu  Ser  Ala  Ile  Ser   382
1549    TGT  TGT  GTG  CCC  ACT  GAA  CTG  AGT  GCC  ATC  TCC

Met  Leu  Tyr  Leu  Asp  Glu  Tyr  Asp  Lys  Val  Val   393
1582    ATG  CTG  TAC  CTG  GAT  GAG  TAT  GAT  AAG  GTG  GTA

Leu  Lys  Asn  Tyr  Gln  Glu  Met  Val  Val  Ala  Gly   404
1615    CTG  AAA  AAT  TAT  CAG  GAG  ATG  GTA  GTA  GAG  GGA

Cys  Gly  Cys  Arg                                      408
1648    TGT  GGG  TGC  CGC  TGA  GATCAGGCAGTCCTTGAGGATAGACAGATATAC

1696    ACACCACACACACACACCACATACACCCACACACACACGTTCCCATCCACTCACCCACACACTA

1759    CACAGACTGCTTCCTTATAGCTGGACTTTTATTTAAAAAAAAAAAAAAAAAAAATGGAAAAAAT
```

FIG. 2d / 15

1822 CCCTAAACATTCACCTTGACCTTATTTATGACTTTACGTGCAAATGTTTTGACCATATTGATC

1885 ATATATTTTGACAAAATATATTTATAACTACGTATTAAAAGAAAAAAATAAAATGAGTCATT

FIG. 3a / 15

```
1    CTGGTATATT TGTGCCTGCT GGAGGTGGAA TTAACAGTAA GAAGGAGAAA GGGATTGAAT
61   GGACTTACAG GAAGGATTTC AAGTAAATTC AGGGAAACAC ATTTACTTGA ATAGTACAAC
121  CTAGAGTATT ATTTTACACT AAGACGACAC AAAAGATGTT AAAGTTATCA CCAAGCTGCC
181  GGACAGATAT ATATTCCAAC ACCAAGGTGC AGATCAGCAT AGATCTGTGA TTCAGAAATC
241  AGGATTTGTT TTGGAAAGAG CTCAAGGGTT GAGAAGAACT CAAAAGCAAG TGAAGATTAC
301  TTTGGGAACT ACAGTTTATC AGAAGATCAA CTTTTGCTAA TTCAAATACC AAAGGCCTGA
361  TTATCATAAA TTCATATAGG AATGCATAGG TCATCTGATC AAATAATATT AGCCGTCTTC
421  TGCTACATCA ATGCAGCAAA AACTCTTAAC AACTGTGGAT AATTGGAAAT CTGAGTTTCA
481  GCTTTCTTAG AAATAACTAC TCTTGACATA TTCCAAAATA TTTAAAATAG GACAGGAAAA
541  TCGGTGAGGA TGTTGTGCTC AGAAATGTCA CTGTCATGAA AAATAGGTAA ATTTGTTTTT
601  TCAGCTACTG GGAAACTGTA CCTCCTAGAA CCTTAGGTTT TTTTTTTTTT AAGAGGACAA
```

|     |     |     |     |     |     |     |     |     | Met | His | Leu | Thr | 4 |
|-----|-----|-----|-----|-----|-----|-----|-----|-----|-----|-----|-----|-----|---|
| 661 | GAAGGACTAA | AAATATCAAC | TTTTGCTTTT | GGACAAAA | | | | | ATG | CAT | CTG | ACT | |

|     | Val | Phe | Leu | Leu | Lys | Gly | Ile | Val | Gly | Phe | Leu | 15 |
|-----|-----|-----|-----|-----|-----|-----|-----|-----|-----|-----|-----|----|
| 711 | GTA | TTT | TTA | CTT | AAG | GGT | ATT | GTG | GGT | TTC | CTC | |

|     | Trp | Ser | Cys | Trp | Val | Leu | Val | Gly | Tyr | Ala | Lys | 26 |
|-----|-----|-----|-----|-----|-----|-----|-----|-----|-----|-----|-----|----|
| 744 | TGG | AGC | TGC | TGG | GTT | CTA | GTG | GGT | TAT | GCA | AAA | |

|     | Gly | Gly | Leu | Gly | Asp | Asn | His | Val | His | Ser | Ser | 37 |
|-----|-----|-----|-----|-----|-----|-----|-----|-----|-----|-----|-----|----|
| 777 | GGA | GGT | TTG | GGA | GAC | AAT | CAT | GTT | CAC | TCC | AGT | |

|     | Phe | Ile | Tyr | Arg | Arg | Leu | Arg | Asn | His | Glu | Arg | 48 |
|-----|-----|-----|-----|-----|-----|-----|-----|-----|-----|-----|-----|----|
| 810 | TTT | ATT | TAT | AGA | AGA | CTA | CGG | AAC | CAC | GAA | AGA | |

|     | Arg | Glu | Ile | Gln | Arg | Glu | Ile | Leu | Ser | Ile | Leu | 59 |
|-----|-----|-----|-----|-----|-----|-----|-----|-----|-----|-----|-----|----|
| 843 | CGG | GAA | ATA | CAA | AGG | GAA | ATT | CTC | TCT | ATC | TTG | |

|     | Gly | Leu | Pro | His | Arg | Pro | Arg | Pro | Phe | Ser | Pro | 70 |
|-----|-----|-----|-----|-----|-----|-----|-----|-----|-----|-----|-----|----|
| 876 | GGT | TTG | CCT | CAC | AGA | CCC | AGA | CCA | TTT | TCA | CCT | |

|     | Gly | Lys | Gln | Ala | Ser | Ser | Ala | Pro | Leu | Phe | Met | 81 |
|-----|-----|-----|-----|-----|-----|-----|-----|-----|-----|-----|-----|----|
| 909 | GGA | AAA | CAA | GCG | TCC | TCT | GCA | CCT | CTC | TTT | ATG | |

|     | Leu | Asp | Leu | Tyr | Asn | Ala | Met | Thr | Asn | Glu | Glu | 92 |
|-----|-----|-----|-----|-----|-----|-----|-----|-----|-----|-----|-----|----|
| 942 | CTG | GAT | CTC | TAC | AAT | GCC | ATG | ACC | AAT | GAA | GAA | |

FIG. 3b / 15

|      |     |     |     |     |     |     |     |     |     |     |     |
|------|-----|-----|-----|-----|-----|-----|-----|-----|-----|-----|-----|
|      | Asn | Pro | Glu | Glu | Ser | Glu | Tyr | Ser | Val | Arg | Ala | 103 |
| 975  | AAT | CCT | GAA | GAG | TCG | GAG | TAC | TCA | GTA | AGG | GCA |     |
|      | Ser | Leu | Ala | Glu | Glu | Thr | Arg | Gly | Ala | Arg | Lys | 114 |
| 1008 | TCC | TTG | GCA | GAA | GAG | ACC | AGA | GGG | GCA | AGA | AAG |     |
|      | Gly | Tyr | Pro | Ala | Ser | Pro | Asn | Gly | Tyr | Pro | Arg | 125 |
| 1041 | GGA | TAC | CCA | GCC | TCT | CCC | AAT | GGG | TAT | CCT | CGT |     |
|      | Arg | Ile | Gln | Leu | Ser | Arg | Thr | Thr | Pro | Leu | Thr | 136 |
| 1074 | CGC | ATA | CAG | TTA | TCT | CGG | ACG | ACT | CCT | CTG | ACC |     |
|      | Thr | Gln | Ser | Pro | Pro | Leu | Ala | Ser | Leu | His | Asp | 147 |
| 1107 | ACC | CAG | AGT | CCT | CCT | CTA | GCC | AGC | CTC | CAT | GAT |     |
|      | Thr | Asn | Phe | Leu | Asn | Asp | Ala | Asp | Met | Val | Met | 158 |
| 1140 | ACC | AAC | TTT | CTG | AAT | GAT | GCT | GAC | ATG | GTC | ATG |     |
|      | Ser | Phe | Val | Asn | Leu | Val | Glu | Arg | Asp | Lys | Asp | 169 |
| 1173 | AGC | TTT | GTC | AAC | TTA | GTT | GAA | AGA | GAC | AAG | GAT |     |
|      | Phe | Ser | His | Gln | Arg | Arg | His | Tyr | Lys | Glu | Phe | 180 |
| 1206 | TTT | TCT | CAC | CAG | CGA | AGG | CAT | TAC | AAA | GAA | TTT |     |
|      | Arg | Phe | Asp | Leu | Thr | Gln | Ile | Pro | His | Gly | Glu | 191 |
| 1239 | CGA | TTT | GAT | CTT | ACC | CAA | ATT | CCT | CAT | GGA | GAG |     |
|      | Ala | Val | Thr | Ala | Ala | Glu | Phe | Arg | Ile | Tyr | Lys | 202 |
| 1272 | GCA | GTG | ACA | GCA | GCT | GAA | TTC | CGG | ATA | TAC | AAG |     |
|      | Asp | Arg | Ser | Asn | Asn | Arg | Phe | Glu | Asn | Glu | Thr | 213 |
| 1305 | GAC | CGG | AGC | AAC | AAC | CGA | TTT | GAA | AAT | GAA | ACA |     |
|      | Ile | Lys | Ile | Ser | Ile | Tyr | Gln | Ile | Ile | Lys | Glu | 224 |
| 1338 | ATT | AAG | ATT | AGC | ATA | TAT | CAA | ATC | ATC | AAG | GAA |     |
|      | Tyr | Thr | Asn | Arg | Asp | Ala | Asp | Leu | Phe | Leu | Leu | 235 |
| 1371 | TAC | ACA | AAT | AGG | GAT | GCA | GAT | CTG | TTC | TTG | TTA |     |
|      | Asp | Thr | Arg | Lys | Ala | Gln | Ala | Leu | Asp | Val | Gly | 246 |
| 1404 | GAC | ACA | AGA | AAG | GCC | CAA | GCT | TTA | GAT | GTG | GGT |     |
|      | Trp | Leu | Val | Phe | Asp | Ile | Thr | Val | Thr | Ser | Asn | 257 |
| 1437 | TGG | CTT | GTC | TTT | GAT | ATC | ACT | GTG | ACC | AGC | AAT |     |

FIG. 3c / 15

|      |     |     |     |     |     |     |     |     |     |     |     |     |
|------|-----|-----|-----|-----|-----|-----|-----|-----|-----|-----|-----|-----|
|      | His | Trp | Val | Ile | Asn | Pro | Gln | Asn | Asn | Leu | Gly | 268 |
| 1470 | CAT | TGG | GTG | ATT | AAT | CCC | CAG | AAT | AAT | TTG | GGC |     |
|      | Leu | Gln | Leu | Cys | Ala | Glu | Thr | Gly | Asp | Gly | Arg | 279 |
| 1503 | TTA | CAG | CTC | TGT | GCA | GAA | ACA | GGG | GAT | GGA | CGC |     |
|      | Ser | Ile | Asn | Val | Lys | Ser | Ala | Gly | Leu | Val | Gly | 290 |
| 1536 | AGT | ATC | AAC | GTA | AAA | TCT | GCT | GGT | CTT | GTG | GGA |     |
|      | Arg | Gln | Gly | Pro | Gln | Ser | Lys | Gln | Pro | Phe | Met | 301 |
| 1569 | AGA | CAG | GGA | CCT | CAG | TCA | AAA | CAA | CCA | TTC | ATG |     |
|      | Val | Ala | Phe | Phe | Lys | Ala | Ser | Glu | Val | Leu | Leu | 312 |
| 1602 | GTG | GCC | TTC | TTC | AAG | GCG | AGT | GAG | GTA | CTT | CTT |     |
|      | Arg | Ser | Val | Arg | Ala | Ala | Asn | Lys | Arg | Lys | Asn | 323 |
| 1635 | CGA | TCC | GTG | AGA | GCA | GCC | AAC | AAA | CGA | AAA | AAT |     |
|      | Gln | Asn | Arg | Asn | Lys | Ser | Ser | Ser | His | Gln | Asp | 334 |
| 1668 | CAA | AAC | CGC | AAT | AAA | TCC | AGC | TCT | CAT | CAG | GAC |     |
|      | Ser | Ser | Arg | Met | Ser | Ser | Val | Gly | Asp | Tyr | Asn | 345 |
| 1701 | TCC | TCC | AGA | ATG | TCC | AGT | GTT | GGA | GAT | TAT | AAC |     |
|      | Thr | Ser | Glu | Gln | Lys | Gln | Ala | Cys | Lys | Lys | His | 356 |
| 1734 | ACA | AGT | GAG | CAA | AAA | CAA | GCC | TGT | AAG | AAG | CAC |     |
|      | Glu | Leu | Tyr | Val | Ser | Phe | Arg | Asp | Leu | Gly | Trp | 367 |
| 1767 | GAA | CTC | TAT | GTG | AGC | TTC | CGG | GAT | CTG | GGA | TGG |     |
|      | Gln | Asp | Trp | Ile | Ile | Ala | Pro | Glu | Gly | Tyr | Ala | 378 |
| 1800 | CAG | GAC | TGG | ATT | ATA | GCA | CCA | GAA | GGA | TAC | GCT |     |
|      | Ala | Phe | Tyr | Cys | Asp | Gly | Glu | Cys | Ser | Phe | Pro | 389 |
| 1833 | GCA | TTT | TAT | TGT | GAT | GGA | GAA | TGT | TCT | TTT | CCA |     |
|      | Leu | Asn | Ala | His | Met | Asn | Ala | Thr | Asn | His | Ala | 400 |
| 1866 | CTT | AAC | GCC | CAT | ATG | AAT | GCC | ACC | AAC | CAC | GCT |     |
|      | Ile | Val | Gln | Thr | Leu | Val | His | Leu | Met | Phe | Pro | 411 |
| 1899 | ATA | GTT | CAG | ACT | CTG | GTT | CAT | CTG | ATG | TTT | CCT |     |
|      | Asp | His | Val | Pro | Lys | Pro | Cys | Cys | Ala | Pro | Thr | 422 |
| 1932 | GAC | CAC | GTA | CCA | AAG | CCT | TGT | TGT | GCT | CCA | ACC |     |

FIG. 3d / 15

```
          Lys   Leu   Asn   Ala   Ile   Ser   Val   Leu   Tyr   Phe   Asp   433
1965      AAA   TTA   AAT   GCC   ATC   TCT   GTT   CTG   TAC   TTT   GAT

Asp   Ser   Ser   Asn   Val   Ile   Leu   Lys   Lys   Tyr   Arg   444
1998      GAC   AGC   TCC   AAT   GTC   ATT   TTG   AAA   AAA   TAT   AGA

Asn   Met   Val   Val   Arg   Ser   Cys   Gly   Cys   His         454
2031      AAT   ATG   GTA   GTA   CGC   TCA   TGT   GGC   TGC   CAC   TAA

2064      TATTAAATAATATTGATAATAACAAAAAGATCTGTATTAAGGTTTATGGCTGCAATAAAAAGCA

2128      TACTTTCAGACAAACAGAAAAAAAAA
```

FIG. 4a / 15

```
1    GGGCGCAGCG GGGCCCGTCT GCAGCAAGTG ACCGACGGCC GGGACGGCCG CCTGCCCCCT
61   CTGCCACCTG GGGCGGTGCG GGCCCGGAGC CCGGAGCCCG GGTAGCGCGT AGAGCCGGCG
```

|     |     | Met | His | Val | Arg | Ser | Leu | Arg | Ala | Ala | Ala |     |
|-----|-----|-----|-----|-----|-----|-----|-----|-----|-----|-----|-----|-----|
| 121 | CG  | ATG | CAC | GTG | CGC | TCA | CTG | CGA | GCT | GCG | GCG | 10  |

|     | Pro | His | Ser | Phe | Val | Ala | Leu | Trp | Ala | Pro | Leu |     |
|-----|-----|-----|-----|-----|-----|-----|-----|-----|-----|-----|-----|-----|
| 153 | CCG | CAC | AGC | TTC | GTG | GCG | CTC | TGG | GCA | CCC | CTG | 21  |

|     | Phe | Leu | Leu | Arg | Ser | Ala | Leu | Ala | Asp | Phe | Ser |     |
|-----|-----|-----|-----|-----|-----|-----|-----|-----|-----|-----|-----|-----|
| 186 | TTC | CTG | CTG | CGC | TCC | GCC | CTG | GCC | GAC | TTC | AGC | 32  |

|     | Leu | Asp | Asn | Glu | Val | His | Ser | Ser | Phe | Ile | His |     |
|-----|-----|-----|-----|-----|-----|-----|-----|-----|-----|-----|-----|-----|
| 219 | CTG | GAC | AAC | GAG | GTG | CAC | TCG | AGC | TTC | ATC | CAC | 43  |

|     | Arg | Arg | Leu | Arg | Ser | Gln | Glu | Arg | Arg | Glu | Met |     |
|-----|-----|-----|-----|-----|-----|-----|-----|-----|-----|-----|-----|-----|
| 252 | CGG | CGC | CTC | CGC | AGC | CAG | GAG | CGG | CGG | GAG | ATG | 54  |

|     | Gln | Arg | Glu | Ile | Leu | Ser | Ile | Leu | Gly | Leu | Pro |     |
|-----|-----|-----|-----|-----|-----|-----|-----|-----|-----|-----|-----|-----|
| 285 | CAG | CGC | GAG | ATC | CTC | TCC | ATT | TTG | GGC | TTG | CCC | 65  |

|     | His | Arg | Pro | Arg | Pro | His | Leu | Gln | Gly | Lys | His |     |
|-----|-----|-----|-----|-----|-----|-----|-----|-----|-----|-----|-----|-----|
| 318 | CAC | CGC | CCG | CGC | CCG | CAC | CTC | CAG | GGC | AAG | CAC | 76  |

|     | Asn | Ser | Ala | Pro | Met | Phe | Met | Leu | Asp | Leu | Tyr |     |
|-----|-----|-----|-----|-----|-----|-----|-----|-----|-----|-----|-----|-----|
| 351 | AAC | TCG | GCA | CCC | ATG | TTC | ATG | CTG | GAC | CTG | TAC | 87  |

|     | Asn | Ala | Met | Ala | Val | Glu | Glu | Gly | Gly | Gly | Pro |     |
|-----|-----|-----|-----|-----|-----|-----|-----|-----|-----|-----|-----|-----|
| 384 | AAC | GCC | ATG | GCG | GTG | GAG | GAG | GGC | GGG | GGG | CCC | 98  |

|     | Gly | Gly | Gln | Gly | Phe | Ser | Tyr | Pro | Tyr | Lys | Ala |     |
|-----|-----|-----|-----|-----|-----|-----|-----|-----|-----|-----|-----|-----|
| 417 | GGC | GGC | CAG | GGC | TTC | TCC | TAC | CCC | TAC | AAG | GCC | 109 |

|     | Val | Phe | Ser | Thr | Gln | Gly | Pro | Pro | Leu | Ala | Ser |     |
|-----|-----|-----|-----|-----|-----|-----|-----|-----|-----|-----|-----|-----|
| 450 | GTC | TTC | AGT | ACC | CAG | GGC | CCC | CCT | CTG | GCC | AGC | 120 |

|     | Leu | Gln | Asp | Ser | His | Phe | Leu | Thr | Asp | Ala | Asp |     |
|-----|-----|-----|-----|-----|-----|-----|-----|-----|-----|-----|-----|-----|
| 483 | CTG | CAA | GAT | AGC | CAT | TTC | CTC | ACC | GAC | GCC | GAC | 131 |

|     | Met | Val | Met | Ser | Phe | Val | Asn | Leu | Val | Glu | His |     |
|-----|-----|-----|-----|-----|-----|-----|-----|-----|-----|-----|-----|-----|
| 516 | ATG | GTC | ATG | AGC | TTC | GTC | AAC | CTC | GTG | GAA | CAT | 142 |

|     | Asp | Lys | Glu | Phe | Phe | His | Pro | Arg | Tyr | His | His |     |
|-----|-----|-----|-----|-----|-----|-----|-----|-----|-----|-----|-----|-----|
| 549 | GAC | AAG | GAA | TTC | TTC | CAC | CCA | CGC | TAC | CAC | CAT | 153 |

FIG. 4b / 15

|      | | | | | | | | | | | |     |
|------|---|---|---|---|---|---|---|---|---|---|---|-----|
|      | Arg | Glu | Phe | Arg | Phe | Asp | Leu | Ser | Lys | Ile | Pro | 164 |
| 582  | CGA | GAG | TTC | CGG | TTT | GAT | CTT | TCC | AAG | ATC | CCA |     |
|      | Glu | Gly | Glu | Ala | Val | Thr | Ala | Ala | Glu | Phe | Arg | 175 |
| 615  | GAA | GGG | GAA | GCT | GTC | ACG | GCA | GCC | GAA | TTC | CGG |     |
|      | Ile | Tyr | Lys | Asp | Tyr | Ile | Arg | Glu | Arg | Phe | Asp | 186 |
| 648  | ATC | TAC | AAG | GAC | TAC | ATC | CGG | GAA | CGC | TTC | GAC |     |
|      | Asn | Glu | Thr | Phe | Arg | Ile | Ser | Val | Tyr | Gln | Val | 197 |
| 681  | AAT | GAG | ACG | TTC | CGG | ATC | AGC | GTT | TAT | CAG | GTG |     |
|      | Leu | Gln | Glu | His | Leu | Gly | Arg | Glu | Ser | Asp | Leu | 208 |
| 714  | CTC | CAG | GAG | CAC | TTG | GGC | AGG | GAA | TCG | GAT | CTC |     |
|      | Phe | Leu | Leu | Asp | Ser | Arg | Thr | Leu | Trp | Ala | Ser | 219 |
| 747  | TTC | CTG | CTC | GAC | AGC | CGT | ACC | CTC | TGG | GCC | TCG |     |
|      | Glu | Glu | Gly | Trp | Leu | Val | Phe | Asp | Ile | Thr | Ala | 230 |
| 780  | GAG | GAG | GGC | TGG | CTG | GTG | TTT | GAC | ATC | ACA | GCC |     |
|      | Thr | Ser | Asn | His | Trp | Val | Val | Asn | Pro | Arg | His | 241 |
| 813  | ACC | AGC | AAC | CAC | TGG | GTG | GTC | AAT | CCG | CGG | CAC |     |
|      | Asn | Leu | Gly | Leu | Gln | Leu | Ser | Val | Glu | Thr | Leu | 252 |
| 846  | AAC | CTG | GGC | CTG | CAG | CTC | TCG | GTG | GAG | ACG | CTG |     |
|      | Asp | Gly | Gln | Ser | Ile | Asn | Pro | Lys | Leu | Ala | Gly | 263 |
| 879  | GAT | GGG | CAG | AGC | ATC | AAC | CCC | AAG | TTG | GCG | GGC |     |
|      | Leu | Ile | Gly | Arg | His | Gly | Pro | Gln | Asn | Lys | Gln | 274 |
| 912  | CTG | ATT | GGG | CGG | CAC | GGG | CCC | CAG | AAC | AAG | CAG |     |
|      | Pro | Phe | Met | Val | Ala | Phe | Phe | Lys | Ala | Thr | Glu | 285 |
| 945  | CCC | TTC | ATG | GTG | GCT | TTC | TTC | AAG | GCC | ACG | GAG |     |
|      | Val | His | Phe | Arg | Ser | Ile | Arg | Ser | Thr | Gly | Ser | 296 |
| 978  | GTC | CAC | TTC | CGC | AGC | ATC | CGG | TCC | ACG | GGG | AGC |     |
|      | Lys | Gln | Arg | Ser | Gln | Asn | Arg | Ser | Lys | Thr | Pro | 307 |
| 1011 | AAA | CAG | CGC | AGC | CAG | AAC | CGC | TCC | AAG | ACG | CCC |     |
|      | Lys | Asn | Gln | Glu | Ala | Leu | Arg | Met | Ala | Asn | Val | 318 |
| 1044 | AAG | AAC | CAG | GAA | GCC | CTG | CGG | ATG | GCC | AAC | GTG |     |

FIG. 4c / 15

|      | | | | | | | | | | | |     |
|------|---|---|---|---|---|---|---|---|---|---|---|-----|
|      | Ala | Glu | Asn | Ser | Ser | Ser | Asp | Gln | Arg | Gln | Ala | 329 |
| 1077 | GCA | GAG | AAC | AGC | AGC | AGC | GAC | CAG | AGG | CAG | GCC |     |
|      | Cys | Lys | Lys | His | Glu | Leu | Tyr | Val | Ser | Phe | Arg | 351 |
| 1110 | TGT | AAG | AAG | CAC | GAG | CTG | TAT | GTC | AGC | TTC | CGA |     |
|      | Asp | Leu | Gly | Trp | Gln | Asp | Trp | Ile | Ile | Ala | Pro | 362 |
| 1143 | GAC | CTG | GGC | TGG | CAG | GAC | TGG | ATC | ATC | GCG | CCT |     |
|      | Glu | Gly | Tyr | Ala | Ala | Tyr | Tyr | Cys | Glu | Gly | Glu | 373 |
| 1176 | GAA | GGC | TAC | GCC | GCC | TAC | TAC | TGT | GAG | GGG | GAG |     |
|      | Cys | Ala | Phe | Pro | Leu | Asn | Ser | Tyr | Met | Asn | Ala | 384 |
| 1209 | TGT | GCC | TTC | CCT | CTG | AAC | TCC | TAC | ATG | AAC | GCC |     |
|      | Thr | Asn | His | Ala | Ile | Val | Gln | Thr | Leu | Val | His | 395 |
| 1242 | ACC | AAC | CAC | GCC | ATC | GTG | CAG | ACG | CTG | GTC | CAC |     |
|      | Phe | Ile | Asn | Pro | Glu | Thr | Val | Pro | Lys | Pro | Cys | 406 |
| 1275 | TTC | ATC | AAC | CCG | GAA | ACG | GTG | CCC | AAG | CCC | TGC |     |
|      | Cys | Ala | Pro | Thr | Gln | Leu | Asn | Ala | Ile | Ser | Val | 417 |
| 1308 | TGT | GCG | CCC | ACG | CAG | CTC | AAT | GCC | ATC | TCC | GTC |     |
|      | Leu | Tyr | Phe | Asp | Asp | Ser | Ser | Asn | Val | Ile | Leu | 428 |
| 1341 | CTC | TAC | TTC | GAT | GAC | AGC | TCC | AAC | GTC | ATC | CTG |     |
|      | Lys | Lys | Tyr | Arg | Asn | Met | Val | Val | Arg | Ala | Cys | 439 |
| 1374 | AAG | AAA | TAC | AGA | AAC | ATG | GTG | GTC | CGG | GCC | TGT |     |
|      | Gly | Cys | His | | | | | | | | | 442 |
| 1407 | GGC | TGC | CAC | TAG | | | | | | | |     |

1419 CTCCTCCGAGAATTCAGACCCTTTGGGGCCAAGTTTTTCTGGATCCTCCATTGCTCGCCTTGGC

1483 CAGGAACCAGCAGACCAACTGCCTTTTGTGAGACCTTCCCCTCCCTATCCCCAACTTTAAAGGT

1547 GTGAGAGTATTAGGAAACATGAGCAGCATATGGCTTTTGATCAGTTTTTCAGTGGCAGCATCCA

1611 ATGAACAAGATCCTACAAGCTGTGCAGGCAAAACCTAGCAGGAAAAAAAAACAACGCATAAAGA

1675 AAAATGGCCGGGCCAGGTCATTGGCTGGGAAGTCTCAGCCATGCACGGACTCGTTTCCAGAGGT

FIG. 4d / 15

1739 AATTATGAGCGCCTACCAGCCAGGCCACCCAGCCGTGGGAGGAAGGGGGCGTGGCAAGGGGTGG

1803 GCACATTGGTGTCTGTGCGAAAGGAAAATTGACCCGGAAGTTCCTGTAATAAATGTCACAATAA

1867 AACGAATGAATG

METHOD FOR TREATING GLAUCOMA COMPRISING ADMINISTERING TO A PATIENT IN NEED THEREOF A COMPOSITION COMPRISING AN ANTIBODY AGAINST GREMLIN

The present application is a continuation of U.S. patent application Ser. No. 10/286,152 filed Oct. 31, 2002, which issued as U.S. Pat. No. 7,405,192, and which claims benefit to Provisional Application Ser. No. 60/334,852 filed Oct. 31, 2001.

BACKGROUND OF THE INVENTION

1. Field of the Invention

The present invention discloses methods and reagents for diagnosing and treating glaucoma and related disorders.

2. Description of the Related Art

"Glaucomas" are a group of debilitating eye diseases that are the leading cause of irreversible blindness in the United States and other developed nations. Primary Open Angle Glaucoma ("POAG"), the most common form of glaucoma, is characterized by the degeneration of the trabecular meshwork, leading to obstruction of the normal ability of aqueous humor to leave the eye without closure of the space (e.g., the "angle") between the iris and cornea (Vaughan, D. et al., (1992)). A characteristic of such obstruction in this disease is an increased intraocular pressure ("IOP"), resulting in progressive visual loss and blindness if not treated appropriately and in a timely fashion. The disease is estimated to affect between 0.4% and 3.3% of all adults over 40 years old (Leske, M. C. et al. (1986); Bengtsson, B. (1989); Strong, N. P. (1992)). Moreover, the prevalence of the disease rises with age to over 6% of those 75 years or older (Strong, N. P., (1992)).

Because increased IOP is a readily measurable characteristic of glaucoma, the diagnosis of the disease is largely screened for by measuring intraocular pressure (tonometry) (Strong, N. P. (1992); Greve, M. et al. (1993)). Unfortunately, because glaucomatous and normal pressure ranges overlap, such methods are of limited value unless multiple readings are obtained (Hitchings, R. A., (1993); Tuck, M. W. et al. (1993); Vaughan, D. et al., (1992); Vernon, S. A., (1993)). For this reason, additional methods, such as direct examination of the optic disk and determination of the extent of a patient's visual field loss are often conducted to improve the accuracy of diagnosis (Greve, M. et al., (1993)).

Glaucoma affects three separate tissues in the eye. The elevated IOP associated with POAG is due to morphological and biochemical changes in the trabecular meshwork (TM), a tissue located at the angle between the cornea and iris. Most of the nutritive aqueous humor exits the anterior segment of the eye through the TM. The progressive loss of TM cells and the build-up of extracellular debris in the TM of glaucomatous eyes leads to increased resistance to aqueous outflow (Lutjen-Drecoll and Rohen 1996; Rohen 1983; Rohen et al. 1993; Grierson and Calthorpe 1988), thereby raising IOP. Elevated IOP, as well as other factors such as ischemia, cause degenerative changes in the optic nerve head (ONH) leading to progressive "cupping" of the ONH (Varma and Minckler 1996; Hernandez and Gong 1996; Hernandez et al. 1990; Hernandez and Pena 1997; Morrison al. 1990) and loss of retinal ganglion cells (Quigley et al. 2000; Quigley 1999; Quigley et al. 1995; Kerrigan et al. 1997) and axons. The detailed molecular mechanisms responsible for glaucomatous damage to the TM, ONH, and the retinal ganglion cells are unknown.

Current glaucoma therapy is directed to lowering IOP, a major risk factor for the development and progression of glaucoma. These therapies lower IOP, but they do not directly address the pathogenic mechanisms, and the disease continues to progress. At least half of patients with glaucoma are undiagnosed, and by the time patients are diagnosed with glaucoma, they have already lost approximately 40% of their retinal ganglion cells. Therefore, methods for earlier detection and diagnosis of glaucoma are needed.

In view of the importance of glaucoma, and the at least partial inadequacies of prior methods of diagnosis, it would be desirable to have an improved, more accurate method for diagnosing glaucoma in its early stages. In addition, it would be desirable to have new therapeutic agents that address glaucomatous pathogenic mechanisms.

SUMMARY OF THE INVENTION

The present invention overcomes these and other drawbacks of the prior art by providing methods and kits for the early diagnosis of glaucoma, for treating glaucoma, and for the identification of compounds useful in the treatment of glaucoma.

In certain specific embodiments, the invention provides a method for diagnosing glaucoma in a sample obtained from a cell or bodily fluid by detecting altered expression of a bone morphogenic protein family member gene. The method generally includes the steps of:
 a) obtaining a tissue or fluid sample from a patient suspected of having glaucoma;
 b) extracting DNA from said sample;
 c) obtaining a plurality of PCR primers, wherein said primers each comprise a sequence consisting of from 18 to 1547 contiguous nucleotides from SEQ ID NO:1, SEQ ID NO:3, SEQ ID NO:5, SEQ ID NO:7, SEQ ID NO: 37, SEQ ID NO:39, SEQ ID NO:41, SEQ ID NO:43, SEQ ID NO:45, SEQ ID NO:47, or SEQ ID NO:53;
 d) amplifying regions of the extracted DNA using said primers to obtain a PCR product;
 e) resolving the PCR product; and
 f) identifying differences between the sequence of the PCR product and the normal gene sequence;
 where a difference between the amplified sequence and the normal gene sequence is diagnostic of glaucoma.

In general, the methods of the invention may include obtaining a sample from an individual and extracting DNA from said sample. Select PCR primers for specific members of the BMP gene family are then used to amplify relevant regions of the extracted gene to obtain a PCR product. The PCR product is resolved by a technique that effectively identifies DNA sequence differences between the normal and mutated form of the specific BMP family gene being evaluated (the extracted DNA). Identified differences between the sequences are indicative of glaucoma.

The tissue or fluid sample for use in the methods of the invention may be blood or buccal cells.

Typically, the primer sequences will have a length of between about 10, 15 or 18 nucleotides to about 20, or to about 30 nucleotides. Longer sequences, e.g., 40, 50, 80, 90, 95, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe, as described by Lathe (1985), which reference is specifically incorporated herein by reference for this purpose. Preferably, the nucleotide sequence will consist of from 20 to 100 contiguous nucleotides of SEQ ID NO:1, SEQ ID NO:3, SEQ ID NO:5, SEQ ID NO:7, SEQ ID NO:37, SEQ ID NO:39, SEQ ID NO:41, SEQ ID NO:43, SEQ ID NO:45, SEQ ID NO:47, or SEQ ID NO:53. It is also contemplated that the primer sequences may consist of sequences of at least 10, 15 or 18 contiguous nucleotides from the sequences of BMP receptor genes and from BMP-associated proteins, the sequences of which are known.

Nucleic acid molecules having stretches of 10, 18, 20, 30, 50, 60, 65 or even up to and including 100 nucleotides or so, complementary to any one of SEQ ID NO: 1, SEQ ID NO:3, SEQ ID NO:5, SEQ ID NO:7, SEQ ID NO:37, SEQ ID NO:39, SEQ ID NO:41, SEQ ID NO:43, SEQ ID NO:45, SEQ ID NO:47, or SEQ ID NO:53, have utility as hybridization probes. Primers or probes having a nucleotide length of about 18 nucleotides are recognized by those of skill in the art to provide highly specific hybridization to a target sequence. The total size of the fragment, as well as the size of the complementary stretches, will ultimately depend on the intended use of application of the particular nucleic acid segment. Smaller fragments will generally find use in hybridization embodiments, wherein the length of the complementary region may be varied, such as between about 10, 18, 20 or 30 and about 50, 60, 70, 80, 80 or 100 nucleotides, or even full length according to the complementary sequences one wishes to detect.

In specifically preferred embodiments, the primers will consist of contiguous sequences from SEQ ID NO: 1, SEQ ID NO:3, SEQ ID NO:5, SEQ ID NO:7, SEQ ID NO:37, SEQ ID NO:39, SEQ ID NO:41, SEQ ID NO:43, SEQ ID NO:45, SEQ ID NO:47, or SEQ ID NO:53. In other preferred embodiments, the primers will consist of contiguous sequences from BMP receptor genes (disclosed in ten Dijke et al. 1993; Astrom et al. 1999; Nohno et al. 1995, all incorporated herein by reference) or from BMP-associated genes, such as chordin (NCBI NM_029130), gremlin (Murphy et al. 1999; McMahon et al. 2000), follistatin (NCBI NM_003892) or bambi (NCBI NM_005791). Most preferably, the primers will consist of contiguous sequence from SEQ ID NO:3. In certain aspects, at least some of the primers may further include a detectable label.

In other embodiments, the invention provides a method for treating glaucoma by administering to a patient in need thereof a composition comprising a sequence consisting of at least one compound selected from the group consisting of a BMP2 agonist, a BMP4 agonist, a BMP5 agonist, a BMP7 agonist, a Smad 1/5 agonist, a chordin antagonist, a gremlin antagonist and a follistatin antagonist.

In additional aspects, the present invention provides a method for identifying a therapeutic agent for the treatment of glaucoma. Therapeutic agents may be identified, for example, by:

a) obtaining a first composition comprising a population of recombinant cells expressing BMP-2A, BMP4, BMP-5, or BMP7;
b) obtaining a candidate substance;
c) incubating said composition and said candidate substance;

testing said composition for its ability to turn on BMP-induced Smad signaling pathways and/or BMP-regulated gene expression; and identifying a candidate substance that inhibits, or stimulates, these downstream effects of BMP.

Another aspect of the invention are diagnostic kits containing sequences of the present invention and suitable reagents such as a detectable label linked to a protein, peptide or the antibody itself. Alternatively, the detectable label may be linked to a second sequence which selectively hybridizes to a sequence of the invention.

Related embodiments include therapeutic kits which include pharmaceutically-acceptable formulations of either the nucleic acid sequences or peptide or protein sequences disclosed herein. Such kits are useful in the detection of altered expression of the BMP genes and proteins in clinical samples for the diagnosis of glaucoma.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Nucleotide (SEQ ID NO: 1) and amino acid (SEQ ID NO: 2) sequence of BMP2A.

FIG. 2. Nucleotide (SEQ ID NO: 3) and amino acid (SEQ ID NO: 4) sequence of BMP4.

FIG. 3. Nucleotide (SEQ ID NO: 5) and amino acid (SEQ ID NO: 6) sequence of BMP5.

FIG. 4. Nucleotide (SEQ ID NO: 7) and amino acid (SEQ ID NO: 8) sequence of BMP7.

DETAILED DESCRIPTION PREFERRED EMBODIMENTS

Figure 5:
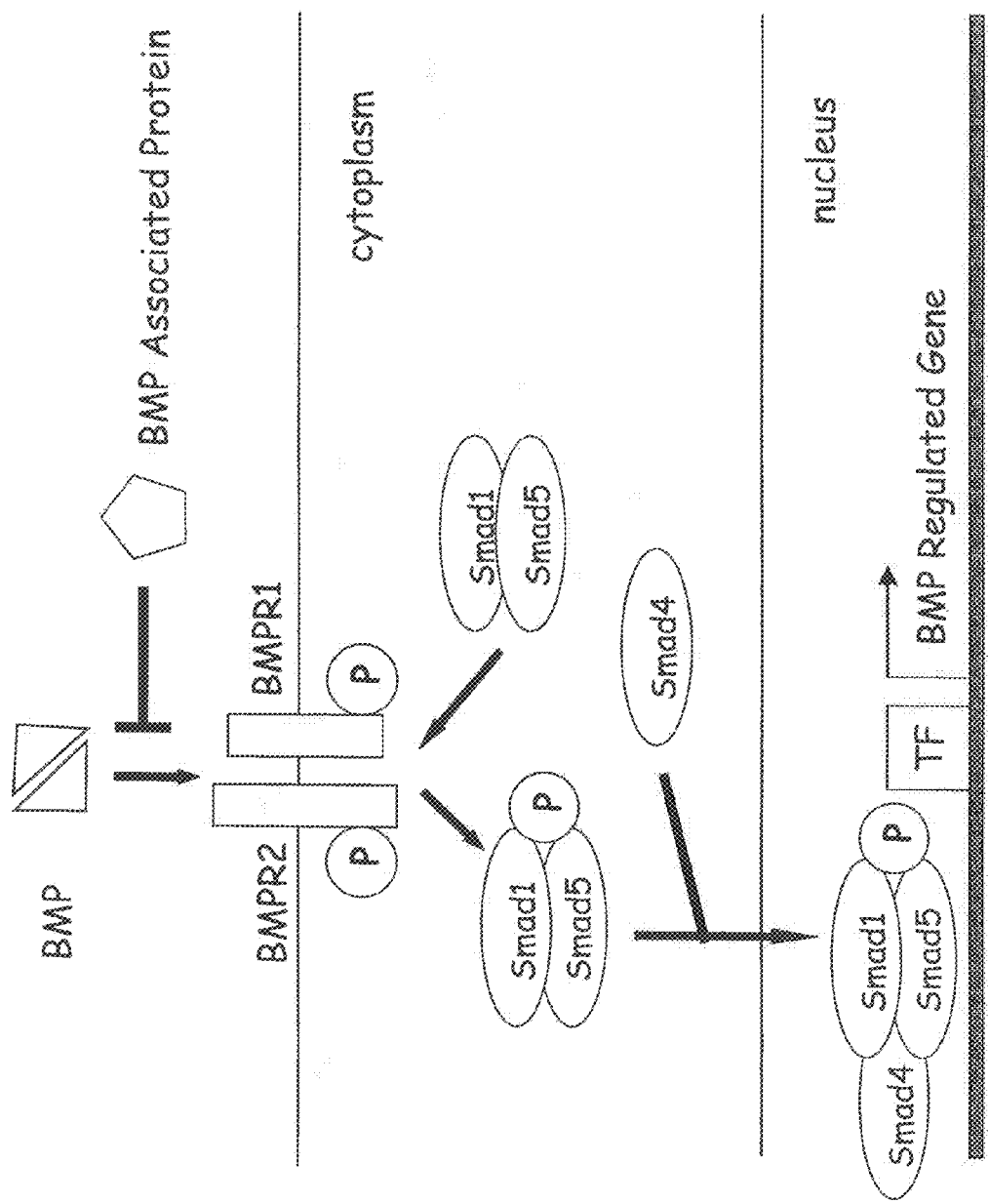
FIG. 5. Bone morphogenic protein signaling pathway. Bone Morphogenic Protein (BMP) dimers bind to a membrane complex composed of BMP receptors 1 and 2, which are serin/threonine kinases. The regulatory Smads (Smad1/Smad5) become phosphorylated and associate with a co-Smad (Smad 4). This resulting Smad complex enters the nucleus where it associates with transcription factors (TF) and regulates gene expression. BMP associated proteins act as BMP antagonists by binding BMPs and preventing BMP interaction with BMP receptors.

The trabecular meshwork has been proposed to play an important role in the normal flow of the aqueous humor, and has been presumed to be the major site of outflow resistance in glaucomatous eyes. Human trabecular meshwork (HTM) cells are specialized cells which line the outflow channels by which aqueous humor exits the eye. Altered synthetic function of the cells may be involved in the pathogenesis of POAG, steroid glaucoma, and other types of glaucoma.

Despite years of intensive research, the precise molecular mechanisms responsible for glaucomatous damage to the eye are not known. Recent research has suggested that growth factors may be important in maintaining normal homeostasis in the ocular tissues associated with glaucoma, and alterations in growth factor/growth factor receptors may play a role in glaucoma pathogenesis. Growth factors area very large family of polypeptides that control cell growth and differentiation. These molecules have a variety of cell-specific effects on gene expression, extracellular matrix composition and deposition, cytoskeletal organization, and regulation of cellular functions. The TM expresses a wide variety of growth factors, growth factor receptors (Tripathi et al. 1993a; Tripathi et al. 1993b; Tripathi et al. 1994a; Tripathi et al. 1994b; Wordinger et al. 1998; Wordinger et al. 1999) as well as neurotrophin/neurotrophic factors and their receptors (Liu et al. 2001; Wordinger et al. 2000). ONH astrocytes and lamina cribrosa cells, two cell types of the optic nerve head, express growth factors, neurotrophins and their receptors (Lambert et al. 2001; Pena et al. 1999). The aqueous humor also contains a variety of growth factors including FGF2, EGF, TGFβ, HGF (Tripathi et al. 1996; Tripathi et al. 1991; Tripathi et al. 1992; Hu and Ritch 2001) as well as neurotrophins (Chundru et al. 2000). Elevated levels of aqueous humor TGFβ-2 and HGF have been reported in POAG patients (Tripathi et al. 1994c; Inatani et al. 2001; Picht et al. 2001). Growth factors may be involved in glaucoma by altering the normal development and/or function of the TM and ONH.

The present invention stems in part from the recognition that bone morphogenic proteins (BMPs) not only induce bone and cartilage formation but are multifunctional cytokines having a wide range of effects on numerous cell types (Hogan 1996; Reddi 1997) and are expressed by both human trabecular meshwork (HTM) and optic nerve head (ONH) cells (Wordinger et al. 2002). BMPs are members of the TGFβ superfamily, and there are approximately 15-20 BMPs genes in man, 3 BMP receptors, and a number of BMP associated proteins that function as BMP antagonists (Yamashita et al. 1996). BMPs signal via a receptor complex consisting of BMPR-I and BMPR-II. It has been reported that superfamily members TGFβ and TGFβR (Agarwal et al. 1997; Lambert et al. 1997) and GDNF and GDNFR (Wordinger et al. 1999; Liu et al. 1999) are expressed by both HTM and ONH cells.

BMPs and BMP receptors are expressed in ocular tissues (Obata et al. 1999; You et al. 1999), but previous reports have focused on ocular development. The function of BMPs is important in ocular development since targeted disruption of genes encoding BMPs in mice leads to severe developmental defects in the retina and the lens (Jena et al. 1997; Luo et al. 1995; Dudley et al. 1995). BMP-2, BMP-4 and BMP-7 are involved in the development of the lens and retina (Jena et al. 1997; Furuta and Hogan 1998; Reddi 2000; Trousse et al. 2001). BMP-6 and BMP-7 also appear to play a role in protecting neurons from hypoglycemic or ischemic damage (Nonner et al. 2001; Liu et al. 2001), and BMP2 has been shown to enhance ganglion cell neurotrophin expression (Zhang et al. 1998). Heterozygous knock-out mice haploinsufficient for Bmp4 have ocular phenotypes including anterior segment dysgenesis, elevated IOP, and optic nerve abnormalities (Chang et al. 2001). There has been very limited information published concerning the role of BMPs in the human postnatal eye.

Mohan and colleagues (1998) reported that BMP-2 and BMP-4 and BMP receptors were expressed in cells of the adult cornea and suggested that BMP function might include corneal keratocyte proliferation and apoptosis. You and colleagues (1999) verified this study and also reported the expression of BMP-3, BMP-5, and BMP-7 in ex vivo and cultured corneal epithelium and stromal cells. They reported that the level of BMP transcription was higher in the stroma while the level for receptors was higher in cultured corneal epithelial cells.

Using RT-PCR, the present inventors discovered mRNAs for BMPs, BMP receptors BMPR-IA, BMPR-IB and BMPR-II, as well as BMP binding proteins gremlin, chordin, follistatin, and bambi, in HTM, lamina cribosa (LC) and ONH astrocyte cell lines and tissues (Wordinger et al. 2002). The present inventors further discovered that HTM and ONH cells express proteins BMP-2, BMP-4, BMP-5 and BMP-7.

Glaucoma will be diagnosed by characterization of genetic changes in genes of members of the BMP signaling family. As used herein, the phrases "bone morphogenic protein family member gene" and "BMP signaling family" refer to all BMPs, BMP receptors and associated proteins. The term "genetic changes" is well known by those skilled in the art. There are numerous examples of diseases associated with genetic changes in specific genes (for examples see Cummings 1997; Strachan, et al. 1996; Jorde, et al. 1999). Genetic changes in a specific gene (e.g. BMP) can be determined using a variety of techniques well known by those skilled in the art, such as: SSCP, DGGE, ASO, RFLP, heteroduplex analysis, CCM, PTT, and RNase cleavage (see Birren, et al. 1998).

Glaucoma may be caused by altered expression of one or more BMP family genes in the eye, which leads to elevated IOP and/or glaucomatous optic neuropathy. "Altered BMP gene expression" means expression of this gene product that is different from normal. The term may also refer to alterations in the sequence of the gene or protein. The normal BMP gene has been well characterized (see above), and the expression of BMP has been reported in a variety of tissues including the TM and ONH. Genetic changes in the coding region of BMP family genes may alter the function of these proteins. Genetic changes outside the coding region may also lead to glaucoma.

It is well known by those skilled in the art that "changes outside" of the coding region of a specific gene are important in the regulation of gene expression. For example, the region upstream (5') of the coding region of most genes is known as the promoter region which "promotes" and regulates the expression of that gene. The promoter region contains numerous nucleotide sequences recognized by various transcription factors and DNA binding proteins that are responsible for activation or repression of gene expression. Regions downstream (3') of the gene can determine poly-adenylation of the gene product, thereby regulating RNA processing and translation of the gene product.

The altered expression of BMP genes or mutations in the sequence of the genes that is indicative of glaucoma may be detected using techniques well known to those of skill in the art. For example, it is contemplated that a nucleic acid fragment of almost any length may be employed, with the total length preferably being limited by the ease of preparation and use in the intended protocol. The nucleic acid sequences disclosed herein may also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of BMP-2A (SEQ ID NO:1), BMP-4 (SEQ ID NO:3), BMP-5 (SEQ ID NO:5), BMP-7 (SEQ ID NO:7), BMP-RIA (SEQ ID NO:37), BMP-RIB (SEQ ID NO:39), BMP-RII (SEQ ID NO:41), chordin (SEQ ID NO:43), gremlin (SEQ ID NO:45), follistatin (SEQ ID NO:47), or bambi (SEQ ID NO:53) will find particular utility. Longer contiguous identical or complementary sequences, e.g., those of about 20, 30, 40, 50, 100, 200, 500, 1000 nucleotides (including all intermediate lengths), and even up to full length sequences of about 1547 nucleotides (for BMP-2A), 1946 nucleotides (for BMP-4), 2153 nucleotides (for BMP-5) and 1878 nucleotides (for BMP-7), 2932 nucleotides (for BMP-RIA), 2032 nucleotides (for BMP-RIB), 3611 nucleotides (for BMP-RII), 3561 nucleotides (for chordin), 4049 nucleotides (for gremlin), 1386 nucleotides (for follistatin), and 1523 nucleotides (for bambi) will also be of use in certain embodiments.

It will be readily understood that "intermediate lengths", in this context, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000 ranges, up to and including sequences of 2,001, 2002, 2050, 2051, and the like.

The ability of such nucleic acid probes and primers to specifically hybridize to BMP coding sequences and primers to specifically amplify BMP sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10, 20, 30, 50, or even of 100-200 nucleotides or so, identical or complementary to BMP-2A (SEQ ID NO:1), BMP4 (SEQ ID NO:3), BMP-5 (SEQ ID NO:5), BMP7 (SEQ ID NO:7), BMP-RIA (SEQ ID NO:37), BMP-RIB (SEQ ID NO:39), BMP-RII (SEQ ID NO:41), chordin (SEQ ID NO:43), gremlin (SEQ ID NO:45), follistatin (SEQ ID NO:47), or bambi (SEQ ID NO:53) are particularly contemplated as hybridization probes for use in, e.g., SNP evaluation and solid phase hybridization assays, in addition to Southern and northern blotting. This would allow BMP structural or regulatory genes to be analyzed, both in tissues and cells. The total size of fragment, as well as the size of the complementary stretch(es), will ultimately depend on the intended use of application of the particular nucleic acid segment. Smaller fragments will generally find use in hybridization embodiments, wherein the length of the contiguous complementary region may be varied, such as between about 10 and about 100 nucleotides, but larger contiguous complementary stretches of up to about 1547 nucleotides (for BMP-2A), 1946 nucleotides (for BMP-4), 2153 nucleotides (for BMP-5) and 1878 nucleotides (for BMP-7), 2932 nucleotides (for BMP-RIA), 2032 nucleotides (for BMP-RIB), 3611 nucleotides (for BMP-RII), 3561 nucleotides (for chordin), 4049 nucleotides (for gremlin), 1386 nucleotides (for follistatin), and 1523 nucleotides (for bambi) may be used, according to the length complementary sequences one wishes to detect.

The use of a hybridization probe of about 10-14 nucleotides in length allows the formation of a duplex molecule that is both stable and selective. Molecules having contiguous complementary sequences over stretches greater than 10 bases in length are generally preferred, though, in order to increase stability and selectivity of the hybrid, and thereby improve the quality and degree of specific hybrid molecules obtained, one will generally prefer to design nucleic acid molecules having gene-complementary stretches of 15 to 20 contiguous nucleotides, or even longer where desired.

Hybridization probes may be selected from any portion of any of the sequences disclosed herein. All that is required is to review the sequence set forth in SEQ ID NO: 1, SEQ ID NO:3, SEQ ID NO:5, SEQ ID NO:7, SEQ ID NO:37, SEQ ID NO:39, SEQ ID NO:41, SEQ ID NO:43, SEQ ID NO:45, SEQ ID NO:47 or SEQ ID NO:53 and to select any continuous portion of the sequence, from about 10 nucleotides in length up to and including the full length sequence, that one wishes to utilize as a probe or primer. The choice of probe and primer sequences may be governed by various factors, such as, by way of example only, one may wish to employ primers from towards the termini of the total sequence, or from the ends of the functional domain-encoding sequences, in order to amplify further DNA.

The process of selecting, and preparing a nucleic acid segment that includes a contiguous sequence from within BMP-2A (SEQ ID NO:1), BMP4 (SEQ ID NO:3), BMP-5 (SEQ ID NO:5), BMP7 (SEQ ID NO:7), BMP-RIA (SEQ ID NO:37), BMP-RIB (SEQ ID NO:39), BMP-RII (SEQ ID NO:41), chordin (SEQ ID NO:43), gremlin (SEQ ID NO:45), follistatin (SEQ ID NO:47), or bambi (SEQ ID NO:53) may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 and U.S. Pat. No. 4,682,195 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of BMP genes or cDNAs. Depending on the application envisioned, one will desire to employ varying degrees of selectivity of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M-0.15M NaCl at temperatures of 50° C. to 70° C. Such selective conditions tolerate little, if any, mismatch between the probe and the template or target strand, and would be particularly suitable for examining BMP genes.

Of course, for some applications, for example, where one desires to prepare or identify mutants employing a mutant primer strand hybridized to an underlying template or where one seeks to isolate BMP encoding sequences from related species, functional equivalents, or the like, less stringent hybridization conditions will typically be needed in order to allow formation of the heteroduplex. In these circumstances, one may desire to employ conditions such a 0.15M-1.0M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by decreasing NaCl concentrations or by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

It will also be understood that this invention is not limited to the particular nucleic acid and amino acid sequences of BMP-2A (SEQ ID NO:1), BMP4 (SEQ ID NO:3), BMP-5 (SEQ ID NO:5), BMP7 (SEQ ID NO:7), BMP-RIA (SEQ ID NO:37), BMP-RIB (SEQ ID NO:39), BMP-RII (SEQ ID NO:41), chordin (SEQ ID NO:43), gremlin (SEQ ID NO:45), follistatin (SEQ ID NO:47), or bambi (SEQ ID NO:53). Recombinant vectors and isolated DNA segments may therefore variously include the BMP coding regions themselves, upstream or downstream regions of the genes, coding regions bearing selected alterations or modifications in the basic coding region, or they may encode larger polypeptides that nevertheless include BMP coding regions or may encode biologically functional equivalent proteins or polypeptides that have variant amino acid sequences.

The DNA segments of the present invention encompass biologically functional equivalent BMP proteins and polypeptides. Such sequences may arise as a consequence of codon redundancy and functional equivalency that are known to occur naturally within nucleic acid sequences and the proteins thus encoded. Alternatively, functionally equivalent proteins or polypeptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test BMP mutants in order to examine binding activity at the molecular level.

The therapeutic agent for the treatment of glaucoma can be: a peptide or protein, a peptide mimetic, an oligonucleotide or derivatized oligonucleotide, or small drug-like molecule, all which affect one or more aspects of the ocular BMP pathways. Preferred therapeutic agents are those that are: (1) BMP2, BMP4, BMP5, or BMP7 agonists; (2) chordin, gremlin, follistatin, or bambi antagonists; and/or (3) Smad1, Smad5 and/or Smad4 agonists.

The agent may be delivered directly to the eye (for example: topical ocular drops or ointments; slow release devices in the cul-de-sac or implanted adjacent to the sclera or within the eye; periocular, conjunctival, sub-Tenons, intracameral or intravitreal injections) or parenterally (for example: orally; intravenous, subcutaneous or intramuscular injections; dermal delivery; etc.) using techniques well known by those skilled in the art. The following are examples of possible formulations embodied by this invention.

|  | wt. % |
|---|---|
| (a) Topical ocular formulation | |
| Agent that increases ocular BMP-4 expression | 0.01-2 |
| HPMC | 0.5 |
| Sodium chloride | 0.8 |
| BAC | 0.01% |
| EDTA | 0.01 |
| NaOH/HCl | qs pH 7.4 |
| Purified water | qs 100 mL |

-continued

| | wt. % |
|---|---|
| (b) Topical ocular formulation | |
| Gremlin antagonist | 0.01-2 |
| HPMC | 0.5 |
| Sodium chloride | 0.8 |
| BAC | 0.01 |
| EDTA | 0.01 |
| NaOH/HCl | qs pH 7.4 |
| Purified water | qs 100 mL |
| (c) Topical ocular formulation | |
| Smad 1/5 agonist | 0.01-2 |
| HPMC | 0.5 |
| Sodium chloride | 0.8 |
| BAC | 0.01 |
| EDTA | 0.01 |
| NaOH/HCl | qs pH 7.2 |
| Purified water | qs 100 mL |

It is further contemplated that the compounds of the invention could be formulated in intraocular insert devices.

A. Assay for Therapeutic Agents

This invention is also useful for the discovery of new anti-glaucoma therapeutic agents that are involved in the BMP signaling pathway (see FIG. 5). Selective BMP ligands bind to BMP type I and type II serine/threonine kinase receptors (BMP-RI and BMP-RII) and transduce signal via Smad proteins. The BMP signal is propagated by Smads through protein-protein and protein-DNA interactions (Attisano and Tuen Lee-Hoeflich 2001). Regulatory Smad 1 and Smad 5 are activated (via phosphorylation) by ligand bound BMP receptors (von Bubnoff and Cho 2001). These regulatory Smads then interact with Smad 4 to form a heteromeric complex that translocates to the nucleus. This complex is able to activate or repress the transcription of selective genes that recognize this transcriptional complex, depending on which nuclear co-factors are present.

The BMP/Smad signaling pathway is negatively regulated by several mechanisms. Certain BMP-binding proteins (such as gremlin, BAMBI, or follistatin) bind BMPs and inhibit their interaction with BMP receptors. In addition, there are inhibitory Smad proteins (e.g. Smad 6 and Smad 7), which bind and inactivate BMP receptors. (Kowabata et al. 1998; Itoh et al. 2000; Miyazono 2000). The present inventors have discovered that human TM cells, ONH astrocytes and lamina cribrosa cells express message and protein for the BMP receptor complex. Thus, these cells could respond to endogenous BMP ligands.

Various methods may be used to discover new anti-glaucoma therapeutic agents, and these techniques are well known to those skilled in the art. For example, peptide or peptide mimetic agents that act as agonists or inhibitors of BMPs can be discovered through molecular modeling of BMP/BMP receptor structures (Nickel et al. 2001). BMP signal transduction involves select sets of Smad proteins (Kawabata et al. 1998; Itoh et al. 2000; Attiseno et al. 2000). Select BMP agonists and Smad agonists can be discovered using cell based assays. The test cell should express the appropriate BMP receptor(s) and possess the appropriate BMP signaling pathway. Because one of the major effects of BMP signaling is the alteration of gene expression, BMP agonists and Smad agonists can be discovered by screening for BMP-induced genes. The induction of BMP regulated genes also may be assayed by quantitating levels of mRNA using quantitative RT-PCR (Wang et al. 2001), DNA microarrays, or reporter gene constructs. There are natural inhibitors of BMP signaling, the BMP binding proteins (also known as BMP-associated proteins), such as chordin, gremlin, and follistatin. Antagonists of the protein inhibitors can be discovered using ligand binding assays. For example, test agents can be added to recombinant purified gremlin, and those agents that bind to gremlin are identified using a variety of techniques known to those skilled in the art. To determine whether these agents are gremlin antagonists, a cell based assay similar to that described above is used.

It is contemplated that any known in vitro and in vivo screening models may be used in conjunction with the present invention to identify new glaucoma therapies directed to the BMP family of genes. Such models are well known to those skilled in the art and their practice has become routine. Small peptides or peptide mimetics can be designed based on structure/function knowledge of the BMP, BMPR, and/or BMP binding protein gene products. Ligand binding assays can be used to detect small molecules that bind to BMPs, BMPRs, or BMP binding proteins. Cell based assays can look at the effects of various agents on BMP signaling pathways. Knock-in cell lines containing BMP family gene promoters coupled to a reporter gene can be generated to look for agents that alter BMP family member gene expression. These assays can be used to identify both agonist and antagonist molecules. Ex vivo assays, such as perfusion cultured anterior segments from human eyes (Clark et al. 1995a; Pang et al. 2000), can be used to examine the effects of agents on IOP and on BMP signaling in TM tissue. Rodent models of glaucoma can be generated using well-known techniques to create stable BMP family member transgenic, knockout, or knock-in strains of mice and rats. These rodent models can be used to screen for agents that alter the glaucoma-like phenotype(s) (e.g. tonometry to evaluate effects on IOP, histology to evaluate effects on glaucomatous optic neurology).

B. Kits

The present invention provides methods, compositions and kits for the early detection of glaucoma. The kits can contain a nucleic acid segment encoding a BMP polypeptide or protein. The kit can further contain reagents for detecting an interaction between a sample and a nucleic acid or peptide of the present invention. The provided reagent can be radio-, fluorescently- or enzymatically-labeled. The kit can contain a known radiolabeled agent capable of binding or interacting with a nucleic acid or peptide or protein of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatography media, a test plate having a plurality of wells, or a microscope slide. When the reagent provided is a dry powder, the powder can be reconstituted by the addition of a suitable solvent, that may be provided.

In still further embodiments, the present invention concerns diagnostic methods and associated kits for the diagnosis of glaucoma. It is proposed that the BMP associated peptides and nucleic acids of the invention may be employed to detect polymorphisms or mutations in the BMP nucleic acids from patient samples. In general, these methods will include first obtaining a sample suspected of containing such a polymorphism or mutation, contacting the sample with a peptide or nucleic acid of the present invention, as the case may be, under conditions effective to allow the formation of a complex, and then detecting the presence of the complex.

In general, the detection of complex formation is quite well known in the art and may be achieved through the application of numerous approaches. For example, the present invention contemplates the application of ELISA, RIA, indirect fluorescence techniques and the like. Generally, complex formation will be detected through the use of a label, such as a radiolabel or an enzyme tag (such as alkaline phosphatase, horseradish peroxidase, or the like). Of course, one may find additional advantages through the use of a secondary binding ligand.

The following examples are representative of the techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Example 1

Cell culture: Human TM cells and ONH cells were generated from donor eyes as described (Steely et al 1992; Steely et al. 2000; Wilson et al. 1993; Clark et al. 1994; Clark et al. 1995b; Clark et al. 1995c; Clark et al. 1996; Clark et al. 2001a; Clark et al. 2001b; Dickerson et al. 1998; Wordinger et al. 1998; Wordinger et al. 1999; Wordinger et al. 2000; Wordinger et al. 2002; Lambert et al. 2001; Agarwal et al. 1999; Liu et al. 2001). TM cells were grown from TM explants of donors ranging in age from 6 days to 90 years. Human optic nerve head astrocytes and lamina cribrosa (LC) cells were generated from carefully dissected optic nerve heads (donors aged 2 days to 90 years) and characterized according to previous reports (Lambert et al. 2001; Clark et al. 1995a). The cells were grown to confluency in the following media: Ham's F10 media (JRH Biosciences, Lenexa, Kans.) containing 10% fetal bovine serum (HyClone, Logan, Utah) and antibiotics (Gibco BRL-Life Technologies, Grand Island, N.Y.) for TM cells; Dulbecco's modified Eagle's media (DMEM, HyClone) containing 10% FBS for LC cells; and astrocyte growth medium (AGM, Clonetics, San Diego, Calif.) containing 5% FBS for ONH astrocytes.

RT-PCR: Human TM and ONH tissues also were dissected from donor eyes (Wordinger et al. 1998; Wang et al. 2001). Total RNA was extracted from the TM and ONH cells and tissues using TRIzol extraction (Gibco BRL-Life Technologies), and cDNA prepared by reverse transcription using standard procedures (Wordinger et al. 1998; Wordinger et al. 1999; Wordinger et al. 2000; Wordinger et al. 2002). PCR primers were designed using the Oligos 4.0 software program (see primer pairs in Table 1). All primer pairs were designed so that amplification of potentially contaminated genomic DNA sequences would produce mRNA PCR products that would be substantially larger than expected, because intron sequences that were excised during RNA processing would be included in genomic DNA. The β-actin PCR primers, AGGCCAACCGCGAGAAGATGACC (upstream) (SEQ ID NO: 55) and GAAGTCCAGGGCGACGTAGCAC (downstream) (SEQ ID NO: 56) with an annealing temperature of 55° C. yielded a PCR product of 350 bp.

PCR reactions were run as described (Wordinger et al. 1998; Wordinger et al. 1999; Wordinger et al. 2000; Lambert et al. 2001; Wordinger et al. 2002) using Taq Start Antibody Hot Start with the following cycle conditions: 2 minutes at 94° C., 2 minutes at 92° C., and 40 cycles of 30 seconds at the optimal annealing temperature, extension for 90 seconds at 72° C. and denaturation for 45 seconds at 92° C. The amplified PCR products were examined by horizontal electrophoresis in 1.5% agarose gels. To ensure specificity of the RT-PCR products, Southern blot analysis was performed with probes designed using Oligo 4.0 that hybridized to a region within the amplified PCR product. PCR products were sequenced to verify the specificity of the PCR reactions. Table 2 lists the members of the BMP family that are expressed in the human TM and ONH.

TABLE 1

PCR Primer Pairs, Annealing Temperature and Amplimer Size of BMPs

| Name | Assession Number | Upstream PCR Primer | Downstream PCR Primer | Ampl. Size (bp) |
|---|---|---|---|---|
| BMP-2A | NM_001200 | ACTGCGGTCTCCTAAAGGTCGA (SEQ ID NO: 9) | GCTGACCTGAGTGCCTGCGAT (SEQ ID NO: 10) | 657 |
| BMP-4 | NM_001202 | GAATGCTGATGGTCGTTTTTATTATG (SEQ ID NO: 11) | AGACTGAAGCCGGTAAAGAT (SEQ ID NO:12) | 348 |
| BMP-5 | NM_021073 | AAGAGGACAAGAAGGACTAAAAATAT (SEQ ID NO: 13) | GTAGAGATCCAGCATAAAGAGAGGT (SEQ ID NO: 14) | 303 |
| BMP-7 | NM_001719 | AGCCCGGGTAGCGCGTAGAG (SEQ ID NO: 15) | GCGCCGGTGGATGAAGCTCGA (SEQ ID NO: 16) | 202 |
| BMPR-1A | NM_004329 | TAAAGGTGACAGTACACAGGAACA (SEQ ID NO: 17) | TCTATGATGGCAAAGCAATGTCC (SEQ ID NO: 18) | 298 |
| BMPR-1B | NM_001203 | TACAAGCCTGCCATAAGTGAAGAAGC (SEQ ID NO:19) | ATCATCGTGAAACAATATCCGTCTG (SEQ ID NO: 20) | 211 |

TABLE 1-continued

PCR Primer Pairs, Annealing Temperature and Amplimer Size of BMPs

| Name | Assession Number | Upstream PCR Primer | Downstream PCR Primer | Ampl. Size (bp) |
|---|---|---|---|---|
| BMPR-II | NM_001204 | TCCTCTCATCAGCCAT TTGTCCTTTC (SEQ ID NO: 21) | AGTTACTACACATTCT TCATAG (SEQ ID NO: 22) | 457 |
| Chordin (CHRD) | AF209930 | CTCTGCTCACTCTGCA CCTG (SEQ ID NO: 23) | CCGGTCACCATCAAAA TAGC (SEQ ID NO: 24) | 198 |
| Gremlin (CKTSF1 B1 | NM_013372 | ATCAACCGCTTCTGTT ACGG (SEQ ID NO: 25) | ATGCAACGACACTGCT TCAC (SEQ ID NO: 26) | 197 |
| Follistatin (FST) | NM_006350 | TGCCACCTGAGAAAGG CTAC (SEQ ID NO: 27) | ACAGACAGGCTCATCC GACT (SEQ ID NO: 28) | 201 |
| Noggin (NOG) | NM_005450 | CACTACGACCCAGGCT TCAT (SEQ ID NO: 29) | CTCCGCAGCTTCTTGC TTAG (SEQ ID NO: 30) | 212 |
| CER-1 | NM_005454 | ATAGTGAGCCCTTCCC ACCT (SEQ ID NO: 33) | AATGAACAGACCCGC ATTTC (SEQ ID NO: 34) | 294 |
| NMA (BAMBI) | NM_005791 | GATCGCCACTCCAGCT ACATC (SEQ ID NO: 35) | GGGCACGGCAATGAC C (SEQ ID NO: 36) | 471 |

TABLE 2

BMP Family Members Expressed in Human TM and ONH

| BMP Family Member | Trabecular Meshwork | Optic Nerve Head |
|---|---|---|
| BMP-2 | + | + |
| BMP-4 | + | + |
| BMP-5 | + | + |
| BMP-7 | + | + |
| BMPR-IA | + | + |
| BMPR-IB | + | + |
| BMPR-II | + | + |
| Chordin | + | + |
| Gremlin | + | + |
| Follistatin | + | + |
| Bambi | + | + |
| Noggin | − | − |
| CER-1 | − | − |

Western immunoblotting: Protein was extracted from cultured cells using lysis buffer, and proteins were separated by denaturing polyacrylamide gel electrophoresis prior to electrophoretic transfer to nitrocellulose membranes (Lambert et al. 2001). The membranes were blocked with 5% milk (for BMPs) or 3% gelatin (for BMPRs) and incubated with the following primary antibodies: BMP2, BMP4, BMP5, BMP7 (all from Santa Cruz, Santa Cruz, Calif.), or BMP-RIA, BMP-RIB, BMP-RII (from Jackson Immuno Research, West Grove, Pa.). The membranes were washed, incubated with secondary antibodies (goat anti-mouse IgG-horseradish peroxidase for BMPs, Santa Cruz; donkey anti-goat-horseradish peroxidase for BMP receptors, Jackson Immuno Research), and developed using the WesternBreeze chemiluminescence immunodetection system (Invitrogen, Carlsbad, Calif.).

Figure 6:
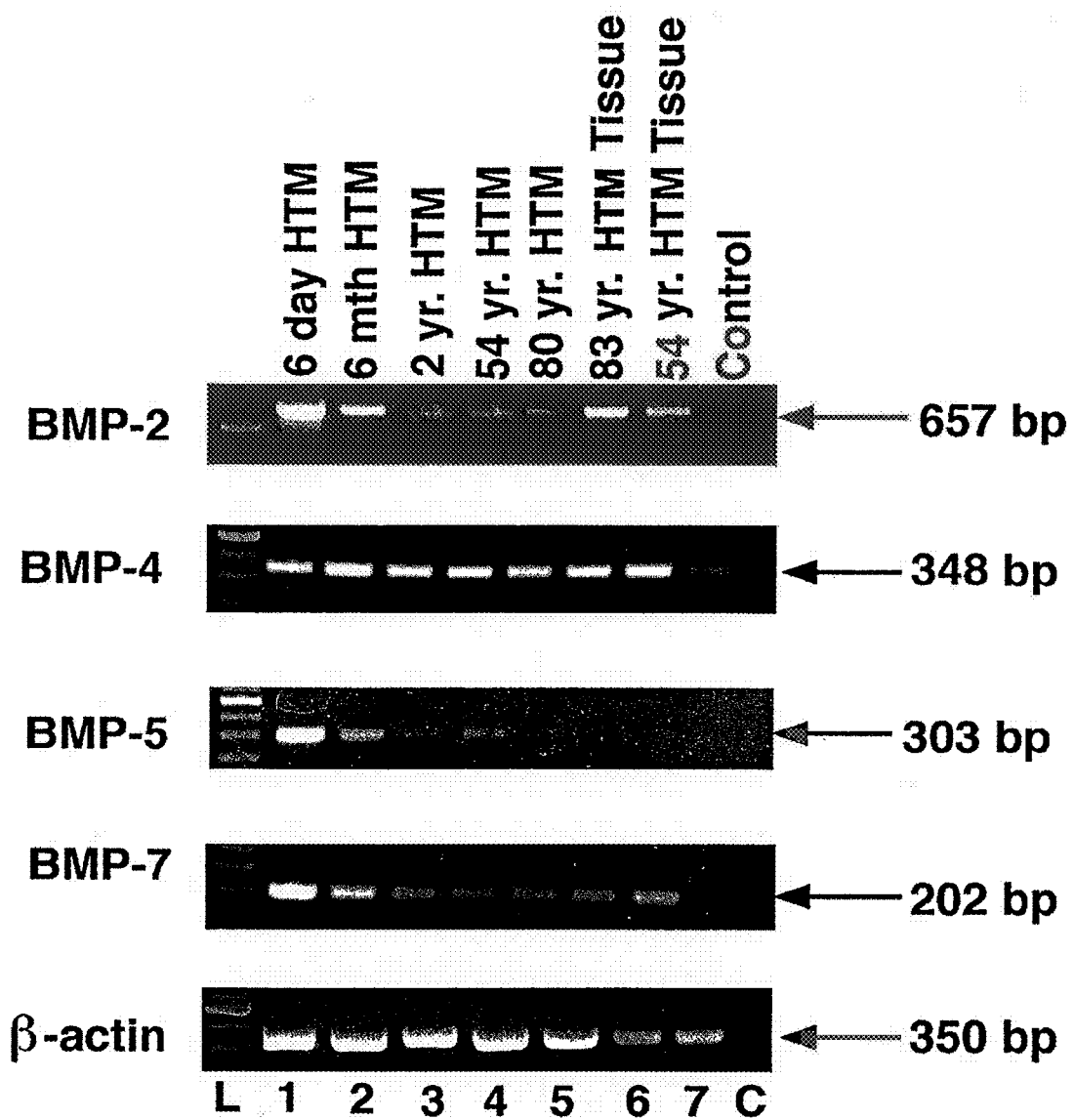
FIG. 6. BMP expression in human TM cells and tissues. Ethidium bromide-stained agarose gel of BMP PCR products from cDNA samples generated from RT-PCR analysis of BMP expression in human TM cells (lanes 1-5) and tissues (lanes 6-7). L=base pair markers. C=PCR negative control lane. β-actin was used as a positive RT-PCR internal control.

Expression of BMPs, BMPRs mRNA in human TM cells and tissues: Amplification products of expected for BMP-2, BMP-4, BMP-5 and BMP-7 primer pairs in human TM cells and tissues are shown in FIG. 6. Southern blots using specific probes verified that these were the expected PCR products. All human TM cell lines and tissues expressed message for BMP-2, BMP-4, and BMP-7. However, message for BMP-5 was low to undetectable in human TM tissue samples (FIG. 6, lanes 6 and 7). Control reactions without cDNA did not result in amplification products indicating that reagents and primers were free of DNA or RNA contamination (FIG. 6, lane C).

Figure 7:
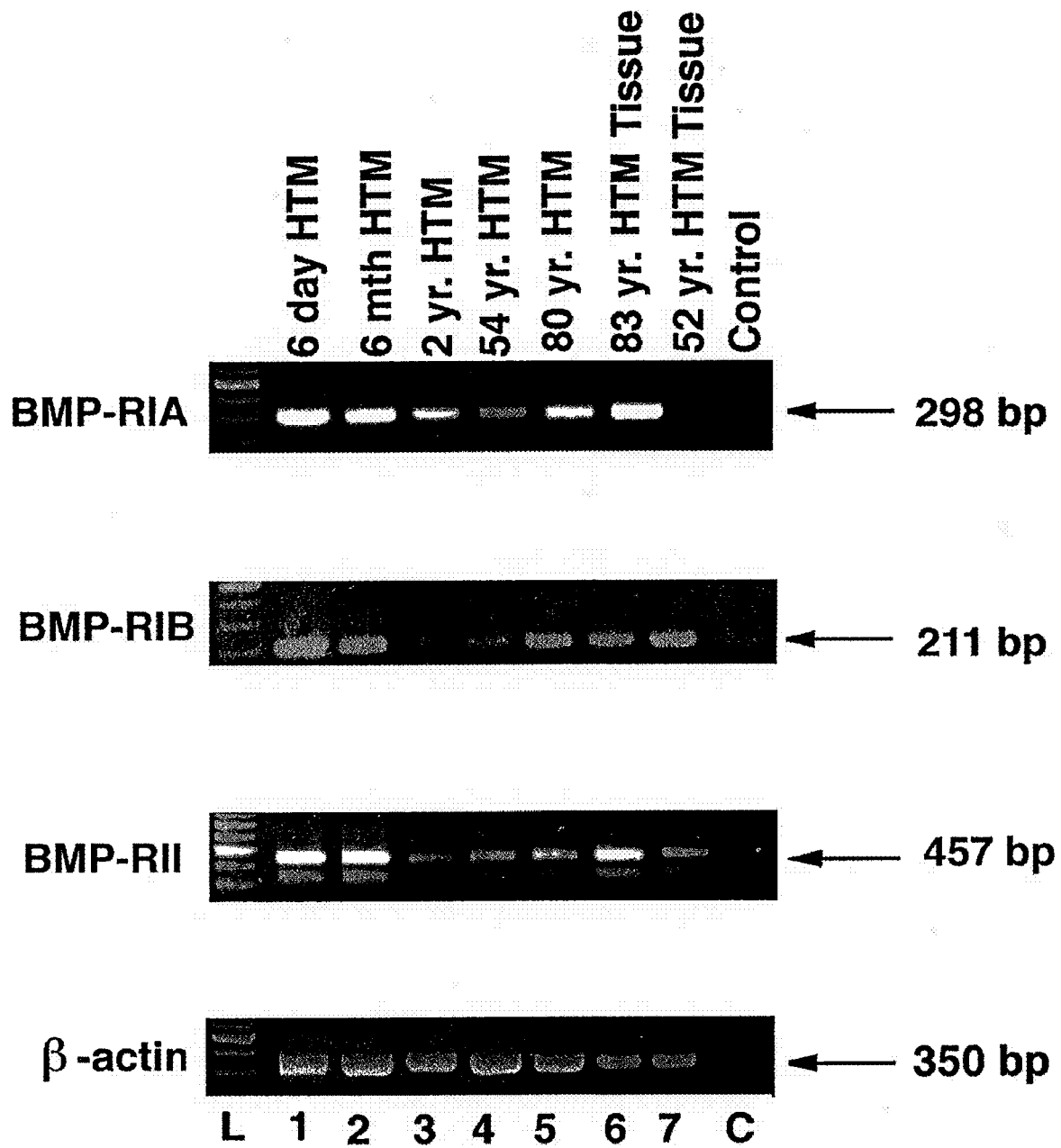
FIG. 7. BMP receptor expression in human TM cells and tissues. Ethidium bromide-stained agarose gel of PCR products from cDNA samples generated from RT-PCR analysis of BMP receptor expression in human TM cells (lanes 1-5) and tissues (lanes 6-7). L=base pair markers. C=PCR negative control lane. β-actin was used as a positive RT-PCR internal control.

FIG. 7 shows the amplification products of expected size for BMP-RIA, BMP-RIB, and BMP-RII primer pairs in human TM cells and tissues. All human TM cells and tissues expressed message for the BMP receptor complexes. Southern blots using specific probes verified that these were the expected PCR products. An alternate amplification product (350 bp) was detected in the BMP-RII PCR reaction. The alternate amplification product was present in all human TM cells and tissues. This alternate band is currently being identified to determine if it is an alternate spliced form of the receptor. Control reactions without cDNA did not result in amplification products (FIG. 7, lane C) indicating that reagents and primers were free of DNA or RNA contamination.

Figure 8:
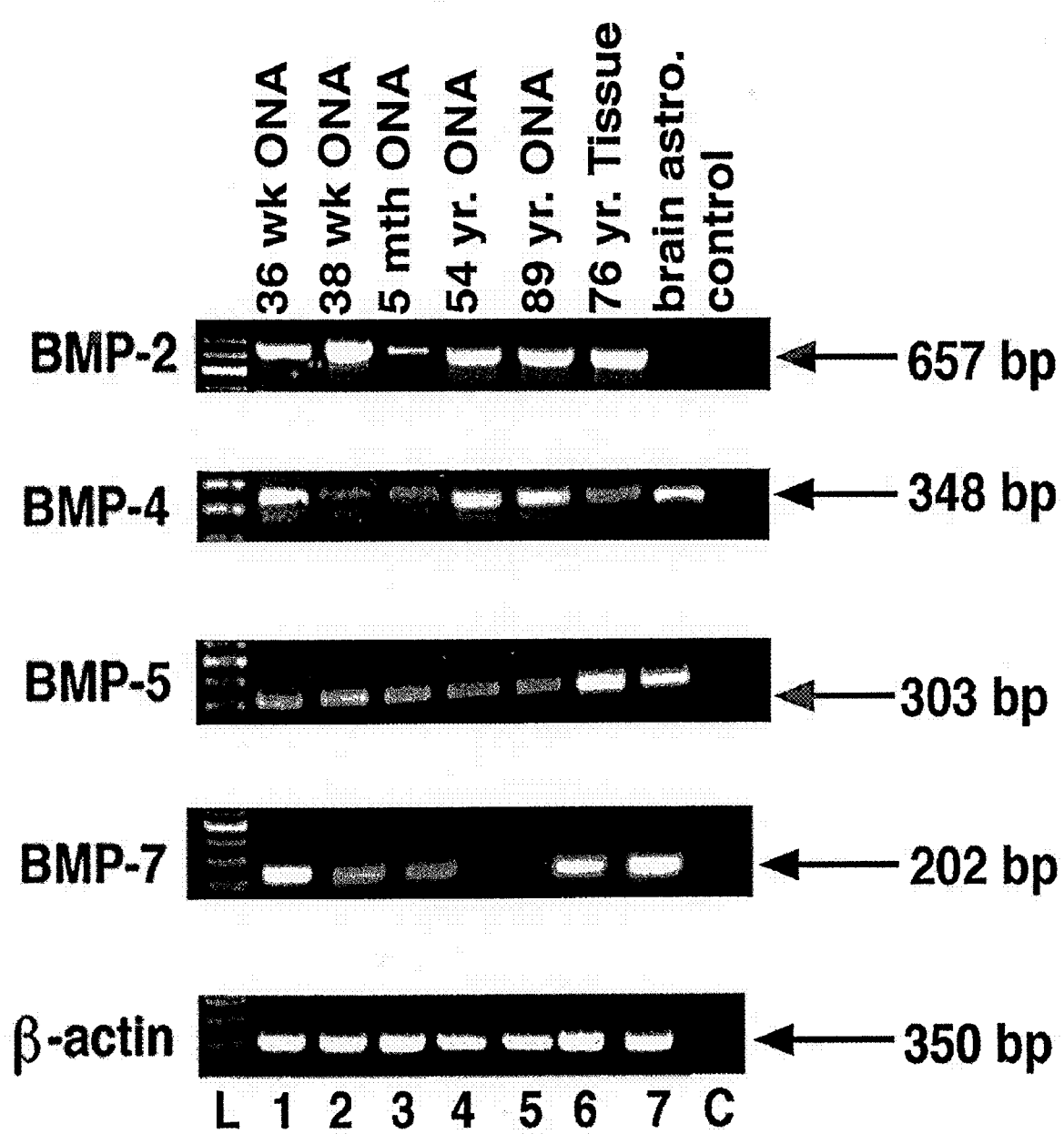
FIG. 8. BMP expression in human ONH astrocytes, ONH tissues, and human brain astrocytes. Ethidium bromide-stained agarose gel of PCR products from cDNA samples generated from RT-PCR analysis of BMP expression in human ONH astrocyte (lanes 1-5), ONH tissue (lane 6), and human brain astrocytes (lane 7). L=base pair markers. C=PCR negative control lane. β-actin was used as a positive RT-PCR internal control.

Expression of BMP and BMP receptor mRNA in human ONH cells and tissues: Amplification products of expected size for BMP-2, BMP-4, BMP-5 and BMP-7 primer pairs in human ONH astrocytes and ONH tissues are shown in FIG. 8. All ONH astrocytes and ONH tissue expressed message for the respective BMP. Human brain astrocytes were used as a positive control cell line. Southern blots using specific probes verified that these were the expected PCR products. With the exception of BMP-2, all other BMP were expressed by human brain astrocytes (FIG. 8, lane 7). Control reactions without cDNA did not result in amplification products (FIG. 8, lane C) indicating that reagents and primers were free of DNA or RNA contamination.

Figure 9:
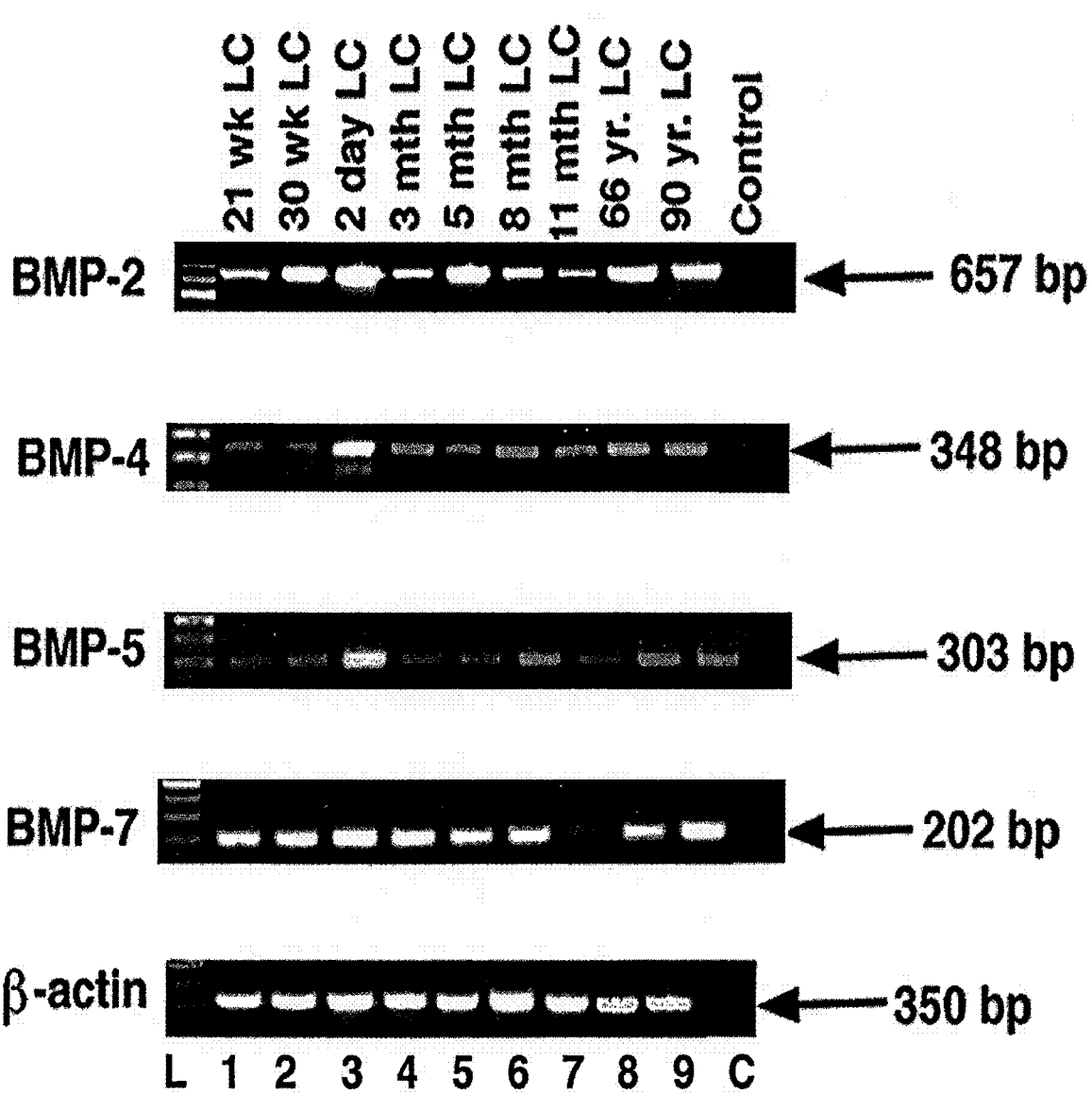
FIG. 9. BMP expression in human lamina cribrosa cell lines. Ethidium bromide-stained agarose gel of PCR products from cDNA samples generated from RT-PCR analysis of human lamina cribrosa cells (lanes 1-9). L=base pair markers. C=PCR negative control lane. β-actin was used as a positive RT-PCR internal control.

FIG. 9 shows the amplification products of expected sizes for BMP-2, BMP-4, BMP-5 and BMP-7 primer pairs in cultured human LC cells. All LC cell lines expressed message for each BMP. Southern blots using specific probes verified that these were the expected PCR products. Control reactions without cDNA did not result in amplification products (FIG. 9, lane C) indicating that reagents and primers were free of DNA or RNA contamination.

Figure 10:
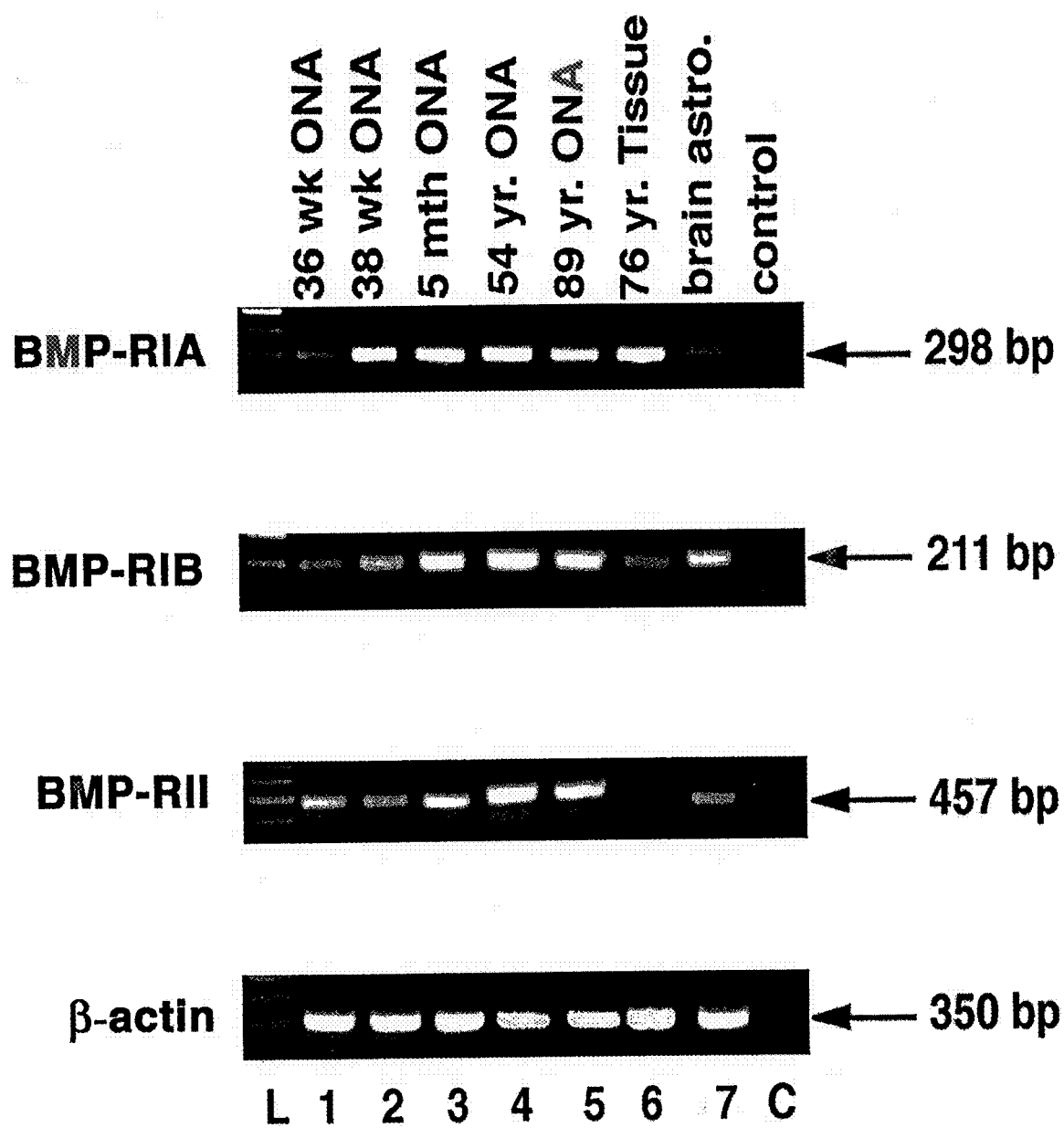
FIG. 10. BMP receptor expression in human ONH astrocytes, ONH tissues, and human brain astrocytes. Ethidium bromide-stained agarose gel of PCR products from cDNA samples generated from RT-PCR analysis of BMP receptor expression in human optic nerve head astrocytes (ONA) (lanes 1-5), ONH tissue (lane 6), and human brain astrocytes (lane 7). L=base pair markers. C=PCR negative control lane. β-actin was used as a positive RT-PCR control.

Amplification products of expected size for BMP-RIA, BMP-RIB, and BMP-RII primer pairs in human ONH astrocytes and ONH tissues are shown in FIG. 10. All ONH astrocyte cell lines and tissues expressed message for BMP-RIA and BMP-RIB. Southern blots using specific probes verified that these were the expected PCR products. With the exception of ONH tissue (FIG. 10, lane 6), BMP-RII was expressed by all ONH astrocyte cell lines. Message for all BMP receptors (FIG. 10, lane 7) was expressed by a human brain astrocyte cell line that served as a positive control. There appears to be a discrepancy in the expression of BMP-RII in ONH tissue and ONH cell lines. The reduced expression in ONH tissue may reflect a low level of expression. Control reactions without cDNA did not result in amplification products (FIG. 5, lane C) indicating that reagents and primers were free of DNA or RNA contamination.

Figure 11:
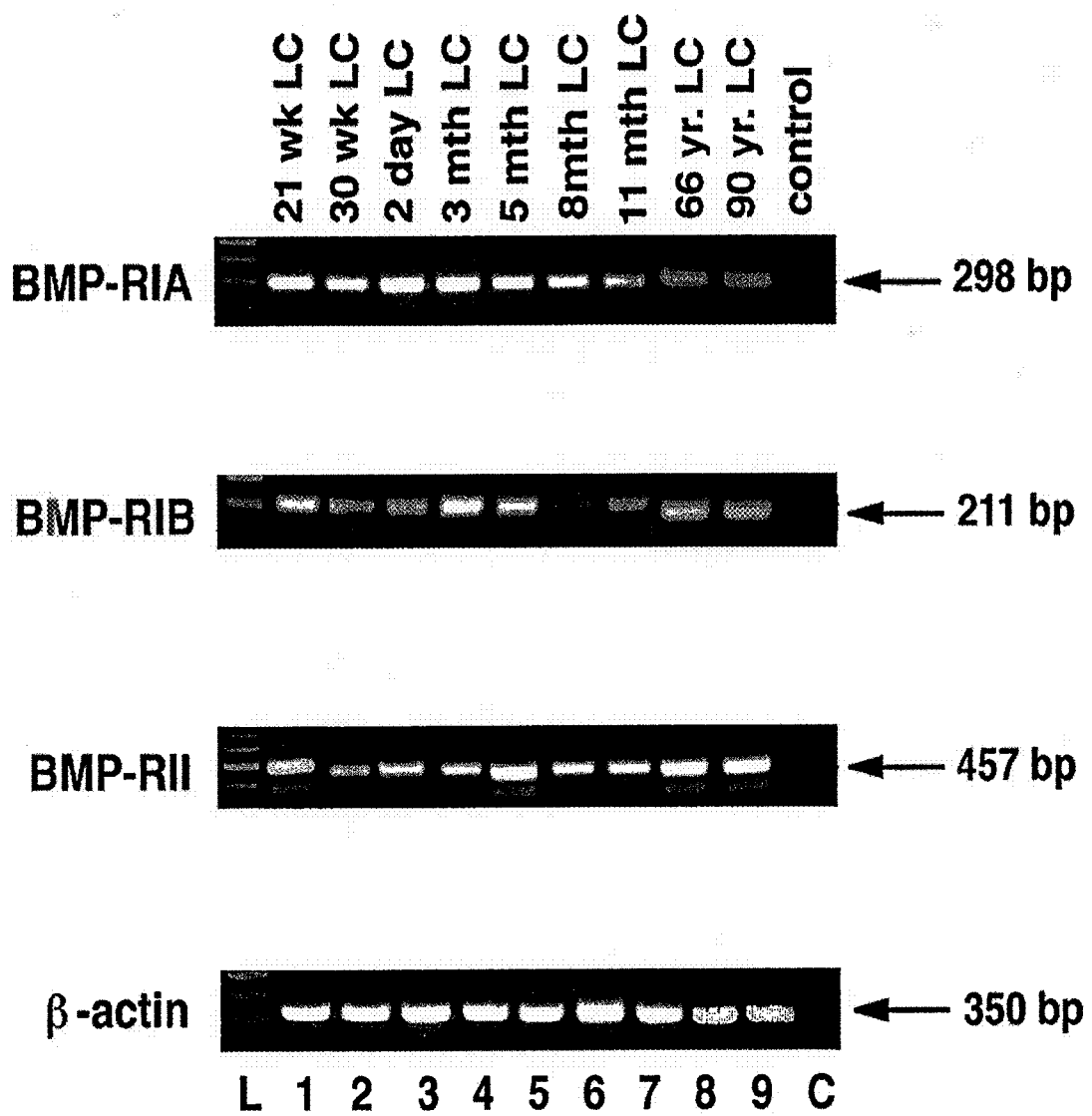
FIG. 11. BMP receptor expression in human lamina cribrosa cell lines. Ethidium bromide-stained agarose gel of PCR products from cDNA samples generated from RT-PCR analysis of human lamina cribrosa cells (lanes 1-9). L=base pair markers. C=PCR negative control lane. β-actin was used as a positive RT-PCR control.

FIG. 11 shows the amplification products of expected size for BMP-RIA, BMP-RIB, and BMP-RII primer pairs in cultured human LC cells. All LC cell lines expressed message for each BMP receptor. Southern blots using specific probes verified that these were the expected PCR products. Control reactions without cDNA did not result in amplification products (FIG. 11, lane C) indicating that reagents and primers were free of DNA or RNA contamination.

Figure 12:
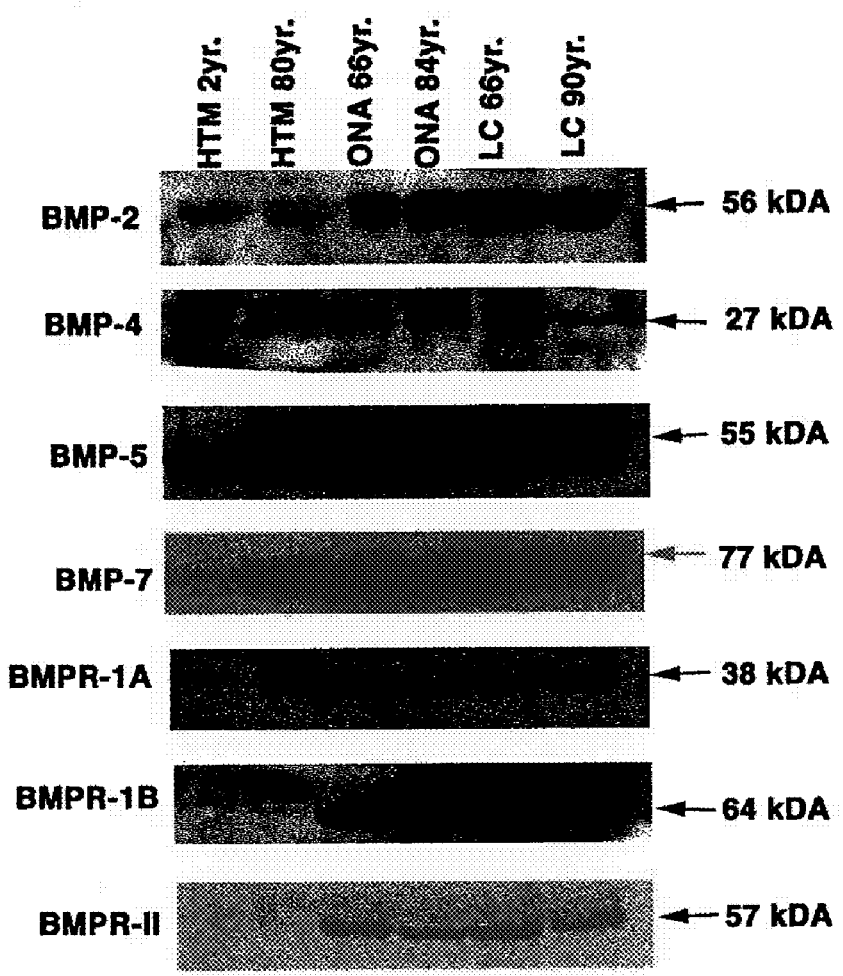
FIG. 12. Western immunoblot of BMP and BMP receptor expression in cultured human TM cells, optic nerve head astrocytes (ONA), and lamina cribrosa cells. Chemiluminescent detection of BMP proteins and BMP receptors in human trabecular meshwork cells (lanes 1-2), ONH astrocytes (lanes 3-4), and lamina cribrosa cells (lanes 5-6). Protein size indicated in kDa.

Expression of BMP proteins and BMP receptor proteins in human TM and ONH cells and tissues: FIG. 12 represents chemiluminescent immunoblot detection of BMP-2, BMP-4, BMP-5, BMP-7, BMP-RIA, BMP-RIB, and BMP-RII proteins in human TM and ONH cells and tissues. All cell lines studied expressed the respective BMP proteins. The BMP proteins were detected in cell lines the following molecular weights: 54-56 kDa for BMP-2, 25-27 kDa for BMP-4, 55-57 kDa for BMP-5, and 77 kDa for BMP-7. Multiple bands were detected for BMP-2 and BMP-4, which most likely represent glycosylated, and partially glycosylated forms of these BMPs as seen in other studies. However, we did not do glycosylation studies as they were beyond the scope of this study. The BMP receptor proteins were detected in cell lines at molecular weights: 38 kDa for BMP-RIA, 64 kDa for BMP-RIB, and 57 kDa for BMP-RII. Multiple bands were detected for BMP-RIB and BMP-RII in the TM cells, which most likely represent glycosylated, and partially glycosylated forms as seen in other studies. The expression levels of proteins for the BMP receptors appeared to be lower in the TM cells compared to ONH cells. For example BMP-RII was not detected in TM cells and BMP-RIB was greatly reduced.

Figure 13:
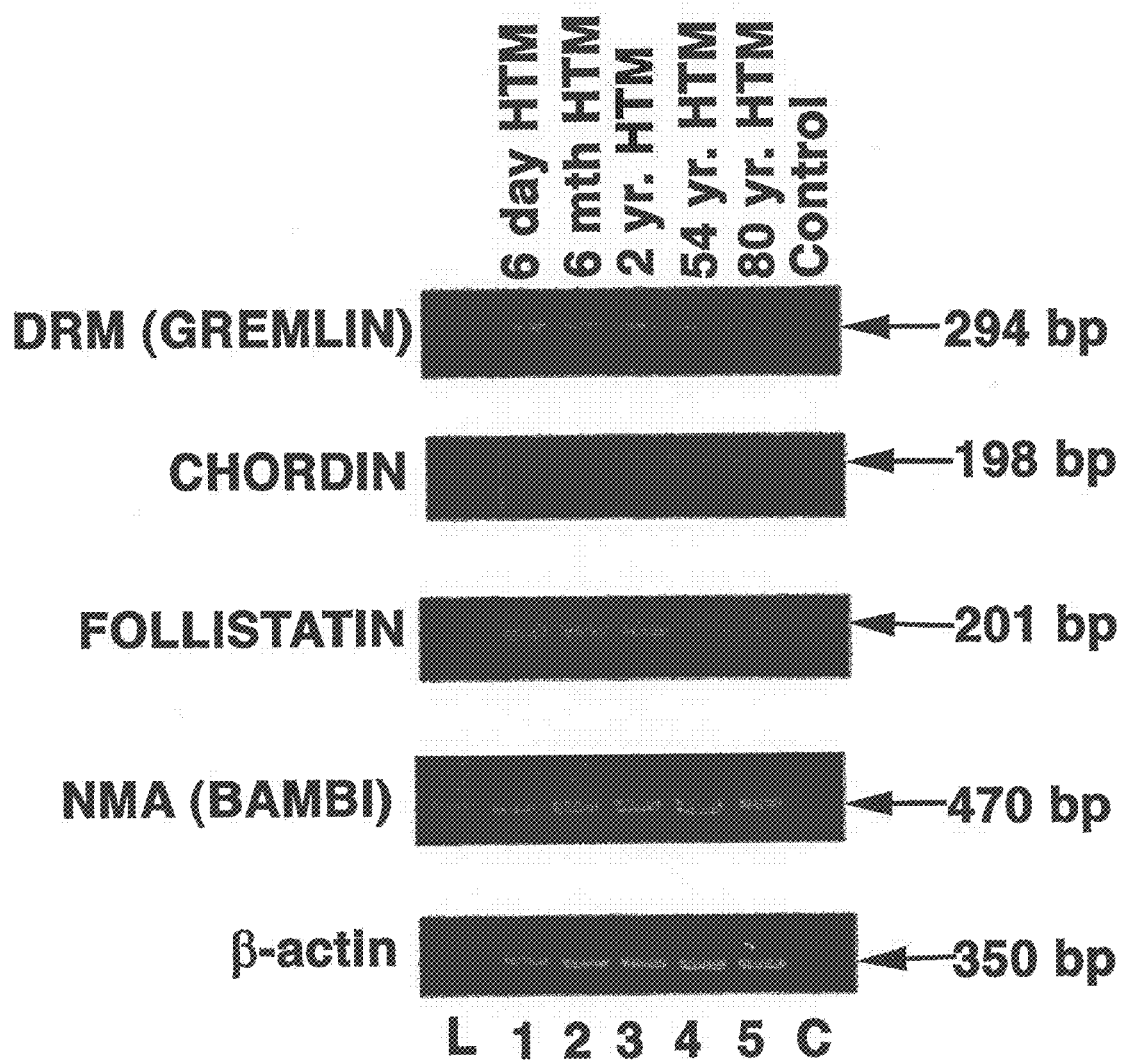
FIG. 13. BMP associated protein mRNA expression in human TM cells. Ethidium bromide-stained agarose gel of PCR products from cDNA samples generated from RT-PCR analysis of human TM cells (lanes 1-5). L=base pair markers. C=PCR negative control lane. β-actin was used as a positive RT-PCR internal control.

Expression of BMP associated protein mRNAs in cultured human TM cells and in human ONH cells: Amplification products of expected size for BMP associated protein primer pairs in human TM cell lines are shown in FIG. 13. Human TM cell lines expressed message for DRM (gremlin), chordin, follistatin, and NMA (BAMBI). Southern blots using specific probes verified that these were the expected PCR products. There was no apparent difference in message expression between cell lines. All human TM cells examined failed to express mRNA for the BMP associated proteins noggin and Cer-1. Control reactions without cDNA did not result in amplification products indicating that reagents and primers were free of DNA or RNA contamination.

Figure 14:
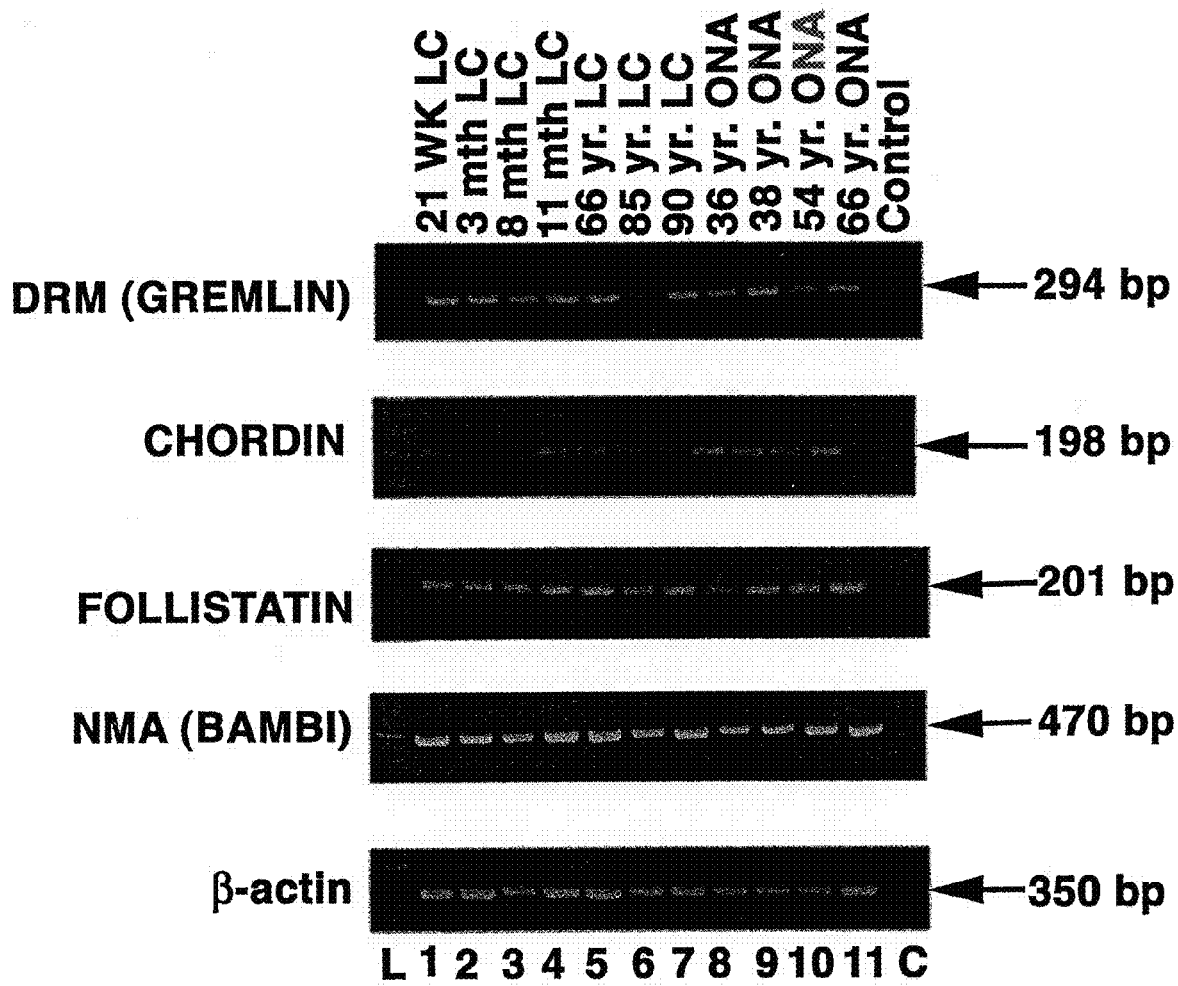
FIG. 14. BMP associated protein mRNA expression in human lamina cribrosa cells and ONH astrocytes. Ethidium bromide-stained agarose gel of PCR products from cDNA samples generated from RT-PCR analysis of lamina cribrosa (LC) cells (lanes 1-7) and ONH astrocytes (ONA) (lanes 8-11). L=base pair markers. C=PCR negative control lane. β-actin was used as a positive RT-PCR internal control.

Amplification products of expected size for BMP associated protein primer pairs in ONH astrocytes and LC cell lines are shown in FIG. 14. All ONH astrocytes and LC cell lines expressed message for DRM (gremlin), follistatin and NMA (BAMBI). Southern blots using specific probes verified that these were the expected PCR products. The majority of LC cells and ONH astrocytes expressed message for chordin. All human ONH astrocytes and LC cells examined failed to express mRNA for the BMP associated proteins noggin and Cer-1. Control reactions without cDNA did not result in amplification products indicating that reagents and primers were free of DNA and RNA contamination.

Figure 15:
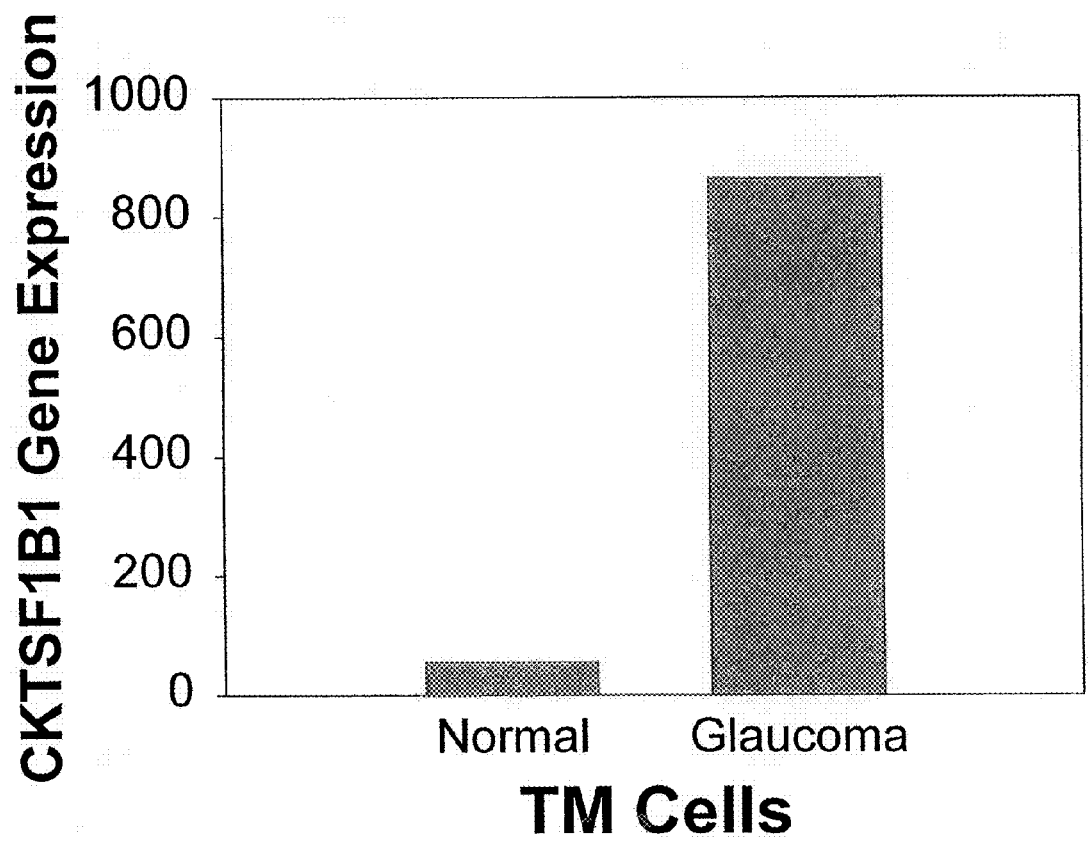
FIG. 15. Illustrates increased expression of the BMP antagonist gremlin (CKTSF1B1) in glaucomatous TM cells. Gene expression was assessed using Affymetrix gene arrays (Affymetrix gene chip U133A).

FIG. 15 shows increased expression of the BMP antagonist gremlin (CKTSF1B1) in glaucomatous TM cells. Gene expression was assessed using Affymetrix gene arrays (Affymetrix gene chip U133A).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Books

Birren, et al., GENOME ANALYSIS, Vol. 2, (1998).
Clark A F, Browder S, Steely H T, Wilson K, Cantu-Crouch D, McCartney M D, "*Cell biology of the human lamina cribrosa,*" In Drance S M (ed). OPTIC NERVE IN GLAUCOMA. Kugler Publications, New York: pp. 79-105 (1995b).
Cummings, Michael R., HUMAN HEREDITY, Fourth Edition, (1997).
Grierson I, Calthorpe C M, "*Characteristics of meshwork cells and age changes in the outflow system of the eye: their relevance to primary open angle glaucoma.*" In Mills K B (ed). GLAUCOMA. PROCEEDINGS OF THE FOURTH INTERNATIONAL SYMPOSIUM OF THE NORTHERN EYE INSTITUTE, Manchester, UK, New York, Pergamon: pp. 12-31 (1988).
Hernandez M, Gong H, "*Extracellular matrix of the trabecular meshwork and optic nerve head.*" in Ritch R., Shields, M. B., Krupin, T. (eds). THE GLAUCOMAS, $2^{nd}$ ed. St Louis: Mosby-Year; pp. 213-249 (1996).
Jorde, et al., MEDICAL GENETICS, Second Edition, (1999).
Lutjen-Drecoll E., Rohen J. W., "*Morphology of aqueous outflow pathways in normal and glaucomatous eyes,*" in Ritch R., Shields, M. B., Krupin, T. (eds). THE GLAUCOMAS, 2nd ed. St Louis: Mosby-Year; pp. 89-123 (1996).

Strachan, et al., HUMAN MOLECULAR GENETICS, (1996).

Tripathi R C, Borisuth N S, Li, J, Tripathi B J, "*Clinical implications of aqueous humor growth factors in glaucoma,*" in Ritch R., Shields, M. B. Krupin, T. (eds). THE GLAUCOMAS, 2nd ed. St Louis: Mosby-Year; pp. 71-87 (1996).

Varma R, Minckler D, "*Anatomy and pathophysiology of the retina and optic nerve.*" in Ritch R., Shields, M. B. Krupin, T. (eds). THE GLAUCOMAS, 2nd ed. St Louis: Mosby-Year; pp. 139-175 (1996).

Vaughan, D. et al., In: GENERAL OPHTHALMOLOGY, Appleton & Lange, Norwalk, Conn., pp. 213-230 (1992).

Other Publications

Agarwal et al, *IOVS* 38(4):S563 (1997)

Agarwal R, Talati M, Lambert W, Clark A F, Wilson S E, Agarwal N, Wordinger R J, "*FAS-activated apoptosis and other apoptosis mediators in human trabecular meshwork cells,*" *Exp. Eye Res.* 68:583-590 (1999).

Astrom, A. K. Jin, D., Imamura, T., Roijer, E., Rosenzweig, B., Miyazono, K., ten Dijke, P., Stenman, G., *Mamm. Genome* 10(3):299-302 (1999).

Attisano L, Tuen Lee-Hoeflich S, "*The Smads,*" *Genome Biol.* 2:REVIEWS3010 (2001).

Bengtsson, B., *Br. J. Ophthalmol.* 73:483-487 (1989).

Chang B, Smith R S, Peters M, Savinova D V, Hawes N L, Zabalata A, Nusinowitz S, Martin J E, Davisson M L, Sepko C L, Hogan B M L, John S W M, "*Haploinsufficient Bmp4 ocular phenotypes include anterior segment dysgenesis with elevated intraocular pressure,*" *BMC Genetics* 2:18 (2001).

Chundru R K, Agarwal R, Wordinger R J, Whitson J T, "*Detection of neurotrophins in human aqueous humor,*" *Invest. Ophthalmol. Vis. Sci.* 41:S236 (2000).

Clark A F, Kawase K, English-Wright S, Lane D, Steely H T, Yamamoto T, Kitazawa Y, Kwon Y H, Fingert J H, Swiderski R E, Mullins R F, Hageman G S, Alward W L M, Sheffield V C, Stone E M, "*Expression of the glaucoma gene myocilin (MYOC) in the human optic nerve head,*" *FASEB J.* 15:1251-1253 (2001).

Clark A F, Lane D, Wilson K, Miggans S T, McCartney M D, "*Inhibition of dexamethasone-induced cytoskeletal changes in cultured human trabecular meshwork cells by tetrahydrocortisol,*" *Invest. Ophthalmol. Vis. Sci.* 35:805-813 (1996).

Clark A F, Miggans S T, Wilson K, Browder S, McCartney M D, "*Cytoskeletal changes in cultured human glaucoma trabecular meshwork cells,*" *J. Glaucoma* 4:183-188 (1995c).

Clark A F, Steely H T, Dickerson J E, English-Wright S, Stropki K, McCartney M D, Jacobson N, Shepard A R, Clark J I, Matsushima H, Peskind E R, Leverenz J B, Wilkinson C W, Swiderski R E, Fingert J H, Sheffield V C, Stone E M, "*Glucocorticoid induction of the glaucoma gene MYOC in human and monkey trabecular meshwork cells and tissues,*" *Invest. Ophthalmol. Vis. Sci.* 42:1769-1780 (2001b).

Clark A F, Wilson K, de Kater A W, Allingham R R, McCartney M D, "*Dexamethasone-induced ocular hypertension in perfusion-cultured human eyes,*" *Invest. Ophthalmol. Vis. Sci.* 36:478-489 (1995a).

Clark A F, Wilson K, McCartney M D, Miggans S T, Kunkle M, Howe W, "*Glucocorticoid-induced formation of cross-linked actin networks in cultured human trabecular meshwork cells,*" *Invest. Ophthalmol. Vis. Sci.* 35:281-294 (1994).

Dickerson J E, Steely H T, English-Wright S L, Clark A F, "*The effect of dexamethasone on integrin and laminin expression in cultured human trabecular meshwork cells,*" *Exp. Eye Res.* 66:731-738 (1998).

Dudley A T, Lyons K M, Robertson E J, "*A requirement for bone morphogenic protein-7 during development of the mammalian kidney and eye,*" *Genes Dev.* 9:2795-2807 (1995).

Furuta Y, Hogan B L, "*BMP4 is essential for lens induction in the mouse embryo,*" *Genes Dev.* 12:3764-3775 (1998).

Greve, M. et al., *Can. J. Ophthamol.* 28:201-206 (1993).

Giguère et al., *Cell* 46:645-652 (1986).

Hernandez M R, Andrzejewska W M, Neufeld A H, "*Changes in the extracellular matrix of the human optic nerve head in primary open-angle glaucoma,*" *Am. J. Ophthalmol.* 109:180-188 (1990).

Hernandez M R, Pena J D, "*The optic nerve head in glaucomatous optic neuropathy,*" *Arch Ophthalmol.* 115:389-395 (1997).

Hitchings, R. A., *Br. J. Ophthamol.* 77:326 (1993).

Hogan B L, "*Bone morphogenic proteins: multifunctional regulators of vertebrate development,*" *Genes Dev.* 10:1580-1594 (1996).

Hu D N, Ritch R, "*Hepatocyte growth factor is increased in the aqueous humor of glaucomatous eyes,*" *J. Glaucoma* 10:152-157 (2001).

Inatani M, Tanihara H, Katsuta H, Honjo M, Kido N, Honda Y, "*Transforming growth factor beta 2 levels in aqueous humor of glaucomatous eyes,*" *Graefes Arch. Clin. Exp. Ophthalmol.* 239:109-113 (2001).

Itoh et al., *Eur. J. Biochem.* 267:6954-6967 (2000).

Jena N, Martin-Seisdedos C, McCue P, Croce C M, "*BMP7 null mutation in mice: developmental defects in skeleton, kidney, and eye,*" *Exp. Cell Res.* 230:28-37 (1997).

Kawabata et al., *Cytokine & Growth Factor Review*, 9:49-61 (1998).

Kerrigan L A, Zack D J, Quigley H A, Smith S D, Pease M E, "*TUNEL-positive ganglion cells in human primary open-angle glaucoma,*" *Arch. Ophthalmol.* 115:1031-1035 (1997).

Lambert et al., *IOVS* 38(4):S162 (1997).

Lambert W, Agarwal R, Howe W, Clark A F, Wordinger R J, "*Neurotrophin and neurotrophin receptor expression by cells of the human lamina cribrosa,*" *Invest. Ophthalmol. Vis. Sci.*, 42:2315-2323 (2001).

Leske, M. C. et al., *Amer. J. Epidemiol.* 113:1843-1846 (1986).

Liu et al., *IOVS* 40(4):S673 (1999).

Liu Y, Belayev L, Zhao W, Busto R, Saul I, Alonso O, Ginsberg M D, "*The effect of bone morphogenic protein-7 (BMP-7) on functional recovery, local cerebral glucose utilization and blood flow after transient focal cerebral ischemia in rats,*" *Brain Res.* 905:81-90 (2001).

Liu X, Lambert W, Agarwal R, Talati M, Cross W, Clark A F, Wordinger R J, "*Human trabecular meshwork cells express the ciliary neurotrophic factor (CNTF) tripartate receptor complex,*" *Exp. Eye Res.* 72:711-717 (2001).

Luo G, Gofmann C, Bronckers A L, Sohocki M, Bradley A, Karsenty G, "*BMP-7 is an inducer of nephrogenesis, and is also required for eye development and skeletal patterning,*" *Genes Dev.* 9:2808-2820 (1995).

McMahon, R., Murphy, M., Clarkson, M., Taal, M., Mackenzie, H. S., Godson, C., Martin, F., Brady, H. R., *J. Biol. Chem.* 275(14):9901-9904 (2000).

Miyazono, *J. Cell Science,* 113:1101-1109 (2000).

Mohan R R, Kim W J, Mohan R R, Chen L, Wilson S E, "*Bone morphogenic proteins 2 and 4 and their receptors in the adults human cornea,*" *Invest. Ophthalmol. Vis. Sci.* 39:2626-2636 (1998).

Morrison J C, Dorman-Pease M E, Dunkelberger G R, Quigley H A, "*Optic nerve head extracellular matrix in primary optic atrophy and experimental glaucoma,*" *Arch. Ophthalmol.* 108:1020-1024 (1990).

Murphy, M., Godson, C., Cannon, S., Kato, S., Mackenzie, H. S., Martin, F., Brady, H. R., *J. Biol. Chem.* 274(9):5830-5834 (1999).

Nickel J, Dreyer M K, Kirsch T, Sebold W, "*The crystal structure of BMP-2:BMPR-1A complex and the generation of BMP-2 antagonists,*" *J. Bone & Joint Surgery* 83-A (suppl 1):S1-S7 (2001).

Nohno, T., Ishikawa, T., Saito, T., Hosokawa, K., Noji, S., Wolsing, D. H., Rosenbaum, J. S., *J. Biol. Chem.* 270(38): 22522-22526 (1995).

Nonner D, Barrett E F, Kaplan P, Barrett J N, "*Bone morphogenic proteins (BMP6 and BMP7) enhance the protective effect of neurotrophins on cultured septal cholinergic neurons during hypoglycemia,*" *J. Neurochem.* 77:691-699 (2001).

Obata H, Kaji Y, Yamada H, Kato M, Tsuru T, Yamashita H, "*Expression of transforming growth factor-beta superfamily receptors in rat eyes,*" *Acta. Ophthalmol. Scand.* 77:151-156 (1999).

Pang I-H, McCartney M D, Steely H T, Clark A F, "*Human ocular perfusion organ culture: a versatile ex vivo model for glaucoma research,*" *J. Glaucoma* 9:468-479 (2000).

Pena J D, Taylor A W, Ricard C S, Vidal I, Hernandez M R, "*Transforming growth factor beta isoforms in human optic nerve heads,*" *Br. J. Ophthalmol.* 83:209-218 (1999).

Picht G, Welge-Luessen U, Grehn F, Lutjen-Drecoll E, "*Transforming growth factor beta 2 levels in the aqueous humor in different types of glaucoma and the relation to filtering bleb development,*" *Graefes Arch. Clin. Exp. Ophthalmol.* 239:199-207 (2001).

Quigley H A, McKinnon S J, Zack D J, Pease M E< Kerrigan-Baumrind L A, Kerrigan D F, Mitchell R S, "*Retrograde axonal transport of BDNF in retinal ganglion cells is blocked by acute IOP elevation in rats,*" *Invest. Ophthalmol. Vis. Sci.* 41:3460-3466 (2000).

Quigley H A, "*Neuronal death in glaucoma,*" *Prog. Retin. Eye Res.* 18:39-57 (1999).

Quigley H A, Nickells R W, Kerrigan L A, Pease M E, Thibault D J, Zack D J, "*Retinal ganglion cell death in experimental glaucoma and after axotomy occurs by apoptosis,*" *Invest. Ophthalmol. Vis. Sci.* 36:774-786 (1995).

Reddi A H, "*Bone morphonegetic proteins: an unconventional approach to isolation of first mammalian morphogens,*" *Cytokine Growth Factor Rev.* 8:11-20 (1997).

Reddi A H, "*Bone morphogenic proteins and skeletal development: the kidney-bone connection,*" *Pediatr. Nephrol.* 14:598-601 (2000).

Rohen J W, "*Why is intraocular pressure elevated in chronic simple glaucoma? Anatomical considerations.*" *Ophthalmology* 90:758-765 (1983).

Steely H T, Browder S L, Julian M B, Miggans S T, Wilson K L, Clark A F, "*The effects of dexamethasone on fibronectin expression in cultured human trabecular meshwork cells,*" *Invest. Ophthalmol. Vis. Sci.* 33: 2242-2250 (1992).

Steely H T, English-Wright S L, Clark A F, "*Similarity of protein expression in trabecular meshwork and lamina cribrosa: implications for glaucoma,*" *Exp. Eye Res.* 70:17-30 (2000).

Strong, N. P., *Ophthal. Physiol. Opt.* 12:3-7 (1992).

ten Dijke, P. P., Ichijo, H., Franzen, P., Schulz, P., Saras, J., Toyoshima, H., Heldin, C. H., Miyazono, K., *Oncogene* 8(10):2879-2887 (1993).

Tripathi R C, Borisuth N S, Kolli S P, Tripathi B J, "*Trabecular cells express receptors that bind TGF-beta 1 and TGF-beta 2: a qualitative and quantitative characterization,*" *Invest. Ophthalmol. Vis. Sci.* 34:260-263 (1993b).

Tripathi R C, Borisuth N S, Tripathi B J, "*Detection, quantification, and significance of basic fibroblast growth factor in the aqueous humor of man, cat, dog and pig,*" *Exp. Eye Res.* 54:447-454 (1992).

Tripathi R C, Borisuth N S, Tripathi B J, Fang V S, "*Analysis of human aqueous humor for epidermal growth factor,*" *Exp. Eye Res.* 53:407-409 (1991).

Tripathi R C, Chan W F, Li J, Tripathi B J, "*Trabecular cells express the TFG-beta 2 gene and secrete the cytokine,*" *Exp. Eye Res.* 58:523-528 (1994a).

Tripathi R C, Li J, Borisuth N S, Tripathi B J, "*Trabecular cells of the eye express messenger RNA for transforming growth factor-beta 1 and secrete this cytokine,*" *Invest. Ophthalmol. Vis. Sci.* 34:2562-2569 (1993a).

Tripathi R C, Li J, Chan W F, Tripathi B J, "*Aqueous humor in glaucomatous eyes contains an increased level of TFG-beta 2,*" Exp. Eye Res. 59:723-727 (1994c).

Tripathi R C, Li J, Tripathi B J, "*Immunolocalization of bFGF in the trabecular meshwork and detection of its mRNA in trabecular cells,*" *Exp. Eye Res.* 58:503-507 (1994b).

Trousse F, Esteve P, Bovolenta P, "BMP4 *mediates apoptotic cell death in the developing chick eye,*" *J. Neurosci.* 21:1292-1301 (2001).

Tuck, M. W. et al., *Ophthal. Physiol. Opt.* 13:227-232 (1993).

Vernon, S. A., *Eye* 7:134-137 (1993).

Von Bubnoff A, Cho K W, "*Intracellular BMP signaling regulation in vertebrates: pathway or network?*" *Dev. Biol.* 239:1-14 (2001).

Wang W-H, McNatt L G, Shepard A R, Jacobson N, Nishimura D Y, Stone E M, Sheffield V C, Clark A F, "*Optimal procedure for extracting RNA from human ocular tissues and expression profiling of the congenital glaucoma gene FOXC1 using quantitative RT-PCR,*" *Molecular Vision* 7:89-94 (2001).

Wilson K, McCartney M D, Miggans S T, Clark A F, "*Dexamethasone induced ultrastructural changes in cultured human trabecular meshwork cells,*" *Current Eye Research* 12:783-793 (1993).

Wordinger et al., *IOVS* 40(4):S504 (1999a).

Wordinger R J, Agarwal R, Talati M, Fuller J, Lambert W, Clark A F, "*Expression of bone morphogenic proteins (BMP), BMP receptors, and BMP associated proteins in human trabecular meshwork and optic nerve head cells and tissues,*" *Molec. Vision* 8:241-256 (2002).

Wordinger R J, Clark A F, Agarwal R, Lambert W, McNatt L, Wilson S E, Qu E, Fung B K-K, "*Cultured human trabecular meshwork cells express functional growth factor receptors,*" *Invest. Ophthalmol. Vis. Sci.* 39: 1575-1589 (1998).

Wordinger R J, Clark A F, Agarwal R, Lambert W, Wilson S E, "*Expression of alternatively spliced growth factor receptor isoforms in the human trabecular meshwork,*" *Invest. Ophthalmol. Vis. Sci.* 40:242-247 (1999b).

Wordinger R J, Lambert W, Agarwal R, Talati M, Clark A F, "*Human trabecular meshwork cells secrete neurotrophins and express neurotrophin receptors (Trk),*" *Invest. Ophthalmol. Vis. Sci.* 41:3833-3841 (2000).

Yamashita H, Ten Dijke P, Heldin C H, Miyazono K, "*Bone morphogenic protein receptors,*" *Bone* 19:569-574 (1996).

You L, Kruse F E, Pohl J, Volcker H E, "Bone morphogenic proteins and growth and differentiation factors in the human cornea," Invest. Ophthalmol. Vis. Sci. 40:296-311 (1999).

Zhang D, Mehler M F, Song Q, Kessler J A, "Development of bone morphogenic protein receptors in the nervous system and possible roles in regulating trkC expression," J. Neurosci. 18:3314-3326 (1998).

We claim:

1. A method for treating glaucoma comprising administering to a patient in need thereof a composition comprising a gremlin antagonist, wherein the gremlin antagonist is an antibody that binds to gremlin.

* * * * *

SEQUENCE LISTING

<160> NUMBER OF SEQ ID NOS: 56

<210> SEQ ID NO 1
<211> LENGTH: 1547
<212> TYPE: DNA
<213> ORGANISM: homo sapiens

<400> SEQUENCE: 1

```
ggggacttct tgaacttgca gggagaataa cttgcgcacc ccactttgcg ccggtgcctt      60
tgccccagcg gagcctgctt cgccatctcc gagcccacc gccctccac tcctcggcct      120
tgcccgacac tgagacgctg ttcccagcgt gaaaagagag actgcgcggc cggcacccgg    180
gagaaggagg aggcaaagaa aaggaacgga cattcggtcc ttgcgccagg tcctttgacc    240
agagtttttc catgtggacg ctctttcaat ggacgtgtcc ccgcgtgctt cttagacgga    300
ctgcggtctc ctaaaggtcg accatggtgg ccgggacccg ctgtcttcta gcgttgctgc    360
ttccccaggt cctcctgggc ggcgcggctg gcctcgttcc ggagctgggc cgcaggaagt    420
tcgcggcggc gtcgtcgggc cgcccctcat cccagccctc tgacgaggtc ctgagcgagt    480
tcgagttgcg gctgctcagc atgttcggcc tgaaacagag acccacccc agcagggacg    540
ccgtggtgcc cccctacatg ctagacctgt atcgcaggca ctcaggtcag ccgggctcac    600
ccgccccaga ccaccggttg gagagggcag ccagccgagc caacactgtg cgcagcttcc    660
accatgaaga atctttggaa gaactaccag aaacgagtgg gaaaacaacc cggagattct    720
tctttaattt aagttctatc cccacggagg agtttatcac ctcagcagag cttcaggttt    780
tccgagaaca gatgcaagat gctttaggaa acaatagcag tttccatcac cgaattaata    840
tttatgaaat cataaaacct gcaacagcca actcgaaatt ccccgtgacc agacttttgg    900
acaccaggtt ggtgaatcag aatgcaagca ggtgggaaag ttttgatgtc accccgctg    960
tgatgcggtg gactgcacag gacacgcca accatggatt cgtggtggaa gtgccccact   1020
tggaggagaa acaaggtgtc tccaagagac atgttaggat aagcaggtct ttgcaccaag   1080
atgaacacag ctggtcacag ataaggccat tgctagtaac ttttggccat gatggaaaag   1140
ggcatcctct ccacaaaaga gaaaaacgtc aagccaaaca caaacagcgg aaacgcctta    1200
agtccagctg taagagacac cctttgtacg tggacttcag tgacgtgggg tggaatgact   1260
ggattgtggc tcccccgggg tatcacgcct tttactgcca cggagaatgc ccttttcctc   1320
tggctgatca tctgaactcc actaatcatg ccattgttca gacgttggtc aactctgtta    1380
actctaagat tcctaaggca tgctgtgtcc cgacagaact cagtgctatc tcgatgctgt    1440
accttgacga gaatgaaaag gttgtattaa agaactatca ggacatggtt gtggagggtt   1500
gtgggtgtcg ctagtacagc aaaattaaat acataaatat atatata                1547
```

<210> SEQ ID NO 2
<211> LENGTH: 396
<212> TYPE: PRT
<213> ORGANISM: homo sapiens

<400> SEQUENCE: 2

Met Val Ala Gly Thr Arg Cys Leu Leu Ala Leu Leu Leu Pro Gln Val

```
              1               5                  10                 15
Leu Leu Gly Gly Ala Ala Gly Leu Val Pro Glu Leu Gly Arg Arg Lys
                20                  25                 30

Phe Ala Ala Ser Ser Gly Arg Pro Ser Ser Gln Pro Ser Asp Glu
                35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                      70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
                100                 105                 110

His His Glu Glu Ser Leu Glu Glu Leu Pro Glu Thr Ser Gly Lys Thr
                115                 120                 125

Thr Arg Arg Phe Phe Phe Asn Leu Ser Ser Ile Pro Thr Glu Glu Phe
                130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
                180                 185                 190

Asp Thr Arg Leu Val Asn Gln Asn Ala Ser Arg Trp Glu Ser Phe Asp
                195                 200                 205

Val Thr Pro Ala Val Met Arg Trp Thr Ala Gln Gly His Ala Asn His
                210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
                260                 265                 270

Gly His Pro Leu His Lys Arg Glu Lys Arg Gln Ala Lys His Lys Gln
                275                 280                 285

Arg Lys Arg Leu Lys Ser Ser Cys Lys Arg His Pro Leu Tyr Val Asp
                290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
                340                 345                 350

Asn Ser Lys Ile Pro Lys Ala Cys Cys Val Pro Thr Glu Leu Ser Ala
                355                 360                 365

Ile Ser Met Leu Tyr Leu Asp Glu Asn Glu Lys Val Val Leu Lys Asn
                370                 375                 380

Tyr Gln Asp Met Val Val Glu Gly Cys Gly Cys Arg
385                 390                 395

<210> SEQ ID NO 3
<211> LENGTH: 1946
<212> TYPE: DNA
<213> ORGANISM: homo sapiens
```

<400> SEQUENCE: 3

```
gaaagcgagg gagggaaaga ggaggaagga agatgcgaga aggcagagga ggagggaggg      60
agggaaggag cgcggagccc ggcccggaag ctaggtgagt gtggcatccg agctgaggga     120
cgcgagcctg agacgccgct gctgctccgg ctgagtatct agcttgtctc cccgatggga     180
ttcccgtcca agctatctcg agcctgcagc gccacagtcc ccggccctcg cccaggttca     240
ctgcaaccgt tcagaggtcc ccaggagctg ctgctggcga gcccgctact gcagggacct     300
atggagccat tccgtagtgc catcccgagc aacgcactgc tgcagcttcc ctgagccttt     360
ccagcaagtt tgttcaagat ggctgtcaa gaatcatgga ctgttattat atgccttgtt      420
ttctgtcaag acaccatgat tcctggtaac gaatgctga tggtcgtttt attatgccaa      480
gtcctgctag gaggcgcgag ccatgctagt ttgatacctg agacggggaa gaaaaaagtc     540
gccgagattc agggccacgc gggaggacgc cgctcagggc agagccatga gctcctgcgg     600
gacttcgagg cgacacttct gcagatgttt gggctgcgcc gccgcccgca gcctagcaag     660
agtgccgtca ttccggacta catgcgggat ctttaccggc ttcagtctgg ggaggaggag     720
gaagagcaga tccacagcac tggtcttgag tatcctgagc gccggccag ccgggccaac      780
accgtgagga gcttccacca cgaagaacat ctggagaaca tcccagggac cagtgaaaac     840
tctgcttttc gtttcctctt taacctcagc agcatccctg agaacgaggc gatctcctct     900
gcagagcttc ggctcttccg ggagcaggtg accagggcc ctgattggga aggggcttc      960
caccgtataa acatttatga ggttatgaag cccccagcag aagtggtgcc tgggcacctc    1020
atcacacgac tactggacac gagactggtc caccacaatg tgacacggtg ggaaactttt    1080
gatgtgagcc ctgcggtcct tcgctggacc cgggagaagc agccaaacta tgggctagcc    1140
attgaggtga ctcacctcca tcagactcgg acccaccagg gccagcatgt caggattagc    1200
cgatcgttac ctcaagggag tgggaattgg gcccagctcc ggcccctcct ggtcaccttt    1260
ggccatgatg gccggggcca tgccttgacc cgacgccgga gggccaagcg tagccctaag    1320
catcactcac agcgggccag gaagaagaat aagaactgcc ggcgccactc gctctatgtg    1380
gacttcagcg atgtgggctg gaatgactgg attgtggccc caccaggcta ccaggccttc    1440
tactgccatg ggactgccc ctttccactg gctgaccacc tcaactcaac caaccatgcc     1500
attgtgcaga ccctggtcaa ttctgtcaat tccagtatcc ccaaagcctg ttgtgtgccc    1560
actgaactga gtgccatctc catgctgtac ctggatgagt atgataaggt ggtactgaaa    1620
aattatcagg agatggtagt agagggatgt gggtgccgct gagatcaggc agtccttgag    1680
gatagacaga tatacacacc acacacacac accacataca ccacacacac acgttcccat    1740
ccactcaccc acacactaca cagactgctt ccttatagct ggactttat ttaaaaaaaa      1800
aaaaaaaaaa atgaaaaaaa tccctaaaca ttcaccttga ccttatttat gactttacgt    1860
gcaaatgttt tgaccatatt gatcatatat tttgacaaaa tatatttata actacgtatt    1920
aaaagaaaaa aataaaatga gtcatt                                         1946
```

<210> SEQ ID NO 4
<211> LENGTH: 408
<212> TYPE: PRT
<213> ORGANISM: homo sapiens

<400> SEQUENCE: 4

```
Met Ile Pro Gly Asn Arg Met Leu Met Val Val Leu Leu Cys Gln Val
1               5                   10                  15
```

-continued

```
Leu Leu Gly Gly Ala Ser His Ala Ser Leu Ile Pro Glu Thr Gly Lys
             20                  25                  30

Lys Lys Val Ala Glu Ile Gln Gly His Ala Gly Gly Arg Arg Ser Gly
             35                  40                  45

Gln Ser His Glu Leu Leu Arg Asp Phe Glu Ala Thr Leu Leu Gln Met
         50                  55                  60

Phe Gly Leu Arg Arg Pro Gln Pro Ser Lys Ser Ala Val Ile Pro
 65                  70                  75                  80

Asp Tyr Met Arg Asp Leu Tyr Arg Leu Gln Ser Gly Glu Glu Glu
                 85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu His Leu Glu Asn
            115                 120                 125

Ile Pro Gly Thr Ser Glu Asn Ser Ala Phe Arg Phe Leu Phe Asn Leu
            130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
            195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
            275                 280                 285

Arg Ala Lys Arg Ser Pro Lys His His Ser Gln Arg Ala Arg Lys Lys
            290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
            355                 360                 365

Pro Lys Ala Cys Cys Val Pro Thr Glu Leu Ser Ala Ile Ser Met Leu
            370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 5
<211> LENGTH: 2153
```

<212> TYPE: DNA
<213> ORGANISM: homo sapiens

<400> SEQUENCE: 5

| | | | | | |
|---|---|---|---|---|---|
| ctggtatatt | tgtgcctgct | ggaggtggaa | ttaacagtaa | gaaggagaaa | gggattgaat | 60 |
| ggacttacag | gaaggatttc | aagtaaattc | agggaaacac | atttacttga | atagtacaac | 120 |
| ctagagtatt | attttacact | aagacgacac | aaaagatgtt | aaagttatca | ccaagctgcc | 180 |
| ggacagatat | atattccaac | accaaggtgc | agatcagcat | agatctgtga | ttcagaaatc | 240 |
| aggatttgtt | ttggaaagag | ctcaagggtt | gagaagaact | caaaagcaag | tgaagattac | 300 |
| tttgggaact | acagtttatc | agaagatcaa | cttttgctaa | ttcaaatacc | aaaggcctga | 360 |
| ttatcataaa | ttcatatagg | aatgcatagg | tcatctgatc | aaataatatt | agccgtcttc | 420 |
| tgctacatca | atgcagcaaa | aactcttaac | aactgtggat | aattggaaat | ctgagtttca | 480 |
| gctttcttag | aaataactac | tcttgacata | ttccaaaata | tttaaaatag | gacaggaaaa | 540 |
| tcggtgagga | tgttgtgctc | agaaatgtca | ctgtcatgaa | aaataggtaa | atttgttttt | 600 |
| tcagctactg | ggaaactgta | cctcctagaa | ccttaggttt | ttttttttt | aagaggacaa | 660 |
| gaaggactaa | aaatatcaac | ttttgctttt | ggacaaaaat | gcatctgact | gtattttac | 720 |
| ttaagggtat | tgtgggtttc | ctctggagct | gctgggttct | agtgggttat | gcaaaaggag | 780 |
| gtttgggaga | caatcatgtt | cactccagtt | ttatttatag | aagactacgg | aaccacgaaa | 840 |
| gacgggaaat | acaaagggaa | attctctcta | tcttgggttt | gcctcacaga | cccagaccat | 900 |
| tttcacctgg | aaaacaagcg | tcctctgcac | ctctctttat | gctggatctc | tacaatgcca | 960 |
| tgaccaatga | agaaaatcct | gaagagtcgg | agtactcagt | aagggcatcc | ttggcagaag | 1020 |
| agaccagagg | ggcaagaaag | ggatacccag | cctctcccaa | tgggtatcct | cgtcgcatac | 1080 |
| agttatctcg | gacgactcct | ctgaccaccc | agagtcctcc | tctagccagc | tccatgata | 1140 |
| ccaactttct | gaatgatgct | gacatggtca | tgagctttgt | caacttagtt | gaaagagaca | 1200 |
| aggatttttc | tcaccagcga | aggcattaca | agaatttcg | atttgatctt | acccaaattc | 1260 |
| ctcatggaga | ggcagtgaca | gcagctgaat | tccggatata | caaggaccgg | agcaacaacc | 1320 |
| gatttgaaaa | tgaaacaatt | aagattagca | tatatcaaat | catcaaggaa | tacacaaata | 1380 |
| gggatgcaga | tctgttcttg | ttagacacaa | gaaaggccca | agctttagat | gtgggttggc | 1440 |
| tgtctttga | tatcactgtg | accagcaatc | attgggtgat | taatccccag | aataatttgg | 1500 |
| gcttacagct | ctgtgcagaa | acaggggatg | acgcagtat | caacgtaaaa | tctgctggtc | 1560 |
| ttgtgggaag | acagggacct | cagtcaaaac | aaccattcat | ggtggccttc | ttcaaggcga | 1620 |
| gtgaggtact | tcttcgatcc | gtgagagcag | ccaacaaacg | aaaaaatcaa | aaccgcaata | 1680 |
| aatccagctc | tcatcaggac | tcctccagaa | tgtccagtgt | tggagattat | aacacaagtg | 1740 |
| agcaaaaaca | agcctgtaag | aagcacgaac | tctatgtgag | cttccgggat | ctgggatggc | 1800 |
| aggactggat | tatagcacca | gaaggatacg | ctgcatttta | ttgtgatgga | aatgttctt | 1860 |
| ttccacttaa | cgcccatatg | aatgccacca | accacgctat | agttcagact | ctggttcatc | 1920 |
| tgatgtttcc | tgaccacgta | ccaaagcctt | gttgtgctcc | aaccaaatta | aatgccatct | 1980 |
| ctgttctgta | ctttgatgac | agctccaatg | tcattttgaa | aaaatataga | aatatggtag | 2040 |
| tacgctcatg | tggctgccac | taatattaaa | taatattgat | aataacaaaa | agatctgtat | 2100 |
| taaggtttat | ggctgcaata | aaaagcatac | tttcagacaa | acagaaaaaa | aaa | 2153 |

<210> SEQ ID NO 6

<211> LENGTH: 454
<212> TYPE: PRT
<213> ORGANISM: homo sapiens

<400> SEQUENCE: 6

```
Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
            20                  25                  30

His Val His Ser Ser Phe Ile Tyr Arg Arg Leu Arg Asn His Glu Arg
        35                  40                  45

Arg Glu Ile Gln Arg Glu Ile Leu Ser Ile Leu Gly Leu Pro His Arg
    50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
                85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

Leu Ser Arg Thr Thr Pro Leu Thr Thr Gln Ser Pro Pro Leu Ala Ser
    130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
    210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
    290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser Ser His Gln Asp Ser Ser
                325                 330                 335

Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln
        355                 360                 365

Asp Trp Ile Ile Ala Pro Glu Gly Tyr Ala Ala Phe Tyr Cys Asp Gly
    370                 375                 380

Glu Cys Ser Phe Pro Leu Asn Ala His Met Asn Ala Thr Asn His Ala
```

```
                385                 390                 395                 400
Ile Val Gln Thr Leu Val His Leu Met Phe Pro Asp His Val Pro Lys
                    405                 410                 415

Pro Cys Cys Ala Pro Thr Lys Leu Asn Ala Ile Ser Val Leu Tyr Phe
                    420                 425                 430

Asp Asp Ser Ser Asn Val Ile Leu Lys Lys Tyr Arg Asn Met Val Val
            435                 440                 445

Arg Ser Cys Gly Cys His
        450

<210> SEQ ID NO 7
<211> LENGTH: 1878
<212> TYPE: DNA
<213> ORGANISM: homo sapiens

<400> SEQUENCE: 7
gggcgcagcg ggcccgtct gcagcaagtg accgacggcc gggacggccg cctgccccct         60
ctgccacctg ggcggtgcg ggcccggagc ccggagcccg ggtagcgcgt agagccggcg        120
cgatgcacgt gcgctcactg cgagctgcgg cgccgcacag cttcgtggcg ctctgggcac        180
ccctgttcct gctgcgctcc gccctggccg acttcagcct ggacaacgag gtgcactcga        240
gcttcatcca ccgcgcctc cgcagccagg agcggcggga gatgcagcgc gagatcctct        300
ccattttggg cttgccccac cgcccgcgcc cgcacctcca gggcaagcac aactcggcac        360
ccatgttcat gctggacctg tacaacgcca tggcggtgga ggagggcggc gggcccggcg        420
gccagggctt ctcctacccc tacaaggccg tcttcagtac ccagggcccc cctctggcca        480
gcctgcaaga tagccatttc ctcaccgacg ccgacatggt catgagcttc gtcaacctcg        540
tggaacatga caaggaattc ttccacccac gctaccacca tcgagagttc cggtttgatc        600
tttccaagat cccagaaggg gaagctgtca cggcagccga attccggatc tacaaggact        660
acatccggga acgcttcgac aatgagacgt tccggatcag cgtttatcag gtgctccagg        720
agcacttggg cagggaatcg gatctcttcc tgctcgacag ccgtacctc tgggcctcgg        780 aggagggctg gctggtgttt gacatcacag ccaccagcaa ccactgggtg tcaatccgc        840 ggcacaacct gggcctgcag ctctcggtgg agacgctgga tgggcagagc atcaacccca        900
agttggcggg cctgattggg cggcacgggc cccagaacaa gcagcccttc atggtggctt        960
tcttcaaggc cacggaggtc cacttccgca gcatccggtc cacggggagc aaacagcgca       1020
gccagaaccg ctccaagacg cccaagaacc aggaagccct gcggatggcc aacgtggcag       1080
agaacagcag cagcgaccag aggcaggcct gtaagaagca cgagctgtat gtcagcttcc       1140
gagacctggg ctggcaggac tggatcatcg cgcctgaagg ctacgccgcc tactactgtg       1200
agggggagtg tgccttccct ctgaactcct acatgaacgc caccaaccac gccatcgtgc       1260
agacgctggt ccacttcatc aacccggaaa cggtgcccaa gcctgctgt gcgcccacgc       1320 agctcaatgc catctccgtc ctctacttcg atgacagctc caacgtcatc ctgaagaaat       1380
acagaaacat ggtggtccgg gcctgtggct gccactagc cctccgagaa ttcagaccct       1440 tggggccaa gttttctgg atcctccatt gctcgccttg gcaggaacc agcagaccaa       1500 ctgcctttg tgagaccttc ccctcccta tccccaacttt aaaggtgtga gagtattagg       1560
aaacatgagc agcatatggc ttttgatcag tttttcagtg gcagcatcca atgaacaaga       1620
tcctacaagc tgtgcaggca aaacctagca ggaaaaaaaa acaacgcata agaaaaatg       1680 gccgggccag gtcattggct gggaagtctc agccatgcac ggactcgttt ccagaggtaa       1740
```

-continued

```
ttatgagcgc ctaccagcca ggccacccag ccgtgggagg aaggggggcgt ggcaagggggt    1800 gggcacattg gtgtctgtgc gaaaggaaaa ttgacccgga agttcctgta ataaatgtca    1860
caataaaacg aatgaatg                                                   1878
```

<210> SEQ ID NO 8
<211> LENGTH: 431
<212> TYPE: PRT
<213> ORGANISM: homo sapiens

<400> SEQUENCE: 8

```
Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
```

```
                    340                 345                 350
Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
        370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 9
<211> LENGTH: 22
<212> TYPE: DNA
<213> ORGANISM: homo sapiens

<400> SEQUENCE: 9
actgcggtct cctaaaggtc ga                                        22

<210> SEQ ID NO 10
<211> LENGTH: 21
<212> TYPE: DNA
<213> ORGANISM: homo sapiens

<400> SEQUENCE: 10
gctgacctga gtgcctgcga t                                         21

<210> SEQ ID NO 11
<211> LENGTH: 26
<212> TYPE: DNA
<213> ORGANISM: homo sapiens

<400> SEQUENCE: 11
gaatgctgat ggtcgttttt attatg                                    26

<210> SEQ ID NO 12
<211> LENGTH: 20
<212> TYPE: DNA
<213> ORGANISM: homo sapiens

<400> SEQUENCE: 12
agactgaagc cggtaaagat                                           20

<210> SEQ ID NO 13
<211> LENGTH: 26
<212> TYPE: DNA
<213> ORGANISM: homo sapiens

<400> SEQUENCE: 13
aagaggacaa gaaggactaa aaatat                                    26

<210> SEQ ID NO 14
<211> LENGTH: 25
<212> TYPE: DNA
<213> ORGANISM: homo sapiens

<400> SEQUENCE: 14
gtagagatcc agcataaaga gaggt                                     25

<210> SEQ ID NO 15
```

```
<211> LENGTH: 20
<212> TYPE: DNA
<213> ORGANISM: homo sapiens

<400> SEQUENCE: 15 agcccggta gcgcgtagag                                               20

<210> SEQ ID NO 16
<211> LENGTH: 21
<212> TYPE: DNA
<213> ORGANISM: homo sapiens

<400> SEQUENCE: 16
gcgccggtgg atgaagctcg a                                            21

<210> SEQ ID NO 17
<211> LENGTH: 24
<212> TYPE: DNA
<213> ORGANISM: homo sapiens

<400> SEQUENCE: 17
taaaggtgac agtacacagg aaca                                         24

<210> SEQ ID NO 18
<211> LENGTH: 23
<212> TYPE: DNA
<213> ORGANISM: homo sapiens

<400> SEQUENCE: 18
tctatgatgg caaagcaatg tcc                                          23

<210> SEQ ID NO 19
<211> LENGTH: 26
<212> TYPE: DNA
<213> ORGANISM: homo sapiens

<400> SEQUENCE: 19
tacaagcctg ccataagtga agaagc                                       26

<210> SEQ ID NO 20
<211> LENGTH: 25
<212> TYPE: DNA
<213> ORGANISM: homo sapiens

<400> SEQUENCE: 20
atcatcgtga aacaatatcc gtctg                                        25

<210> SEQ ID NO 21
<211> LENGTH: 26
<212> TYPE: DNA
<213> ORGANISM: homo sapiens

<400> SEQUENCE: 21
tcctctcatc agccatttgt cctttc                                       26

<210> SEQ ID NO 22
<211> LENGTH: 22
<212> TYPE: DNA
<213> ORGANISM: homo sapiens

<400> SEQUENCE: 22
agttactaca cattcttcat ag                                           22
```

-continued

```
<210> SEQ ID NO 23
<211> LENGTH: 20
<212> TYPE: DNA
<213> ORGANISM: homo sapiens

<400> SEQUENCE: 23
ctctgctcac tctgcacctg                                              20

<210> SEQ ID NO 24
<211> LENGTH: 20
<212> TYPE: DNA
<213> ORGANISM: homo sapiens

<400> SEQUENCE: 24
ccggtcacca tcaaaatagc                                              20

<210> SEQ ID NO 25
<211> LENGTH: 20
<212> TYPE: DNA
<213> ORGANISM: homo sapiens

<400> SEQUENCE: 25
atcaaccgct tctgttacgg                                              20

<210> SEQ ID NO 26
<211> LENGTH: 20
<212> TYPE: DNA
<213> ORGANISM: homo sapiens

<400> SEQUENCE: 26
atgcaacgac actgcttcac                                              20

<210> SEQ ID NO 27
<211> LENGTH: 20
<212> TYPE: DNA
<213> ORGANISM: homo sapiens

<400> SEQUENCE: 27
tgccacctga gaaaggctac                                              20

<210> SEQ ID NO 28
<211> LENGTH: 20
<212> TYPE: DNA
<213> ORGANISM: homo sapiens

<400> SEQUENCE: 28
acagacaggc tcatccgact                                              20

<210> SEQ ID NO 29
<211> LENGTH: 20
<212> TYPE: DNA
<213> ORGANISM: homo sapiens

<400> SEQUENCE: 29
cactacgacc caggcttcat                                              20

<210> SEQ ID NO 30
<211> LENGTH: 20
<212> TYPE: DNA
<213> ORGANISM: homo sapiens

<400> SEQUENCE: 30
ctccgcagct tcttgcttag                                              20
```

```
<210> SEQ ID NO 31
<211> LENGTH: 20
<212> TYPE: DNA
<213> ORGANISM: homo sapiens

<400> SEQUENCE: 31
atccttcttc atctggctgc                                          20

<210> SEQ ID NO 32
<211> LENGTH: 20
<212> TYPE: DNA
<213> ORGANISM: homo sapiens

<400> SEQUENCE: 32
aattggtgtc ctgaggatcg                                          20

<210> SEQ ID NO 33
<211> LENGTH: 20
<212> TYPE: DNA
<213> ORGANISM: homo sapiens

<400> SEQUENCE: 33
atagtgagcc cttcccacct                                          20

<210> SEQ ID NO 34
<211> LENGTH: 20
<212> TYPE: DNA
<213> ORGANISM: homo sapiens

<400> SEQUENCE: 34
aatgaacaga cccgcatttc                                          20

<210> SEQ ID NO 35
<211> LENGTH: 21
<212> TYPE: DNA
<213> ORGANISM: homo sapiens

<400> SEQUENCE: 35
gatcgccact ccagctacat c                                        21

<210> SEQ ID NO 36
<211> LENGTH: 16
<212> TYPE: DNA
<213> ORGANISM: homo sapiens

<400> SEQUENCE: 36
gggcacggca atgacc                                              16

<210> SEQ ID NO 37
<211> LENGTH: 2932
<212> TYPE: DNA
<213> ORGANISM: homo sapiens

<400> SEQUENCE: 37
gctccgcgcc gagggctgga ggatgcgttc cctggggtcc ggacttatga aaatatgcat    60
cagtttaata ctgtcttgga attcatgaga tggaagcata ggtcaaagct gtttggagaa   120
aatcagaagt acagttttat ctagccacat cttggaggag tcgtaagaaa gcagtgggag   180
ttgaagtcat tgtcaagtgc ttgcgatctt ttacaagaaa atctcactga atgatagtca   240
tttaaattgg tgaagtagca agaccaatta ttaaaggtga cagtacacag gaaacattac   300
aattgaacaa tgactcagct atacatttac atcagattat tgggagccta tttgttcatc   360
```

```
atttctcgtg ttcaaggaca gaatctggat agtatgcttc atggcactgg gatgaaatca      420
gactccgacc agaaaaagtc agaaaatgga gtaaccttag caccagagga taccttgcct      480
tttttaaagt gctattgctc agggcactgt ccagatgatg ctattaataa cacatgcata      540
actaatggac attgctttgc catcatagaa gaagatgacc agggagaaac cacattagct      600
tcagggtgta tgaaatatga aggatctgat tttcagtgca aagattctcc aaaagcccag      660
ctacgccgga caatagaatg ttgtcggacc aatttatgta accagtattt gcaacccaca      720
ctgccccctg ttgtcatagg tccgtttttt gatggcagca ttcgatggct ggttttgctc      780
atttctatgg ctgtctgcat aattgctatg atcatcttct ccagctgctt tgttacaaa       840 cattattgca agagcatctc aagcagacgt cgttacaatc gtgatttgga acaggatgaa      900
gcatttattc cagttggaga atcactaaaa gaccttattg accagtcaca aagttctggt      960
agtgggtctg gactaccttt attggttcag cgaactattg ccaaacagat tcagatggtc     1020
cggcaagttg gtaaaggccg atatggagaa gtatggatgg gcaaatggcg tggcgaaaaa     1080
gtggcggtga agtattcttt taccactgaa gaagccagct ggtttcgaga aacagaaatc     1140
taccaaactg tgctaatgcg ccatgaaaac atacttggtt tcatagcggc agacattaaa     1200
ggtacaggtt cctggactca gctctatttg attactgatt accatgaaaa tggatctctc     1260
tatgacttcc tgaaatgtgc tacactggac accagagccc tgcttaaatt ggcttattca     1320
gctgcctgtg gtctgtgcca cctgcacaca gaaatttatg cacccaagg aaagcccgca      1380 attgctcatc gagacctaaa gagcaaaaac atcctcatca agaaaatgg gagttgctgc      1440 attgctgacc tgggccttgc tgttaaattc aacagtgaca caaatgaagt tgatgtgccc     1500
ttgaatacca gggtgggcac caaacgctac atggctcccg aagtgctgga cgaaagcctg     1560
aacaaaaacc acttccagcc ctacatcatg gctgacatct acagcttcgg cctaatcatt     1620
tgggagatgg ctcgtcgttg tatcacagga gggatcgtgg aagaatacca attgccatat     1680
tacaacatgg taccgagtga tccgtcatac gaagatatgc gtgaggttgt gtgtgtcaaa     1740
cgtttgcggc caattgtgtc taatcggtgg aacagtgatg aatgtctacg agcagttttg     1800
aagctaatgt cagaatgctg ggcccacaat ccagcctcca gactcacagc attgagaatt     1860
aagaagacgc ttgccaagat ggttgaatcc aagatgtaa aaatctgatg gttaaaccat      1920
cggaggagaa actctagact gcaagaactg ttttacccca tggcatgggt ggaattagag     1980
tggaataagg atgttaactt ggttctcaga ctctttcttc actacgtgtt cacaggctgc     2040
taatattaaa cctttcagta ctcttattag gatacaagct gggaacttct aaacacttca     2100
ttctttatat atgacagct ttatttttaaa tgtggttttt gatgcctttt tttaagtggg      2160
tttttatgaa ctgcatcaag acttcaatcc tgattagtgt ctccagtcaa gctctgggta     2220
ctgaattgcc tgttcataaa acggtgcttt ctgtgaaagc cttaagaaga taatgagcg      2280 cagcagagat ggagaaatag actttgcctt ttacctgaga cattcagttc gtttgtattc     2340
tacctttgta aaacagccta tagatgatga tgtgtttggg atactgctta ttttatgata     2400
gtttgtcctg tgtccttagt gatgtgtgtg tgtctccatg cacatgcacg ccgggattcc     2460
tctgctgcca tttgaattag aagaaaataa tttatatgca tgcacaggaa gatattggtg     2520
gccggtggtt ttgtgcttta aaaatgcaat atctgaccaa gattcgccaa tctcatacaa     2580
gccatttact ttgcaagtga gatagcttcc ccaccagctt tatttttaa catgaaagct      2640 gatgccaagg ccaaaagaag tttaaagcat ctgtaaattt ggactgtttt ccttcaacca     2700
```

```
ccattttttt tgtggttatt attttttgtca cggaaagcat cctctccaaa gttggagctt    2760
ctattgccat gaaccatgct acaaagaaa gcacttctta ttgaagtgaa ttcctgcatt      2820
tgatagcaat gtaagtgcct ataaccatgt tctatattct ttattctcag taacttttaa    2880
aagggaagtt atttatattt tgtgtataat gtgctttatt tgcaaatcac cc             2932
```

<210> SEQ ID NO 38
<211> LENGTH: 532
<212> TYPE: PRT
<213> ORGANISM: homo sapiens

<400> SEQUENCE: 38

```
Met Thr Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
                20                  25                  30

Thr Gly Met Lys Ser Asp Ser Asp Gln Lys Lys Ser Glu Asn Gly Val
            35                  40                  45

Thr Leu Ala Pro Glu Asp Thr Leu Pro Phe Leu Lys Cys Tyr Cys Ser
        50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Ala Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                165                 170                 175

Lys His Tyr Cys Lys Ser Ile Ser Ser Arg Arg Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335
```

-continued

```
Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
    530

<210> SEQ ID NO 39
<211> LENGTH: 2032
<212> TYPE: DNA
<213> ORGANISM: homo sapiens

<400> SEQUENCE: 39
cgcggggcgc ggagtcggcg gggcctcgcg ggacgcgggc agtgcggaga ccgcggcgct      60
gaggacgcgg gagccgggag cgcacgcgcg gggtggagtt cagcctactc tttcttagat     120
gtgaaaggaa aggaagatca tttcatgcct tgttgataaa ggttcagact tctgctgatt     180
cataaccatt tggctctgag ctatgacaag agaggaaaca aaagttaaa cttacaagcc      240 tgccataagt gagaagcaaa cttccttgat aacatgcttt tgcgaagtgc aggaaaatta     300
aatgtgggca ccaagaaaga ggatggtgag agtacagccc ccaccccccg tccaaaggtc     360
ttgcgttgta atgccacca ccattgtcca gaagactcag tcaacaatat ttgcagcaca      420
gacggatatt gtttcacgat gatagaagag gatgactctg ggttgcctgt ggtcacttct     480
ggttgcctag gactagaagg ctcagatttt cagtgtcggg acactcccat tcctcatcaa     540
agaagatcaa ttgaatgctg cacagaaagg aacgaatgta ataaagacct acaccctaca     600
ctgcctccat tgaaaacag agattttgtt gatggaccta caccacag ggctttactt       660 atatctgtga ctgtctgtag tttgctcttg gtccttatca tattattttg ttacttccgg     720
tataaaagac aagaaaccag acctcgatac agcattgggt tagaacagga tgaaacttac     780
attcctcctg gagaatccct gagagactta attgagcagt ctcagagctc aggaagtgga     840
tcaggcctcc ctctgctggt ccaaaggact atagctaagc agattcagat ggtgaaacag     900
attggaaaag gtcgctatgg ggaagtttgg atgggaaagt ggcgtggcga aaaggtagct     960
```

```
gtgaaagtgt tcttcaccac agaggaagcc agctggttca gagagacaga aatatatcag    1020
acagtgttga tgaggcatga aaacattttg ggtttcattg ctgcagatat caaagggaca    1080
gggtcctgga cccagttgta cctaatcaca gactatcatg aaaatggttc cctttatgat    1140
tatctgaagt ccaccaccct agacgctaaa tcaatgctga agttagccta ctcttctgtc    1200
agtggcttat gtcatttaca cacagaaatc tttagtactc aaggcaaacc agcaattgcc    1260
catcgagatc tgaaaagtaa aaacattctg gtgaagaaaa atggaacttg ctgtattgct    1320
gacctgggcc tggctgttaa atttattagt gatacaaatg aagttgacat accacctaac    1380
actcgagttg gcaccaaacg ctatatgcct ccagaagtgt tggacgagag cttgaacaga    1440
aatcacttcc agtcttacat catggctgac atgtatagtt ttggcctcat cctttgggag    1500
gttgctagga gatgtgtatc aggaggtata gtggaagaat accagcttcc ttatcatgac    1560
ctagtgccca gtgacccctc ttatgaggac atgagggaga ttgtgtgcat caagaagtta    1620
cgcccctcat tcccaaaccg gtggagcagt gatgagtgtc taaggcagat gggaaaactc    1680
atgacagaat gctgggctca caatcctgca tcaaggctga cagccctgcg ggttaagaaa    1740
acacttgcca aaatgtcaga gtcccaggac attaaactct gataggagag aaaagtaag    1800 catctctgca gaaagccaac aggtactctt ctgtttgtgg gcagagcaaa agacatcaaa    1860
taagcatcca cagtacaagc cttgaacatc gtcctgcttc ccagtgggtt cagacctcac    1920
ctttcaggga gcgacctggg caaagacaga gaagctccca gaaggagaga ttgatccgtg    1980 tctgttttgta ggcggagaaa ccgttgggta acttgttcaa gatatgatgc at          2032
```

<210> SEQ ID NO 40
<211> LENGTH: 502
<212> TYPE: PRT
<213> ORGANISM: homo sapiens

<400> SEQUENCE: 40

```
Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190
```

Pro Leu Leu Val Gln Arg Thr Ile Ala Lys Gln Ile Gln Met Val Lys
            195                 200                 205

Gln Ile Gly Lys Gly Arg Tyr Gly Glu Val Trp Met Gly Lys Trp Arg
        210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Lys
        435                 440                 445

Leu Arg Pro Ser Phe Pro Asn Arg Trp Ser Ser Asp Glu Cys Leu Arg
450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500

<210> SEQ ID NO 41
<211> LENGTH: 3611
<212> TYPE: DNA
<213> ORGANISM: homo sapiens

<400> SEQUENCE: 41
cgccccccga ccccggatcg aatccccgcc ctccgcaccc tggatatgtt ttctcccaga     60
cctggatatt tttttgatat cgtgaaacta cgagggaaat aatttggggg atttcttctt    120
ggctccctgc tttccccaca gacatgcctt ccgtttggag ggccgcggca ccccgtccga    180
ggcgaaggaa ccccccagc cgcgagggag agaaatgaag ggaatttctg cagcggcatg    240
aaagctctgc agctaggtcc tctcatcagc catttgtcct ttcaaactgt attgtgatac    300

```
gggcaggatc agtccacggg agagaagacg agcctcccgg ctgtttctcc gccggtctac    360
ttcccatatt tcttttcttt gccctcctga ttcttggctg gcccagggat gacttcctcg    420
ctgcagcggc cctggcgggt gccctggcta ccatgaccat cctgctggt cagcactgcg    480 gctgcttcgc agaatcaaga acggctatgt gcgtttaaag atccgtatca gcaagacctt    540
gggataggtg agagtagaat ctctcatgaa aatgggacaa tattatgctc gaaaggtagc    600
acctgctatg gcctttggga gaaatcaaaa ggggacataa atcttgtaaa acaaggatgt    660
tggtctcaca ttggagatcc ccaagagtgt cactatgaag aatgtgtagt aactaccact    720
cctccctcaa ttcagaatgg aacataccgt ttctgctgtt gtagcacaga tttatgtaat    780
gtcaacttta ctgagaattt tccacctcct gacacaacac cactcagtcc acctcattca    840
tttaaccgag atgagacaat aatcattgct ttggcatcag tctctgtatt agctgttttg    900
atagttgcct tatgctttgg atacagaatg ttgacaggag accgtaaaca aggtcttcac    960
agtatgaaca tgatggaggc agcagcatcc gaaccctctc ttgatctaga taatctgaaa    1020
ctgttggagc tgattggccg aggtcgatat ggagcagtat ataaaggctc cttggatgag    1080
cgtccagttg ctgtaaaagt gttttccttt gcaaaccgtc agaattttat caacgaaaag    1140
aacatttaca gagtgccttt gatggaacat gacaacattg cccgctttat agttggagat    1200
gagagagtca ctgcagatgg acgcatggaa tatttgcttg tgatggagta ctatcccaat    1260
ggatctttat gcaagtattt aagtctccac acaagtgact gggtaagctc ttgccgtctt    1320
gctcattctg ttactagagg actggcttat cttcacacag aattaccacg aggagatcat    1380
tataaacctg caatttccca tcgagattta aacagcagaa atgtcctagt gaaaaatgat    1440
ggaacctgtg ttattagtga cttttggact tccatgagcc tgactggaaa tagactggtg    1500
cgcccagggg aggaagataa tgcagccata agcgaggttg gcactatcag atatatggca    1560
ccagaagtgc tagaaggagc tgtgaacttg agggactgtg aatcagcttt gaaacaagta    1620
gacatgtatg ctcttggact aatctattgg gagatattta tgagatgtac agacctcttc    1680
ccaggggaat ccgtaccaga gtaccagatg gcttttcaga cagaggttgg aaaccatccc    1740
acttttgagg atatgcaggt tctcgtgtct agggaaaaac agagacccaa gttcccagaa    1800
gcctggaaag aaaatagcct ggcagtgagg tcactcaagg agacaatcga agactgttgg    1860
gaccaggatg cagaggctcg gcttactgca cagtgtgctg aggaaggat ggctgaactt    1920 atgatgattt gggaaagaaa caaatctgtg agcccaacag tcaatccaat gtctactgct    1980
atgcagaatg aacgcaacct gtcacataat aggcgtgtgc caaaaattgg tccttatcca    2040
gattattctt cctcctcata cattgaagac tctatccatc atactgacag catcgtgaag    2100
aatatttcct ctgagcattc tatgtccagc acacctttga ctataggga aaaaaaccga    2160 aattcaatta actatgaacg acagcaagca caagctcgaa tccccagccc tgaaacaagt    2220
gtcaccagcc tctccaccaa cacaacaacc acaaacacca caggactcac gccaagtact    2280
ggcatgacta ctatatctga gatgccatac ccagatgaaa caaatctgca taccacaaat    2340
gttgcacagt caattgggcc aacccctgtc tgcttacagc tgacagaaga agacttggaa    2400
accaacaagc tagacccaaa agaagttgat aagaacctca ggaaagctc tgatgagaat    2460 ctcatggagc actctcttaa acagttcagt ggcccagacc cactgagcag tactagttct    2520
agcttgcttt acccactcat aaaacttgca gtagaagcaa ctggacagca ggacttcaca    2580
cagactgcaa atggccaagc atgtttgatt cctgatgttc tgcctactca gatctatcct    2640
ctccccaagc agcagaacct tcccaagaga cctactagtt tgccttttgaa caccaaaaat    2700
```

-continued

```
tcaacaaaag agccccggct aaaatttggc agcaagcaca aatcaaactt gaaacaagtc    2760
gaaactggag ttgccaagat gaatacaatc aatgcagcag aacctcatgt ggtgacagtc    2820
accatgaatg tgtgtggcagg tagaaaccac agtgttaact cccatgctgc cacaaccccaa   2880 tatgccaatg ggacagtact atctggccaa acaaccaaca tagtgacaca tagggcccaa    2940
gaaatgttgc agaatcagtt tattggtgag acacccggc tgaatattaa ttccagtcct    3000
gatgagcatg agcctttact gagacgagag caacaagctg ccatgatga aggtgttctg    3060 gatcgtcttg tggacaggag ggaacggcca ctagaaggtg gccgaactaa ttccaataac    3120
aacaacagca atccatgttc agaacaagat gttcttgcac agggtgttcc aagcacagca    3180
gcagatcctg ggccatcaaa gcccagaaga gcacagaggc ctaattctct ggatctttca    3240
gccacaaatg tcctggatgg cagcagtata cagataggtg agtcaacaca agatggcaaa    3300
tcaggatcag gtgaaaagat caagaaacgt gtgaaaactc cctattctct taagcggtgg    3360
cgcccctcca cctgggtcat ctccactgaa tcgctggact gtgaagtcaa caataatggc    3420
agtaacaggg cagttcattc caaatccagc actgctgttt accttgcaga aggaggcact    3480
gctacaacca tggtgtctaa agatatagga atgaactgtc tgtgaaatgt tttcaagcct    3540
atggagtgaa attatttttt gcatcattta acatgcaga agatgtttaa aaataaaaaa     3600
aaaactgctt t                                                          3611
```

<210> SEQ ID NO 42
<211> LENGTH: 1038
<212> TYPE: PRT
<213> ORGANISM: homo sapiens

<400> SEQUENCE: 42

```
Met Thr Ser Ser Leu Gln Arg Pro Trp Arg Val Pro Trp Leu Pro Trp
1               5                   10                  15

Thr Ile Leu Leu Val Ser Thr Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Asp Thr Thr Pro Leu Ser Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205
```

Ile Gly Arg Gly Arg Tyr Gly Ala Val Tyr Lys Gly Ser Leu Asp Glu
210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
            245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
            275                 280                 285

Lys Tyr Leu Ser Leu His Thr Ser Asp Trp Val Ser Ser Cys Arg Leu
            290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
            325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
            355                 360                 365

Glu Asp Asn Ala Ala Ile Ser Glu Val Gly Thr Ile Arg Tyr Met Ala
            370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
            405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
            435                 440                 445

Met Gln Val Leu Val Ser Arg Glu Lys Gln Arg Pro Lys Phe Pro Glu
450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
            485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
            515                 520                 525

Arg Asn Leu Ser His Asn Arg Arg Val Pro Lys Ile Gly Pro Tyr Pro
            530                 535                 540

Asp Tyr Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
            565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
            595                 600                 605

Ser Thr Asn Thr Thr Thr Thr Asn Thr Thr Gly Leu Thr Pro Ser Thr
            610                 615                 620

-continued

```
Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
            645                 650                 655

Gln Leu Thr Glu Glu Asp Leu Glu Thr Asn Lys Leu Asp Pro Lys Glu
        660                 665                 670

Val Asp Lys Asn Leu Lys Glu Ser Ser Asp Glu Asn Leu Met Glu His
    675                 680                 685

Ser Leu Lys Gln Phe Ser Gly Pro Asp Pro Leu Ser Ser Thr Ser Ser
690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
            820                 825                 830

Gly Gln Thr Thr Asn Ile Val Thr His Arg Ala Gln Glu Met Leu Gln
        835                 840                 845

Asn Gln Phe Ile Gly Glu Asp Thr Arg Leu Asn Ile Asn Ser Ser Pro
    850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Ser Asn Pro Cys Ser Glu
            900                 905                 910

Gln Asp Val Leu Ala Gln Gly Val Pro Ser Thr Ala Ala Asp Pro Gly
        915                 920                 925

Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Asn Gly Ser Asn Arg Ala
        995                 1000                1005

Val His Ser Lys Ser Ser Thr Ala Val Tyr Leu Ala Glu Gly Gly
    1010                1015                1020

Thr Ala Thr Thr Met Val Ser Lys Asp Ile Gly Met Asn Cys Leu
    1025                1030                1035
```

<210> SEQ ID NO 43
<211> LENGTH: 3561
<212> TYPE: DNA
<213> ORGANISM: homo sapiens

<400> SEQUENCE: 43

| | | | | | |
|---|---|---|---|---|---|
| cccgggtcag | cgcccgcccg | cccgcgctcc | tcccggccgc | tcctcccgcc | ccgcccggcc | 60 |
| cggcgccgac | tctgcggccg | cccgacgagc | ccctcgcggc | actgcccggg | ccccggcccc | 120 |
| ggccccggcc | ccctcccgcc | gcaccgcccc | cggcccggcc | ctccgccctc | cgcactcccg | 180 |
| cctccctccc | tccgcccgct | cccgcgccct | cctccctccc | tcctcccag | ctgtcccgtt | 240 |
| cgcgtcatgc | cgagcctccc | ggccccgccg | gccccgctgc | tgctcctcgg | gctgctgctg | 300 |
| ctcggctccc | ggccggcccg | cggcgccggc | cccgagcccc | ccgtgctgcc | catccgttct | 360 |
| gagaaggagc | cgctgcccgt | tcggggagcg | gcaggctgca | ccttcggcgg | aaggtctat | 420 |
| gccttggacg | agacgtggca | cccggaccta | ggggagccat | tcggggtgat | gcgctgcgtg | 480 |
| ctgtgcgcct | gcgaggcgac | agggaccttg | aggcccagag | agatgaagta | gcttgtctag | 540 |
| ggtcacgcag | cttcctcagt | ggggtcgccg | taccagggc | cctggcaggg | tcagctgcaa | 600 |
| gaacatcaaa | ccagagtgcc | caaccccggc | ctgtgggcag | ccgcgccagc | tgccgggaca | 660 |
| ctgctgccag | acctgccccc | aggagcgcag | cagttcggag | cggcagccga | gcggcctgtc | 720 |
| cttcgagtat | ccgcgggacc | cggagcatcg | cagttatagc | gaccgcgggg | agccaggcgc | 780 |
| tgaggagcgg | gcccgtggtg | acggccacac | ggacttcgtg | gcgctgctga | cagggccgag | 840 |
| gtcgcaggcg | gtggcacgag | cccgagtctc | gctgctgcgc | tctagcctcc | gcttctctat | 900 |
| ctcctacagg | cggctggacc | gccctaccag | gatccgcttc | tcagactcca | atggcagtgt | 960 |
| cctgtttgag | cacctgcag | cccccaccca | agatggcctg | gtctgtgggg | tgtggcgggc | 1020 |
| agtgcctcgg | ttgtctctgc | ggctccttag | ggcagaacag | ctgcatgtgg | cacttgtgac | 1080 |
| actcactcac | ccttcagggg | aggtctgggg | gcctctcatc | cggcaccggg | ccctggctgc | 1140 |
| agagaccttc | agtgccatcc | tgactctaga | aggcccccca | cagcagggcg | taggggcat | 1200 |
| caccctgctc | actctcagtg | acacagagga | ctccttgcat | tttttgctgc | tcttccgagg | 1260 |
| gctgctggaa | cccaggagtg | gggattctac | accaggggca | gctactgcga | gaacttcagg | 1320 |
| ccaatgtctc | agcccaggaa | ccaggctttg | ctgaggtgct | gcccaacctg | acagtccagg | 1380 |
| agatggactg | gctggtgctg | ggggagctgc | agatggccct | ggagtgggca | ggcaggccag | 1440 |
| ggctgcgcat | cagtggacac | attgctgcca | ggaagagctg | cgacgtcctg | caaagtgtcc | 1500 |
| tttgtggggc | tgatgccctg | atcccagtcc | agacgggtgc | tgccggctca | gccagcctca | 1560 |
| cgctgctagg | aaatggctcc | ctgatctatc | aggtgcaagt | ggtagggaca | agcagtgagg | 1620 |
| tggtggccat | gacactggag | accaagcctc | agcggaggga | tcagcgcact | gtcctgtgcc | 1680 |
| acatggctgg | actccagcca | ggaggacaca | cggccgtggg | tatctgccct | gggctgggtg | 1740 |
| cccgagggc | tcatatgctg | ctgcagaatg | agctcttcct | gaacgtgggc | accaaggact | 1800 |
| tcccagacgg | agagcttcgg | gggcacgtgg | ctgccctgcc | ctactgtggg | catagctccc | 1860 |
| gccatgacac | gctgcccgtg | ccctagcag | gagccctggt | gctaccccct | gtgaagagcc | 1920 |
| aagcagcagg | gcacgcctgg | cttcccttgg | atacccactg | tcacctgcac | tatgaagtgc | 1980 |
| tgctggctgg | gcttggtggc | tcagaacaag | gcactgtcac | tgcccacctc | cttgggcctc | 2040 |
| ctggaacgcc | agggcctcgg | cggctgctga | agggattcta | tggctcagag | gcccaggtg | 2100 |
| tggtgaagga | cctggagccg | gaactgctgc | ggcacctggc | aaaaggcatg | gcctccctga | 2160 |

```
tgatcaccac caagggtagc cccagagggg agctccgagg gcaggtgcac atagccaacc    2220
aatgtgaggt tggcggactg cgcctggagg cggccggggc cgagggggtg cgggcgctgg    2280
gggctccgga tacagcctct gctgcgccgc ctgtggtgcc tggtctcccg gccctagcgc    2340
ccgccaaacc tggtggtcct gggcggcccc gagaccccaa cacatgcttc ttcgaggggc    2400
agcagcgccc ccacggggct cgctgggcgc ccaactacga cccgctctgc tcactctgca    2460
cctgccagag acgaacggtg atctgtgacc cggtggtgtg cccaccgccc agctgcccac    2520
acccggtgca ggctcccgac cagtgctgcc ctgtttgccc tgagaaacaa gatgtcagag    2580
acttgccagg gctgccaagg agccgggacc caggagaggg ctgctatttt gatggtgacc    2640
ggagctggcg ggcagcgggt acgcggtggc accccgttgt gccccccttt ggcttaatta    2700
agtgtgctgt ctgcacctgc aagggggggca ctggagaggg gcactgtgag aaggtgcagt    2760
gtccccggct ggcctgtgcc cagcctgtgc gtgtcaaccc caccgactgc tgcaaacagt    2820
gtccagtggg gtcgggggcc cacccccagc tgggggaccc catgcaggct gatgggcccc    2880
ggggctgccg ttttgctggg cagtggttcc cagagagtca gagctggcac ccctcagtgc    2940
cccctttttgg agagatgagc tgtatcacct gcagatgtgg ggcaggggtg cctcactgtg    3000
agcgggatga ctgttcactg ccactgtcct gtggctcggg gaaggagagt cgatgctgtt    3060
cccgctgcac ggcccaccgg cggccagccc cagagaccag aactgatcca gagctggaga    3120
aagaagccga aggctcttag ggagcagcca gagggccaag tgaccaagag gatggggcct    3180
gagctgggga aggggtggca tcgaggacct tcttgcattc tcctgtggga agcccagtgc    3240
ctttgctccc ctgtcctgcc tctactccca cccccactac ctctgggaac cacagctcca    3300
caaggggggag aggcagctgg gccagaccga ggtcacagcc actccaagtc ctgccctgcc    3360
accctcggcc tctgtcctgg aagccccacc cctttcctcc tgtacataat gtcactggct    3420
tgttgggatt tttaatttat cttcactcag caccaagggc cccgacacct ccactcctgc    3480
tgcccctgag ctgagcagag tcattattgg agagttttgt atttattaaa acatttcttt    3540
ttcagtcaaa aaaaaaaaa a                                                3561
```

<210> SEQ ID NO 44
<211> LENGTH: 94
<212> TYPE: PRT
<213> ORGANISM: homo sapiens

<400> SEQUENCE: 44

```
Met Pro Ser Leu Pro Ala Pro Pro Ala Pro Leu Leu Leu Gly Leu
1               5                   10                  15

Leu Leu Leu Gly Ser Arg Pro Ala Arg Gly Ala Gly Pro Glu Pro Pro
                20                  25                  30

Val Leu Pro Ile Arg Ser Glu Lys Glu Pro Leu Pro Val Arg Gly Ala
            35                  40                  45

Ala Gly Cys Thr Phe Gly Gly Lys Val Tyr Ala Leu Asp Glu Thr Trp
        50                  55                  60

His Pro Asp Leu Gly Glu Pro Phe Gly Val Met Arg Cys Val Leu Cys
65                  70                  75                  80

Ala Cys Glu Ala Thr Gly Thr Leu Arg Pro Arg Glu Met Lys
                85                  90
```

<210> SEQ ID NO 45
<211> LENGTH: 4049
<212> TYPE: DNA
<213> ORGANISM: homo sapiens

<400> SEQUENCE: 45

```
gcggccgcac tcagcgccac gcgtcgaaag cgcaggcccc gaggacccgc cgcactgaca        60
gtatgagccg cacagcctac acggtgggag ccctgcttct cctcttgggg accctgctgc       120
cggctgctga agggaaaaag aaagggtccc aaggtgccat ccccccgcca gacaaggccc       180
agcacaatga ctcagagcag actcagtcgc cccagcagcc tggctccagg aaccgggggc       240
ggggccaagg gcgggcact gccatgcccg ggaggaggt gctggagtcc agccaagagg         300
ccctgcatgt gacggagcgc aaatacctga agcgagactg gtgcaaaacc cagccgctta       360
agcagaccat ccacgaggaa ggctgcaaca gtcgcaccat catcaaccgc ttctgttacg       420
gccagtgcaa ctcttctac atccccaggc acatccggaa ggaggaaggt tcctttcagt        480
cctgctcctt ctgcaagccc aagaaattca ctaccatgat ggtcacactc aactgccctg       540
aactacagcc acctaccaag aagaagagag tcacacgtgt gaagcagtgt cgttgcatat       600
ccatcgattt ggattaagcc aaatccaggt gcacccagca tgtcctagga atgcagcccc       660
aggaagtccc agacctaaaa caaccagatt cttacttggc ttaaacctag aggccagaag       720
aaccccagc tgcctcctgg caggagcctg cttgtgcgta gttcgtgtgc atgagtgtgg        780
atgggtgcct gtgggtgttt ttagacacca gagaaaacac agtctctgct agagagcact       840
ccctattttg taaacatatc tgctttaatg gggatgtacc agaaacccac ctcacccggg       900
ctcacatcta aggggcggg ccgtggtct ggttctgact tgtgttttt gtgcctcct            960
ggggaccaga atctcctttc ggaatgaatg ttcatggaag aggctcctct gagggcaaga      1020
gacctgtttt agtgctgcat tcgacatgga aaagtccttt taacctgtgc ttgcatcctc      1080
ctttcctcct cctcctcaca atccatctct tcttaagttg atagtgacta tgtcagtcta      1140
atctcttgtt tgccaaggtt cctaaattaa ttcacttaac catgatgcaa atgtttttca      1200
ttttgtgaag accctccaga ctctgggaga ggctggtgtg ggcaaggaca agcaggatag      1260
tggagtgaga aagggagggt ggagggtgag gccaaatcag gtccagcaaa agtcagtagg      1320
gacattgcag aagcttgaaa ggccaatacc agaacacagg ctgatgcttc tgagaaagtc      1380
ttttcctagt atttaacaga acccaagtga acagaggaga aatgagattg ccagaaagtg      1440
attaactttg gccgttgcaa tctgctcaaa cctaacacca aactgaaaac ataaatactg      1500
accactccta tgttcggacc caagcaagtt agctaaacca aaccaactcc tctgctttgt      1560
ccctcaggtg gaaagagag gtagtttaga actctctgca taggggtggg aattaatcaa       1620
aaacckcaga ggctgaaatt cctaataccT ttcctttatc gtggttatag tcagctcatt      1680
tccattccac tatttcccat aatgcttctg agagccacta acttgattga taaagatcct      1740
gcctctgctg agtgtacctg acagtaagtc taaagatgar agagtttagg gactactctg      1800
ttttagcaag aratattktg ggggtctttt tgttttaact attgtcagga gattgggcta      1860
ragagaagac gacgagagta aggaaataaa gggrattgcc tctggctaga gagtaagtta      1920
ggtgttaata cctggtagaa atgtaaggga tatgacctcc ctttctttat gtgctcactg      1980
aggatctgag gggaccctgt taggagagca tagcatcatg atgtattagc tgttcatctg      2040
ctactggttg gatggacata actattgtaa ctattcagta tttactggta ggcactgtcc      2100
tctgattaaa cttggcctac tggcaatggc tacttaggat tgatctaagg gccaaagtgc      2160
agggtgggtg aactttattg tactttggat ttggttaacc tgttttcttc aagcctgagg      2220
ttttatatac aaactccctg aatactcttt ttgccttgta tcttctcagc ctcctagcca      2280
```

```
agtcctatgt aatatggaaa acaaacactg cagacttgag attcagttgc cgatcaaggc    2340
tctggcattc agagaaccct tgcaactcga gaagctgttt ttatttcgtt tttgttttga    2400
tccagtgctc tcccatctaa caactaaaca ggagccattt caaggcggga gatattttaa    2460
acacccaaaa tgttgggtct gatttttcaaa cttttaaact cactactgat gattctcacg    2520
ctaggcgaat ttgtccaaac acatagtgtg tgtgttttgt atacactgta tgaccccacc    2580
ccaaatcttt gtattgtcca cattctccaa caataaagca cagagtggat ttaattaagc    2640
acacaaatgc taaggcagaa ttttgagggt gggagagaag aaaagggaaa gaagctgaaa    2700
atgtaaaacc acaccaggga ggaaaaatga cattcagaac cagcaaacac tgaatttctc    2760
ttgttgtttt aactctgcca caagaatgca atttcgttaa tggagatgac ttaagttggc    2820
agcagtaatc ttctttagg agcttgtacc acagtcttgc acataagtgc agatttggct    2880
caagtaaaga gaatttcctc aacactaact tcactgggat aatcagcagc gtaactaccc    2940
taaaagcata tcactagcca aagagggaaa tatctgttct tcttactgtg cctatattaa    3000
gactagtaca aatgtggtgt gtcttccaac tttcattgaa aatgccatat ctataccata    3060
ttttattcga gtcactgatg atgtaatgat atattttttc attattatag tagaatattt    3120
ttatggcaag atatttgtgg tcttgatcat acctattaaa ataatgccaa acaccaaata    3180
tgaattttat gatgtacact ttgtgcttgg cattaaaaga aaaaaacaca catcctggaa    3240
gtctgtaagt tgttttttgt tactgtaggt cttcaaagtt aagagtgtaa gtgaaaaatc    3300
tggaggagag gataaatttcc actgtgtgga atgtgaatag ttaaatgaaa agttatggtt    3360
atttaatgta attattactt caaatccttt ggtcactgtg atttcaagca tgttttcttt    3420
ttctccttta tatgactttc tctgagttgg gcaaagaaga agctgacaca ccgtatgttg    3480
ttagagtctt ttatctggtc aggggaaaca aaatcttgac ccagctgaac atgtcttcct    3540
gagtcagtgc ctgaatcttt attttttaaa ttgaatgttc cttaaaggtt aacatttcta    3600
aagcaatatt aagaaagact ttaaatgtta ttttggaaga cttacgatgc atgtatacaa    3660
acgaatagca gataatgatg actagttcac acataaagtc cttttaagga gaaaatctaa    3720
aatgaaaagt ggataaacag aacatttata agtgatcagt taatgcctaa gagtgaaagt    3780
agttctattg acattcctca agatatttaa tatcaactgc attatgtatt atgtctgctt    3840
aaatcattta aaaacggcaa agaattatat agactatgag gtaccttgct gtgtaggagg    3900
atgaaagggg agttgatagt ctcataaaac taatttggct tcaagtttca tgaatctgta    3960
actagaattt aattttcacc ccaataatgt tctatatagc ctttgctaaa gagcaactaa    4020
taaattaaac ctattctttc aaaaaaaaa                                      4049
```

<210> SEQ ID NO 46
<211> LENGTH: 184
<212> TYPE: PRT
<213> ORGANISM: homo sapiens

<400> SEQUENCE: 46

Met Ser Arg Thr Ala Tyr Thr Val Gly Ala Leu Leu Leu Leu Gly
1               5                   10                  15

Thr Leu Leu Pro Ala Ala Glu Gly Lys Lys Lys Gly Ser Gln Gly Ala
                20                  25                  30

Ile Pro Pro Pro Asp Lys Ala Gln His Asn Asp Ser Glu Gln Thr Gln
            35                  40                  45

Ser Pro Gln Gln Pro Gly Ser Arg Asn Arg Gly Arg Gly Gln Gly Arg
        50                  55                  60

```
Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Gly Cys Asn Ser Arg Thr
            100                 105                 110

Ile Ile Asn Arg Phe Cys Tyr Gly Gln Cys Asn Ser Phe Tyr Ile Pro
            115                 120                 125

Arg His Ile Arg Lys Glu Glu Gly Ser Phe Gln Ser Cys Ser Phe Cys
            130                 135                 140

Lys Pro Lys Lys Phe Thr Thr Met Met Val Thr Leu Asn Cys Pro Glu
145                 150                 155                 160

Leu Gln Pro Pro Thr Lys Lys Lys Arg Val Thr Arg Val Lys Gln Cys
                165                 170                 175

Arg Cys Ile Ser Ile Asp Leu Asp
            180

<210> SEQ ID NO 47
<211> LENGTH: 1386
<212> TYPE: DNA
<213> ORGANISM: homo sapiens

<400> SEQUENCE: 47
gctcctcgcc  ccgcgcctgc  ccccaggatg  gtccgcgcga  ggcaccagcc  gggtgggctt       60
tgcctcctgc  tgctgctgct  ctgccagttc  atggaggacc  gcagtgccca  ggctgggaac     120
tgctggctcc  gtcaagcgaa  gaacggccgc  tgccaggtcc  tgtacaagac  cgaactgagc     180
aaggaggagt  gctgcagcac  cggccggctg  agcacctcgt  ggaccgagga  ggacgtgaat     240
gacaacacac  tcttcaagtg  gatgattttc  aacggggggcg  cccccaactg  catcccctgt     300
aaagaaacgt  gtgagaacgt  ggactgtgga  cctgggaaaa  aatgccgaat  gaacaagaag     360
aacaaacccc  gctgcgtctg  cgccccggat  tgttccaaca  tcacctggaa  gggtccagtc     420
tgcgggctgg  atgggaaaac  ctaccgcaat  gaatgtgcac  tcctaaaggc  aagatgtaaa     480
gagcagccag  aactggaagt  ccagtaccaa  ggcagatgta  aaaagacttg  tcgggatgtt     540
ttctgtccag  gcagctccac  atgtgtggtg  gaccagacca  ataatgccta  ctgtgtgacc     600
tgtaatcgga  tttgcccaga  gcctgcttcc  tctgagcaat  atctctgtgg  aatgatgga     660 gtcacctact  ccagtgcctg  ccacctgaga  aaggctacct  gcctgctggg  cagatctatt     720
ggattagcct  atgagggaaa  gtgtatcaaa  gcaaagtcct  gtgaagatat  ccagtgcact     780
ggtgggaaaa  aatgtttatg  ggatttcaag  gttgggagag  gccggtgttc  cctctgtgat     840
gagctgtgcc  ctgacagtaa  gtcggatgag  cctgtctgtg  ccagtgacaa  tgccacttat     900
gccagcgagt  gtgccatgaa  ggaagctgcc  tgctcctcag  gtgtgctact  ggaagtaaag     960
cactccggat  cttgcaactg  aatctgcccg  taaaacctga  gccattgatt  cttcagaact    1020
ttctgcagtt  tttgacttca  tagattatgc  tttaaaaaat  ttttttttaac  ttattgcata    1080 acagcagatg  ccaaaaacaa  aaaaagcatc  tcactgcaag  tcacataaaa  atgcaacgct    1140
gtaatatggc  tgtatcagag  ggctttgaaa  acatacactg  agctgcttct  gcgctgttgt    1200
tgtccgtatt  taaacaacag  ctcccctgta  ttccccccatc  tagccatttc  ggaagacacc    1260
gaggaagagg  aggaagatga  agaccaggac  tacagctttc  ctatatcttc  tattctagag    1320
tggtaaactc  tctataagtg  ttcagtgttc  acatagcctt  tgtgcaaaaa  aaaaaaaaaa    1380
``` aaaaaa 1386

<210> SEQ ID NO 48
<211> LENGTH: 317
<212> TYPE: PRT
<213> ORGANISM: homo sapiens

<400> SEQUENCE: 48

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn
305                 310                 315

<210> SEQ ID NO 49
<211> LENGTH: 699
<212> TYPE: DNA
<213> ORGANISM: homo sapiens

<400> SEQUENCE: 49
atggagcgct gccccagcct aggggtcacc ctctacgccc tggtggtggt cctggggctg     60

-continued

```
cgggcgacac cggccggcgg ccagcactat ctccacatcc gcccggcacc cagcgacaac      120
ctgcccctgg tggacctcat cgaacaccca gaccctatct ttgaccccaa ggaaaaggat      180
ctgaacgaga cgctgctgcg ctcgctgctc gggggccact acgacccagg cttcatggcc      240
acctcgcccc ccgaggaccg gcccggcggg ggcggggggtg cagctggggg cgcggaggac     300
ctggcggagc tggaccagct gctgcggcag cggccgtcgg gggccatgcc gagcgagatc      360
aaagggctag agttctccga gggcttggcc cagggcaaga agcagcgcct aagcaagaag      420
ctgcggagga agttacagat gtggctgtgg tcgcagacat tctgccccgt gctgtacgcg      480
tggaacgacc tgggcagccg cttttggccg cgctacgtga aggtgggcag ctgcttcagt      540
aagcgctcgt gctccgtgcc cgagggcatg gtgtgcaagc cgtccaagtc cgtgcacctc      600
acggtgctgc ggtggcgctg tcagcggcgc gggggccagc gctgcggctg gattcccatc      660
cagtacccca tcatttccga gtgcaagtgc tcgtgctag                             699
```

<210> SEQ ID NO 50
<211> LENGTH: 232
<212> TYPE: PRT
<213> ORGANISM: homo sapiens

<400> SEQUENCE: 50

```
Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
        115                 120                 125

Leu Ala Gln Gly Lys Lys Gln Arg Leu Ser Lys Leu Arg Arg Lys
    130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
        195                 200                 205

Arg Arg Gly Gly Gln Arg Cys Gly Trp Ile Pro Ile Gln Tyr Pro Ile
    210                 215                 220

Ile Ser Glu Cys Lys Cys Ser Cys
225                 230
```

<210> SEQ ID NO 51
<211> LENGTH: 804

<210> SEQ ID NO 51
<211> LENGTH: 804
<212> TYPE: DNA
<213> ORGANISM: homo sapiens

<400> SEQUENCE: 51

```
atgcatctcc tcttatttca gctgctggta ctcctgcctc taggaaagac cacacggcac    60
caggatggcc gccagaatca gagttctctt tcccccgtac tcctgccaag gaatcaaaga   120
gagcttccca caggcaacca tgaggaagct gaggagaagc cagatctgtt tgtcgcagtg   180
ccacaccttg tagccaccag ccctgcaggg aaggccaga ggcagagaga aagatgctg     240
tccagatttg gcaggttctg gaagaagcct gagagagaaa tgcatccatc cagggactca   300
gatagtgagc ccttcccacc tgggacccag tccctcatcc agccgataga tggaatgaaa   360
atggagaaat ctcctcttcg ggaagaagcc aagaaattct ggcaccactt catgttcaga   420
aaaactccgg cttctcaggg ggtcatcttg cccatcaaaa gccatgaagt acattgggag   480
acctgcagga cagtgccctt cagccagact ataacccacg aaggctgtga aaaagtagtt   540
gttcagaaca acctttgctt tgggaaatgc gggtctgttc attttcctgg agccgcgcag   600
cactcccata cctcctgctc tcactgtttg cctgccaagt tcaccacgat gcacttgcca   660
ctgaactgca ctgaactttc ctccgtgatc aaggtggtga tgctggtgga ggagtgccag   720
tgcaaggtga agacggagca tgaagatgga cacatcctac atgctggctc ccaggattcc   780
tttatcccag gagtttcagc ttga                                          804
```

<210> SEQ ID NO 52
<211> LENGTH: 267
<212> TYPE: PRT
<213> ORGANISM: homo sapiens

<400> SEQUENCE: 52

```
Met His Leu Leu Leu Phe Gln Leu Leu Val Leu Leu Pro Leu Gly Lys
1               5                   10                  15

Thr Thr Arg His Gln Asp Gly Arg Gln Asn Gln Ser Ser Leu Ser Pro
            20                  25                  30

Val Leu Leu Pro Arg Asn Gln Arg Glu Leu Pro Thr Gly Asn His Glu
        35                  40                  45

Glu Ala Glu Glu Lys Pro Asp Leu Phe Val Ala Val Pro His Leu Val
    50                  55                  60

Ala Thr Ser Pro Ala Gly Gly Gln Arg Gln Arg Glu Lys Met Leu
65                  70                  75                  80

Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
            100                 105                 110

Ile Gln Pro Ile Asp Gly Met Lys Met Glu Lys Ser Pro Leu Arg Glu
        115                 120                 125

Glu Ala Lys Lys Phe Trp His His Phe Met Phe Arg Lys Thr Pro Ala
    130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
                165                 170                 175

Glu Lys Val Val Val Gln Asn Asn Leu Cys Phe Gly Lys Cys Gly Ser
            180                 185                 190

Val His Phe Pro Gly Ala Ala Gln His Ser His Thr Ser Cys Ser His
        195                 200                 205
```

```
Cys Leu Pro Ala Lys Phe Thr Thr Met His Leu Pro Leu Asn Cys Thr
    210                 215                 220
Glu Leu Ser Ser Val Ile Lys Val Val Met Leu Val Glu Glu Cys Gln
225                 230                 235                 240
Cys Lys Val Lys Thr Glu His Glu Asp Gly His Ile Leu His Ala Gly
                245                 250                 255
Ser Gln Asp Ser Phe Ile Pro Gly Val Ser Ala
            260                 265

<210> SEQ ID NO 53
<211> LENGTH: 1523
<212> TYPE: DNA
<213> ORGANISM: homo sapiens

<400> SEQUENCE: 53
ctggcgcggg cgggagctgc ggcggatacc cttgcgtgct gtggagaccc tactctcttc      60
gctgagaacg gccgctagcg gggactgaag gccgggagcc cactcccgac ccggggctag     120
cgtgcgtccc tagagtcgag cggggcaagg gagccagtgg ccgccgacgg ggaccgggaa     180 aactttttctg ggctcctggg cgcgccctgt agccgcgctc catgctccgg cagcggcccg   240
aaacccagcc ccgccgctga cggcgcccgc cgctccgggc agggcccatg ccctgcgcgc    300
tccgggggtc gtaggctgcc gccgagccgg ggctccggaa gccggcgggg gcgccgcggc    360
cgtgcggggc gtcaatggat cgccactcca gctacatctt catctggctg cagctggagc    420
tctgcgccat ggccgtgctg ctcaccaaag gtgaaattcg atgctactgt gatgctgccc    480
actgtgtagc cactggttat atgtgtaaat ctgagctcag cgcctgcttc tctagacttc    540
ttgatcctca gaactcaaat tccccactca cccatggctg cctggactct cttgcaagca    600
cgacagacat ctgccaagcc aaacaggccc gaaaccactc tggcaccacc atacccacat    660
tggaatgctg tcatgaagac atgtgcaatt acagagggct gcacgatgtt ctctctcctc    720
ccaggggtga ggcctcagga caaggaaaca ggtatcagca tgatggtagc agaaacctta    780
tcaccaaggt gcaggagctg acttcttcca aagagttgtg gttccgggca gcggtcattg    840
ccgtgcccat tgctggaggg ctgatttag tgttgcttat tatgttggcc ctgaggatgc      900
ttcgaagtga aaataagagg ctgcaggatc agcggcaaca gatgctctcc cgtttgcact    960
acagctttca cggacaccat tccaaaaagg ggcaggttgc aaagttagac ttggaatgca   1020
tggtgccggt cagtgggcac gagaactgct gtctgacctg tgataaaatg agacaagcag   1080
acctcagcaa cgataagatc ctctcgcttg ttcactgggg catgtacagt gggcacggga   1140
agctggaatt cgtatgacgg agtcttatct gaactacact tactgaacag cttgaaggcc   1200
ttttgagttc tgctggacag gagcacttta tctgaagaca aactcattta atcatctttg   1260
agagacaaaa tgacctctgc aaacagaatc ttggatattt cttctgaagg attatttgca   1320
cagacttaaa tacagttaaa tgtgttattt gcttttaaaa ttataaaaag caaagagaag   1380
actttgtaca cactgtcacc agggttattt gcatccaagg gagctggaat tgagtaccta   1440
aataaacaaa aatgtgccct atgtaagctt ctacatcttg atttattgta aagatttaaa   1500
agaaatatat atattttgtc tga                                           1523

<210> SEQ ID NO 54
<211> LENGTH: 260
<212> TYPE: PRT
<213> ORGANISM: homo sapiens
```

<400> SEQUENCE: 54

```
Met Asp Arg His Ser Ser Tyr Ile Phe Ile Trp Leu Gln Leu Glu Leu
1               5                   10                  15
Cys Ala Met Ala Val Leu Leu Thr Lys Gly Glu Ile Arg Cys Tyr Cys
            20                  25                  30
Asp Ala Ala His Cys Val Ala Thr Gly Tyr Met Cys Lys Ser Glu Leu
        35                  40                  45
Ser Ala Cys Phe Ser Arg Leu Leu Asp Pro Gln Asn Ser Asn Ser Pro
    50                  55                  60
Leu Thr His Gly Cys Leu Asp Ser Leu Ala Ser Thr Thr Asp Ile Cys
65                  70                  75                  80
Gln Ala Lys Gln Ala Arg Asn His Ser Gly Thr Thr Ile Pro Thr Leu
                85                  90                  95
Glu Cys Cys His Glu Asp Met Cys Asn Tyr Arg Gly Leu His Asp Val
            100                 105                 110
Leu Ser Pro Pro Arg Gly Glu Ser Gly Gln Gly Asn Arg Tyr Gln
        115                 120                 125
His Asp Gly Ser Arg Asn Leu Ile Thr Lys Val Gln Glu Leu Thr Ser
    130                 135                 140
Ser Lys Glu Leu Trp Phe Arg Ala Ala Val Ile Ala Val Pro Ile Ala
145                 150                 155                 160
Gly Gly Leu Ile Leu Val Leu Leu Ile Met Leu Ala Leu Arg Met Leu
                165                 170                 175
Arg Ser Glu Asn Lys Arg Leu Gln Asp Gln Arg Gln Gln Met Leu Ser
            180                 185                 190
Arg Leu His Tyr Ser Phe His Gly His His Ser Lys Lys Gly Gln Val
        195                 200                 205
Ala Lys Leu Asp Leu Glu Cys Met Val Pro Val Ser Gly His Glu Asn
    210                 215                 220
Cys Cys Leu Thr Cys Asp Lys Met Arg Gln Ala Asp Leu Ser Asn Asp
225                 230                 235                 240
Lys Ile Leu Ser Leu Val His Trp Gly Met Tyr Ser Gly His Gly Lys
                245                 250                 255
Leu Glu Phe Val
            260
```

<210> SEQ ID NO 55
<211> LENGTH: 23
<212> TYPE: DNA
<213> ORGANISM: Artificial
<220> FEATURE:
<223> OTHER INFORMATION: Synthetic primer

<400> SEQUENCE: 55
aggccaaccg cgagaagatg acc                                    23

<210> SEQ ID NO 56
<211> LENGTH: 22
<212> TYPE: DNA
<213> ORGANISM: Artificial
<220> FEATURE:
<223> OTHER INFORMATION: Synthetic primer

<400> SEQUENCE: 56
gaagtccagg gcgacgtagc ac                                     22